United States Patent
Davila

(10) Patent No.: US 11,951,129 B2
(45) Date of Patent: Apr. 9, 2024

(54) COMPOSITIONS AND METHODS FOR TARGETING CLEC12A-EXPRESSING CANCERS

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 944 days.

(21) Appl. No.: 16/960,653

(22) PCT Filed: Jan. 8, 2019

(86) PCT No.: PCT/US2019/012664
§ 371 (c)(1),
(2) Date: Jul. 8, 2020

(87) PCT Pub. No.: WO2019/139888
PCT Pub. Date: Jul. 18, 2019

(65) Prior Publication Data
US 2020/0345779 A1 Nov. 5, 2020

Related U.S. Application Data

(60) Provisional application No. 62/767,865, filed on Nov. 15, 2018, provisional application No. 62/767,859, filed on Nov. 15, 2018, provisional application No. 62/730,397, filed on Sep. 12, 2018, provisional application No. 62/730,390, filed on Sep. 12, 2018, provisional application No. 62/654,623, filed on Apr. 9, 2018, provisional application No. 62/654,621, filed on Apr. 9, 2018, provisional application No. 62/615,096, filed on Jan. 9, 2018.

(51) Int. Cl.
*A61K 35/17* (2015.01)
*C07K 14/725* (2006.01)
*A61K 45/06* (2006.01)

(52) U.S. Cl.
CPC .......... *A61K 35/17* (2013.01); *C07K 14/7051* (2013.01); *A61K 45/06* (2013.01); *C07K 2317/31* (2013.01); *C07K 2317/622* (2013.01); *C07K 2317/626* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 6,440,735 | B1 | 8/2002 | Gaeta |
| 6,713,055 | B2 | 3/2004 | Schiff |
| 8,008,449 | B2 | 8/2011 | Korman et al. |
| 8,552,154 | B2 | 10/2013 | Freeman et al. |
| 8,617,546 | B2 | 12/2013 | Kang et al. |
| 2006/0233787 | A1 | 10/2006 | Le Gall et al. |
| 2009/0186027 | A1 | 7/2009 | Solomon et al. |
| 2016/0051651 | A1 | 2/2016 | Brogdon et al. |
| 2017/0204194 | A1 | 7/2017 | Chen et al. |

FOREIGN PATENT DOCUMENTS

| | | |
|---|---|---|
| CN | 106163547 A | 11/2016 |
| CN | 107109420 A | 8/2017 |
| CN | 107406516 A | 11/2017 |
| CN | 111116753 A | 5/2020 |
| WO | 99/057150 | 11/1999 |
| WO | 2015/039523 A1 | 3/2015 |
| WO | 2016/014535 A1 | 1/2016 |
| WO | 2016014535 A1 | 1/2016 |
| WO | 2017/091615 A1 | 6/2017 |
| WO | 2017091615 A1 | 6/2017 |

OTHER PUBLICATIONS

Gussow et al (Methods in Enzymology. 1991; 203: 99-121).*
Winkler et al (J. Imm., 265:4505-4514, 2000).*
Boerner, Paula, et al., "Production of Antigen-Specific Human Monoclonal Antibodies from In Vitro-Primed Human Splenocytes," The Journal of Immunology, vol. 147, No. 1 (1991), pp. 86-95.
Brüggemann, Marianne, et al., "Designer Mice: The Production of Human Antibody Repertoires in Transgenic Animals," Generation of Antibodies by Cell and Gene Immortalization, Year Immunology, Basel, Karger, vol. 7 (1993), pp. 33-40.
Cole, S.P.C., et al., "The EBV-Hybridoma Technique and its Application to Human Lung Cancer," Monoclonal Antibodies and Cancer Therapy (1985), pp. 77-96.
Fauriat, C., et al., "Impaired activating receptor expression pattern in natural killer cells from patients with multiple myeloma," Leukemia, vol. 20 (2006), pp. 732-733.

(Continued)

*Primary Examiner* — Brad Duffy
(74) *Attorney, Agent, or Firm* — Thomas | Horstemeyer, LLP

(57) ABSTRACT

Disclosed are compositions and methods for targeted treatment of CLEC12A-expressing cancers. In particular, chimeric antigen receptor (CAR) polypeptides are disclosed that can be used with adoptive cell transfer to target and kill CLEC12A-expressing cancers. Also disclosed are immune effector cells, such as T cells or Natural Killer (NK) cells, that are engineered to express these CARs. Therefore, also disclosed are methods of providing an anti-tumor immunity in a subject with a CLEC12A-expressing cancer that involves adoptive transfer of the disclosed immune effector cells engineered to express the disclosed CARs. Also disclosed are multivalent antibodies are disclosed that are able to engage T-cells to destroy CLEC12A-expressing malignant cells.

12 Claims, 11 Drawing Sheets

Specification includes a Sequence Listing.

(56) References Cited

OTHER PUBLICATIONS

Fesnak, Andrew D., et al., "Engineered T cells: the promise and challenges of cancer immunotherapy," Nature, vol. 16 (2016), pp. 566-591.
Godfrey, James, et al., "The role of natural killer cells in immunity against multiple myeloma," Leukemia & Lymphoma, vol. 53, No. 9 (2012), pp. 1666-1676.
Hoogenboom, Hennie R., et al., "By-passing Immunisation Human Antibodies from Synthetic Repertoires of Germline Vh Gene Segments Rearranged in Vitro," Journal of Molecular Biology, vol. 227 (1992), pp. 381-388.
Imai, C., et al., "Chimeric receptors with 4-1BB signaling capacity provoke potent cytotoxicity against acute lymphoblastic leukemia," Leukemia, vol. 18 (2004), pp. 676-684.
Jakobovits, Aya, et al., "Germ-line transmission and expression of human-derived yeast artificial chromosome," Nature, vol. 362 (1993), p. 225.
Jones, Peter T., et al., "Replacing the complementarity-determining regions in a human antibody with those from a mouse," Nature, vol. 321 (1986), pp. 522-525.
Maher, John, et al., "Human T-lymocyte cytotoxicity and proliferation directed by a single chimeric TCRZ/CD28 receptor," Nature, vol. 20 (2002), pp. 70-75.
Marks, James D., et al., "By-passing Immunization Human Antibodies from V-gene Libraries Displayed on Phage," Journal of Molecular Biology, vol. 222 (1991), pp. 581-597.
Presta, Leonard G., "Antibody engineering," Biotechnology, vol. 3 (1992), pp. 394-398.
Riechmann, Lutz, et al., "Reshaping human antibodies for therapy," Nature, vol. 332 (1988), pp. 323-327.
Rosenberg, Steven A., et al., "Use of Tumour-Infiltrating Lymphocytes and Interleukin-2 in the Immunotherapy of Patients with Metastatic Melanoma," The New England Journal of Medicine, vol. 319, No. 25 (1988), pp. 1676-1680.
Verhoeyen, Martine, et al., "Reshaping Human Antibodies: Grafting an Antilysozyme Activity," Science, vol. 239 (1988), pp. 1534-1536.
Woof, Jenny M., et al., "Human Antibody-FC Receptor Interactions Illuminated by Crystal Structures," Nature, vol. 4 (2004), 11 pages.
Smith, Corey, et al., "Effective Treatment of Metastatic Forms of Epstein-Barr Virus-Associated Nasopharyngeal Carcinoma with Novel Adenovirus-Based Adoptive Immunotherapy," Cancer Research, vol. 72, No. 5 (2012), pp. 1116-1125.
Porter, David L., et al., "Chimeric Antigen Receptor-Modified T Cells in Chronic Lymphoid Leukemia," The New England Journal of Medicine, vol. 365 (2011), pp. 725-733.
Narni-Mancinelli, Emilie, et al., "The 'T-cell-ness' of NK cells: unexpected similarities between NK cells and T cells," International Immunology, vol. 23, No. 7 (2011), pp. 427-431.
Morgan, Richard A., et al., "Case Report of a Serious Adverse Event Following the Administration of T Cells Transduced With a Chimeric Antigen Receptor Recognizing ERBB2," Molecular Therapy, vol. 18, No. 4 (2010), pp. 843-851.
Koehne, Guenther, et al., "Quantitation, selection, and functional characterization of Epstein-Barr virus-specific and alloreactive T cells deteced by intracellular interferon-y production and growth of cytotoxic precursors," Blood, vol. 99, No. 1 (2002), pp. 1730-1740.
Jakobovits, Aya, et al., "Analaysis of homozygous mutant chimeric mice: Deletion of the immunoglobulin heavy- chain joining region blocks B-cell development and antibody production," Proc. Natl. Acad. Sci., vol. 90 (1993), pp. 2551-2555.
Doubrovina, Ekaterina, et al., "Adoptive immunotherapy with unselected or EBV-specific T cells for biopsy-proven EBV+ lymphomas after allogeneic hematopoietic cell transplantation," Blood, vol. 119, No. 11 (2012), pp. 2644-2656.
Barker, Juliet, N., et al., "Successful treatment of EBV-associated posttransplantation lymphoma after cord blood transplantation using third-party EBV-specific cytotoxic T lymphocytes," Blood, vol. 116, No. 23 (2010), pp. 5045-5049.
CN Office Action and Search Report, CN Patent Application No. 201980016554.1, dated Apr. 12, 2023.
International Search Report issued for PCT/US2019/012664, dated May 31, 2019.
Rossig et al., Epstein-barr virus-specific human T lymphocytes expressing antitumor chimeric T-Cell receptors: potential for improved immunotherapy, Blood, vol. 99, No. 6, p. 2009-2016, 2002.
Search Report and Written Opinion issued by the European Patent Office for application 19738689.9, dated Sep. 24, 2021.
Kenderian et al., Targeting CLEC12A with Chimeric Antigen Receptor T Cells Can Overcome the Chemotherapy Refractoriness of Leukemia Stem Cells, Biology of Blood and Marrow Transplantation, vol. 23, No. 3, 268, 2017.
Noordhuis et al., Targeting of CLEC12A in Acute Myeloid Leukemia by Antibody-Drug-Conjugates and Bispecific CLL-1xCD3 Bite Antibody, Blood, American Society of Hematology, US, vol. 116, No. 21, 2890, 2010.
European Office Action, EP Patent Application No. 19738689.9, dated Aug. 30, 2022.
Nenderain, Saad S., et al., "Targeting CLEC12A with Chimeric Antigen Receptor T Cells Can Overcome the Chemotherapy Refractoriness of Leukemia Stem Cells," Biology Blood Marrow Transplant, vol. 23 (2017), pp. S206-S207.
Noordhuis, Paul, et al., "Targeting of Clecl 12A in Acute Myeloid Leukemia by Antibody-Drug-Conjugates and Bispecific CLL-1xCD3 BiTE Antibody," Blood, vol. 116, No. 21 (2010), p. 2890.
Iu, Xiaojun, et al., "Affinity-tuned ErbB2 or EGFR chimeric antigen receptor T cells exhibit an increased therapeutic Index against tumors in mice," Cancer Reseach, vol. 75, No. 17 (2015), pp. 3596-3607.

* cited by examiner

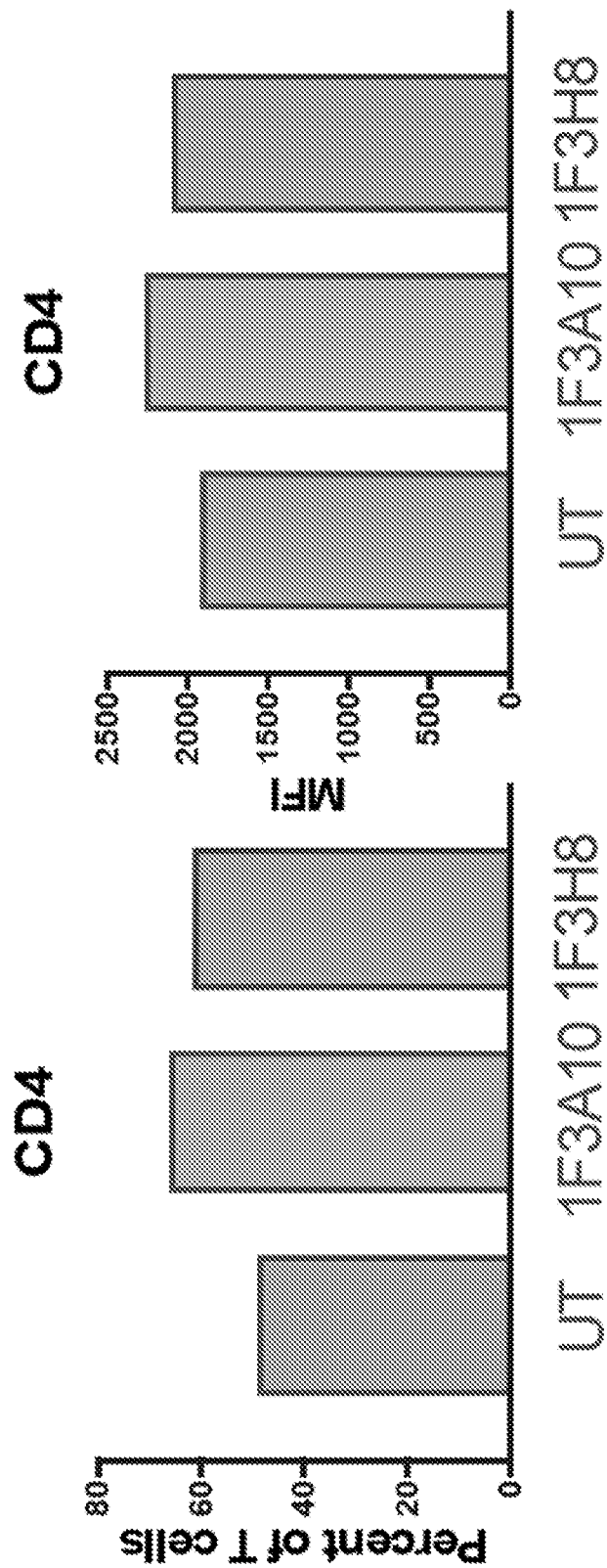

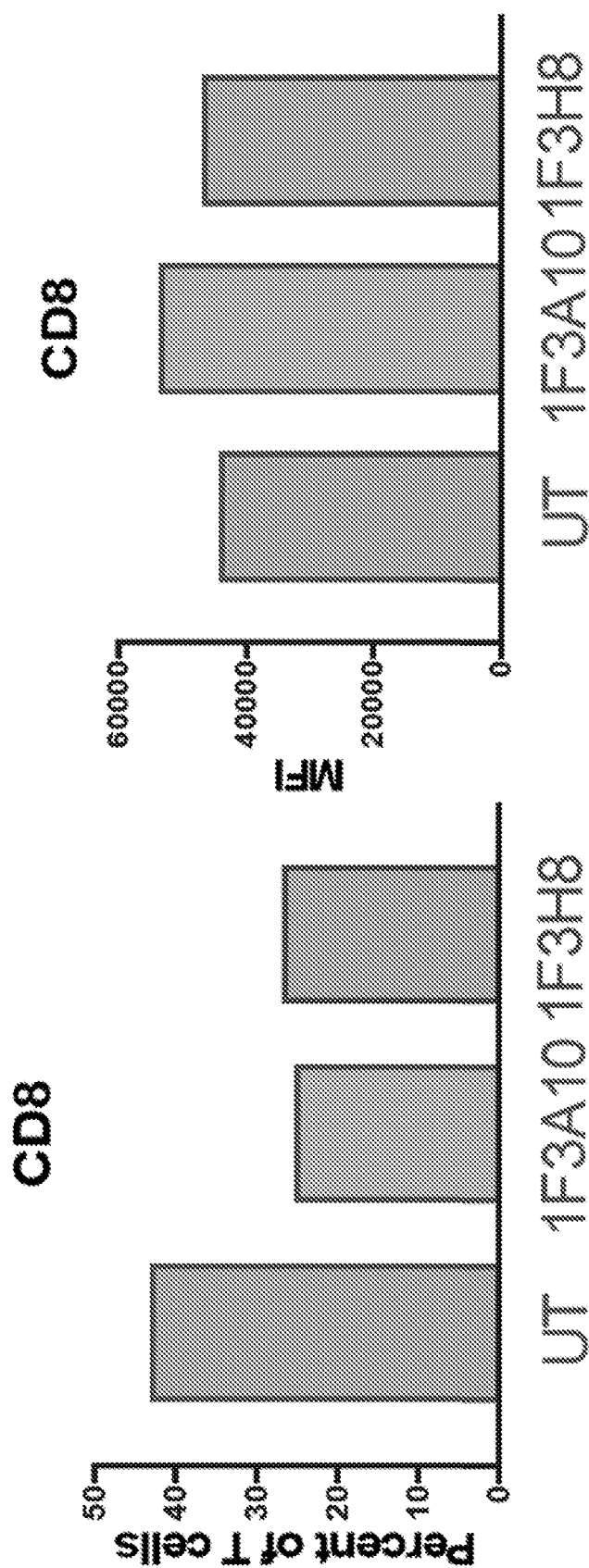

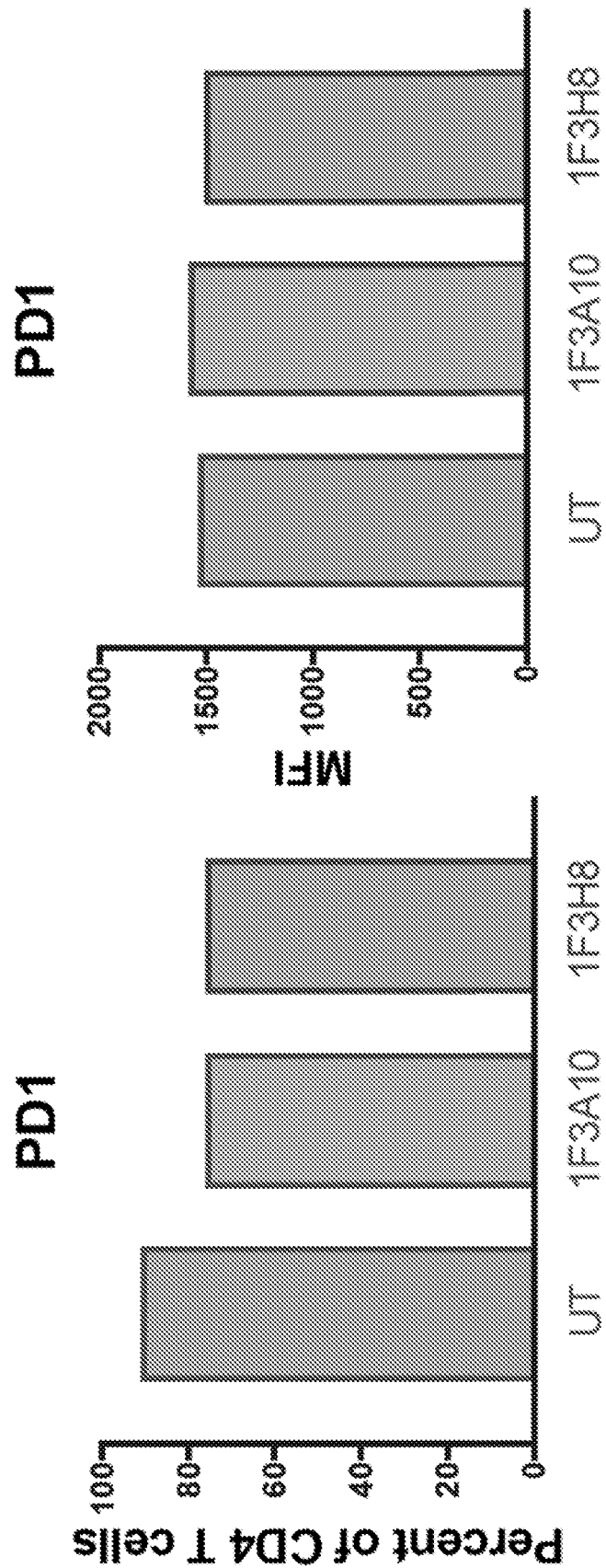

```
                      SEQUENCE LISTING

<160> NUMBER OF SEQ ID NOS: 30

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Ser Phe Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Ser Phe Ala Val Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Ser His Asp Met Ser
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Ile Ser Ser Gly Gly Ala Tyr Thr
1               5

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Thr Ile Ser Ser Gly Gly Ala Tyr Thr Phe Tyr Lys Asp Ser Val Lys
1               5                   10                  15

Gly Arg Phe Thr
            20
```

-continued

```
<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Tyr Ile Ser Gly Gly Gly Thr Asn Ile Tyr Tyr Ser Asp Thr Val Lys
1               5                   10                  15

Gly Arg Phe Thr
            20

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Ala Arg His Ser Gly Tyr Asp Gly Tyr Tyr Leu Tyr Ala Met Asp Tyr
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic Construct

<400> SEQUENCE: 8

His Ser Gly Tyr Asp Gly Tyr Tyr Leu Tyr Ala Met Asp Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Pro Asn Tyr Asn Tyr Gly Gly Ser Trp Phe Ala Tyr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ser Ser Val His Tyr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Ala Ser Ser Ser Val His Tyr Met His
1               5
```

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Ser Ala Ser Ser Ser Val His Tyr Met His
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 13

Asp Thr Ser Xaa
1

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Asp Thr Ser Lys Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Gln Gln Trp Thr Ser Asn Pro Pro Thr
1               5

<210> SEQ ID NO 16
<211> LENGTH: 123
<212> TYPE: PRT
<213> ORGANISM: Artificial Sequence
<220> FEATURE:
<223> OTHER INFORMATION: Synthetic Construct

<400> SEQUENCE: 16

Glu Leu Ile Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Thr Ile Ser Ser Gly Gly Ala Tyr Thr Phe Tyr Lys Asp Ser Val
    50                  55                  60

```
Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Ser Ala Met Tyr Tyr Cys
                 85                  90                  95

Ala Arg His Ser Gly Tyr Asp Gly Tyr Tyr Leu Tyr Ala Met Asp Tyr
            100                 105                 110

Trp Gly Gln Gly Thr Ser Val Thr Val Ser Ser
            115                 120
```

<210> SEQ ID NO 17
<211> LENGTH: 369
<212> TYPE: DNA
<213> ORGANISM: Artificial Sequence
<220> FEATURE:
<223> OTHER INFORMATION: Synthetic Construct

<400> SEQUENCE: 17

```
gaactaatac tggtggagtc tgggggaggc ttagtgaagc ctggagggtc cctgaaactc      60
tcctgtgcag tctctggatt cactttcagt tcctttgcca tgtcttgggt tcgccagact     120
ccggagaaga ggctggagtg ggtcgcaacc attagtagtg gtggagctta caccttctat     180
aaagacagtg tgaaggggcg attcaccatc tccagagaca tgccaagaa tacccctgtac    240
ctgcaaatga gcagtctgag gtctgaggac tcggccatgt attactgtgc aagacatagc     300
ggctatgatg gttactacct ctatgctatg gactactggg gtcaaggaac ctcagtcacc     360
gtctcctca                                                             369
```

<210> SEQ ID NO 18
<211> LENGTH: 127
<212> TYPE: PRT
<213> ORGANISM: Artificial Sequence
<220> FEATURE:
<223> OTHER INFORMATION: Synthetic Construct

<400> SEQUENCE: 18

```
Gly Val Gln Cys Glu Leu Ile Leu Val Glu Ser Gly Gly Gly Leu Val
 1               5                  10                  15

Lys Pro Gly Gly Ser Leu Lys Leu Ser Cys Ala Val Ser Gly Phe Thr
             20                  25                  30

Phe Ser Ser Phe Ala Val Ser Trp Val Arg Gln Thr Pro Glu Lys Arg
         35                  40                  45

Leu Glu Trp Val Ala Thr Ile Ser Ser Gly Gly Ala Tyr Thr Phe Tyr
     50                  55                  60

Lys Asp Ser Val Lys Gly Arg Phe Thr Ile Ser Arg Asp Asn Ala Lys
 65                  70                  75                  80

Asn Thr Leu Tyr Leu Gln Met Ser Ser Leu Arg Ser Glu Asp Ser Ala
                 85                  90                  95

Met Tyr Tyr Cys Ala Arg His Ser Gly Tyr Asp Gly Tyr Tyr Leu Tyr
            100                 105                 110

Ala Met Asp Tyr Trp Gly Gln Gly Thr Ser Val Thr Val Ser Ser
        115                 120                 125
```

<210> SEQ ID NO 19
<211> LENGTH: 381
<212> TYPE: DNA
<213> ORGANISM: Artificial Sequence
<220> FEATURE:
<223> OTHER INFORMATION: Synthetic Construct

<400> SEQUENCE: 19

```
ggtgtccagt gtgaactaat actggtggag tctgggggag gcttagtgaa gcctggaggg    60
tccctgaaac tcctctgtgc agtctctgga ttcactttca gttcctttgc cgtgtcctgg   120
gttcgccaga ctccggagaa gaggctggag tgggtcgcaa ccattagtag tggtggagct   180
tacaccttct ataagacagt gtgaaggggc gattcacca tctccagaga caatgccaag   240
aataccctgt acctgcaaat gagcagtctg aggtctgagg actcggccat gtattactgt   300
gcaagacata gcggctatga tggttactac ctctatgcta tggactactg gggtcaagga   360
acctcagtca ccgtctcctc a                                             381
```

<210> SEQ ID NO 20
<211> LENGTH: 121
<212> TYPE: PRT
<213> ORGANISM: Artificial Sequence
<220> FEATURE:
<223> OTHER INFORMATION: Synthetic Construct

<400> SEQUENCE: 20

```
Glu Val Gln Leu Glu Glu Ser Gly Gly Gly Leu Val Gln Pro Gly Gly
1               5                   10                  15

Ser Leu Lys Val Ser Cys Ala Val Ser Gly Leu Ala Phe Ser Ser His
            20                  25                  30

Asp Met Ser Trp Val Arg Gln Thr Pro Glu Lys Arg Leu Glu Trp Val
        35                  40                  45

Ala Tyr Ile Ser Gly Gly Gly Thr Asn Ile Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg Pro Asn Tyr Asn Tyr Gly Gly Ser Trp Phe Ala Tyr Trp Gly
            100                 105                 110

Gln Gly Thr Leu Val Thr Val Ser Ala
        115                 120
```

<210> SEQ ID NO 21
<211> LENGTH: 363
<212> TYPE: DNA
<213> ORGANISM: Artificial Sequence
<220> FEATURE:
<223> OTHER INFORMATION: Synthetic Construct

<400> SEQUENCE: 21

```
gaggtgcagc tggaggagtc tgggggaggc ttagtgcagc cggagggtc cctgaaagtc     60 tcctgtgcag tttccggact cgctttcagc agccatgaca tgtcttgggt tcgccagact   120
ccggagaagc ggctggagtg ggtcgcatac attagtggag gtggtactaa tatctattat   180
tcagacactg tgaaggggcg attcaccatc tccagagaca atgccaagaa caccctgtac   240
ctgcaaatga gcagtctgaa gtctgaagac acagccattt attactgtgc aagacccaat   300
tataattacg gcggttcctg gtttgcttac tggggccaag gactctggt cactgtctct   360 gca                                                                 363
```

<210> SEQ ID NO 22
<211> LENGTH: 106
<212> TYPE: PRT
<213> ORGANISM: Artificial Sequence
<220> FEATURE:

<223> OTHER INFORMATION: Synthetic Construct

<400> SEQUENCE: 22

Gln Ile Val Leu Thr Gln Ser Pro Glu Ile Met Ser Ala Ser Pro Gly
1               5                   10                  15

Glu Lys Val Thr Met Thr Cys Ser Ala Ser Ser Val His Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Thr Ser Tyr Ser Leu Thr Ile Ser Ser Met Glu Ser Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 23
<211> LENGTH: 320
<212> TYPE: DNA
<213> ORGANISM: Artificial Sequence
<220> FEATURE:
<223> OTHER INFORMATION: Synthetic Construct

<400> SEQUENCE: 23
caaattgttc tcacccagtc tccagaaatc atgtctgcat ctccagggga gaaggtcacc        60
atgacctgca gtgccagctc aagtgtacat tacatgcact ggtaccagca gaagtcaggc       120 acctcccca aaagatggat ttatgacaca tccaaactgg cttctggagt ccctggtcgc        180
ttcagtggca gtgggtctgg gacctcttac tctctcacaa tcagcagcat ggagtctgaa       240
gatgctgcca cttattactg ccagcagtgg actagtaacc cacccacgtt cggagggggg       300
accaagctgg aaattaaacg                                                   320

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Gly Gly Gly Gly Ser Gly Gly Gly Ser Gly Gly Gly Gly Ser
1               5                   10                  15

<210> SEQ ID NO 25
<211> LENGTH: 244
<212> TYPE: PRT
<213> ORGANISM: Artificial Sequence
<220> FEATURE:
<223> OTHER INFORMATION: Synthetic Construct

<400> SEQUENCE: 25

Glu Leu Ile Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Ser Phe
            20                  25                  30

Ala Met Ser Trp Val Arg Gln Thr Pro Glu Lys Arg Leu Glu Trp Val
        35                  40                  45

```
Ala Thr Ile Ser Ser Gly Gly Ala Tyr Thr Phe Tyr Lys Asp Ser Val
    50              55                  60

Lys Gly Arg Phe Thr Ile Ser Arg Asp Asn Ala Lys Asn Thr Leu Tyr
 65              70                  75                  80

Leu Gln Met Ser Ser Leu Arg Ser Glu Asp Ser Ala Met Tyr Tyr Cys
                 85                  90                  95

Ala Arg His Ser Gly Tyr Asp Gly Tyr Tyr Leu Tyr Ala Met Asp Tyr
                100                 105                 110

Trp Gly Gln Gly Thr Ser Val Thr Val Ser Ser Gly Gly Gly Gly Ser
            115                 120                 125

Gly Gly Gly Gly Ser Gly Gly Gly Ser Gln Ile Val Leu Thr Gln
    130                 135                 140

Ser Pro Glu Ile Met Ser Ala Ser Pro Gly Glu Lys Val Thr Met Thr
145                 150                 155                 160

Cys Ser Ala Ser Ser Ser Val His Tyr Met His Trp Tyr Gln Gln Lys
                165                 170                 175

Ser Gly Thr Ser Pro Lys Arg Trp Ile Tyr Asp Thr Ser Lys Leu Ala
            180                 185                 190

Ser Gly Val Pro Gly Arg Phe Ser Gly Ser Gly Ser Gly Thr Ser Tyr
            195                 200                 205

Ser Leu Thr Ile Ser Ser Met Glu Ser Glu Asp Ala Ala Thr Tyr Tyr
    210                 215                 220

Cys Gln Gln Trp Thr Ser Asn Pro Pro Thr Phe Gly Gly Gly Thr Lys
225                 230                 235                 240

Leu Glu Ile Lys

<210> SEQ ID NO 26
<211> LENGTH: 248
<212> TYPE: PRT
<213> ORGANISM: Artificial Sequence
<220> FEATURE:
<223> OTHER INFORMATION: Synthetic Construct

<400> SEQUENCE: 26

Gly Val Gln Cys Glu Leu Ile Leu Val Glu Ser Gly Gly Gly Leu Val
 1               5                  10                  15

Lys Pro Gly Gly Ser Leu Lys Leu Ser Cys Ala Val Ser Gly Phe Thr
             20                  25                  30

Phe Ser Ser Phe Ala Val Ser Trp Val Arg Gln Thr Pro Glu Lys Arg
             35                  40                  45

Leu Glu Trp Val Ala Thr Ile Ser Ser Gly Gly Ala Tyr Thr Phe Tyr
     50                  55                  60

Lys Asp Ser Val Lys Gly Arg Phe Thr Ile Ser Arg Asp Asn Ala Lys
 65                  70                  75                  80

Asn Thr Leu Tyr Leu Gln Met Ser Ser Leu Arg Ser Glu Asp Ser Ala
                 85                  90                  95

Met Tyr Tyr Cys Ala Arg His Ser Gly Tyr Asp Gly Tyr Tyr Leu Tyr
                100                 105                 110

Ala Met Asp Tyr Trp Gly Gln Gly Thr Ser Val Thr Val Ser Ser Gly
            115                 120                 125

Gly Gly Gly Ser Gly Gly Gly Gly Ser Gly Gly Gly Gly Ser Gln Ile
    130                 135                 140

Val Leu Thr Gln Ser Pro Glu Ile Met Ser Ala Ser Pro Gly Glu Lys
145                 150                 155                 160

Val Thr Met Thr Cys Ser Ala Ser Ser Ser Val His Tyr Met His Trp
```

```
                    165                 170                 175

Tyr Gln Gln Lys Ser Gly Thr Ser Pro Lys Arg Trp Ile Tyr Asp Thr
                180                 185                 190

Ser Lys Leu Ala Ser Gly Val Pro Gly Arg Phe Ser Gly Ser Gly Ser
                195                 200                 205

Gly Thr Ser Tyr Ser Leu Thr Ile Ser Ser Met Glu Ser Glu Asp Ala
            210                 215                 220

Ala Thr Tyr Tyr Cys Gln Gln Trp Thr Ser Asn Pro Pro Thr Phe Gly
225                 230                 235                 240

Gly Gly Thr Lys Leu Glu Ile Lys
                245

<210> SEQ ID NO 27
<211> LENGTH: 242
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Glu Glu Ser Gly Gly Gly Leu Val Gln Pro Gly Gly
1               5                   10                  15

Ser Leu Lys Val Ser Cys Ala Val Ser Gly Leu Ala Phe Ser Ser His
                20                  25                  30

Asp Met Ser Trp Val Arg Gln Thr Pro Glu Lys Arg Leu Glu Trp Val
            35                  40                  45

Ala Tyr Ile Ser Gly Gly Gly Thr Asn Ile Tyr Tyr Ser Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg Pro Asn Tyr Asn Tyr Gly Gly Ser Trp Phe Ala Tyr Trp Gly
            100                 105                 110

Gln Gly Thr Leu Val Thr Val Ser Ala Gly Gly Gly Ser Gly Gly Gly
        115                 120                 125

Gly Gly Ser Gly Gly Gly Gly Ser Gln Ile Val Leu Thr Gln Ser Pro
    130                 135                 140

Glu Ile Met Ser Ala Ser Pro Gly Glu Lys Val Thr Met Thr Cys Ser
145                 150                 155                 160

Ala Ser Ser Ser Val His Tyr Met His Trp Tyr Gln Gln Lys Ser Gly
                165                 170                 175

Thr Ser Pro Lys Arg Trp Ile Tyr Asp Thr Ser Lys Leu Ala Ser Gly
            180                 185                 190

Val Pro Gly Arg Phe Ser Gly Ser Gly Ser Gly Thr Ser Tyr Ser Leu
        195                 200                 205

Thr Ile Ser Ser Met Glu Ser Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys

<210> SEQ ID NO 28
<211> LENGTH: 244
<212> TYPE: PRT
<213> ORGANISM: Artificial Sequence
```

```
<220> FEATURE:
<223> OTHER INFORMATION: Synthetic Construct

<400> SEQUENCE: 28

Gln Ile Val Leu Thr Gln Ser Pro Glu Ile Met Ser Ala Ser Pro Gly
1               5                   10                  15

Glu Lys Val Thr Met Thr Cys Ser Ala Ser Ser Val His Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Thr Ser Tyr Ser Leu Thr Ile Ser Ser Met Glu Ser Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Gly Ser Gly
                100                 105                 110

Gly Gly Gly Ser Gly Gly Gly Ser Glu Leu Ile Leu Val Glu Ser
            115                 120                 125

Gly Gly Gly Leu Val Lys Pro Gly Gly Ser Leu Lys Leu Ser Cys Ala
        130                 135                 140

Val Ser Gly Phe Thr Phe Ser Ser Phe Ala Met Ser Trp Val Arg Gln
145                 150                 155                 160

Thr Pro Glu Lys Arg Leu Glu Trp Val Ala Thr Ile Ser Ser Gly Gly
                165                 170                 175

Ala Tyr Thr Phe Tyr Lys Asp Ser Val Lys Gly Arg Phe Thr Ile Ser
                180                 185                 190

Arg Asp Asn Ala Lys Asn Thr Leu Tyr Leu Gln Met Ser Ser Leu Arg
            195                 200                 205

Ser Glu Asp Ser Ala Met Tyr Tyr Cys Ala Arg His Ser Gly Tyr Asp
        210                 215                 220

Gly Tyr Tyr Leu Tyr Ala Met Asp Tyr Trp Gly Gln Gly Thr Ser Val
225                 230                 235                 240

Thr Val Ser Ser

<210> SEQ ID NO 29
<211> LENGTH: 248
<212> TYPE: PRT
<213> ORGANISM: Artificial Sequence
<220> FEATURE:
<223> OTHER INFORMATION: Synthetic Construct

<400> SEQUENCE: 29

Gln Ile Val Leu Thr Gln Ser Pro Glu Ile Met Ser Ala Ser Pro Gly
1               5                   10                  15

Glu Lys Val Thr Met Thr Cys Ser Ala Ser Ser Val His Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Thr Ser Tyr Ser Leu Thr Ile Ser Ser Met Glu Ser Glu
65                  70                  75                  80

Asp Ala Ala Thr Tyr Tyr Cys Gln Gln Trp Thr Ser Asn Pro Pro Thr
                85                  90                  95
```

```
Phe Gly Gly Gly Thr Lys Leu Glu Ile Lys Gly Gly Gly Ser Gly
                100                 105                 110

Gly Gly Gly Ser Gly Gly Gly Ser Gly Val Gln Cys Glu Leu Ile
            115                 120                 125

Leu Val Glu Ser Gly Gly Leu Val Lys Pro Gly Gly Ser Leu Lys
130                 135                 140

Leu Ser Cys Ala Val Ser Gly Phe Thr Phe Ser Ser Phe Ala Val Ser
145                 150                 155                 160

Trp Val Arg Gln Thr Pro Glu Lys Arg Leu Glu Trp Val Ala Thr Ile
                165                 170                 175

Ser Ser Gly Gly Ala Tyr Thr Phe Tyr Lys Asp Ser Val Lys Gly Arg
                180                 185                 190

Phe Thr Ile Ser Arg Asp Asn Ala Lys Asn Thr Leu Tyr Leu Gln Met
                195                 200                 205

Ser Ser Leu Arg Ser Glu Asp Ser Ala Met Tyr Tyr Cys Ala Arg His
210                 215                 220

Ser Gly Tyr Asp Gly Tyr Tyr Leu Tyr Ala Met Asp Tyr Trp Gly Gln
225                 230                 235                 240

Gly Thr Ser Val Thr Val Ser Ser
                245

<210> SEQ ID NO 30
<211> LENGTH: 242
<212> TYPE: PRT
<213> ORGANISM: Artificial Sequence
<220> FEATURE:
<223> OTHER INFORMATION: Synthetic Construct

<400> SEQUENCE: 30

Gln Ile Val Leu Thr Gln Ser Pro Glu Ile Met Ser Ala Ser Pro Gly
1               5                   10                  15

Glu Lys Val Thr Met Thr Cys Ser Ala Ser Ser Ser Val His Tyr Met
                20                  25                  30

His Trp Tyr Gln Gln Lys Ser Gly Thr Ser Pro Lys Arg Trp Ile Tyr
                35                  40                  45

Asp Thr Ser Lys Leu Ala Ser Gly Val Pro Gly Arg Phe Ser Gly Ser
    50                  55                  60

Gly Ser Gly Thr Ser Tyr Ser Leu Thr Ile Ser Ser Met Glu Ser Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Gly Gly Ser Gly
                100                 105                 110

Gly Gly Gly Ser Gly Gly Gly Gly Ser Glu Val Gln Leu Glu Glu Ser
            115                 120                 125

Gly Gly Gly Leu Val Gln Pro Gly Gly Ser Leu Lys Val Ser Cys Ala
            130                 135                 140

Val Ser Gly Leu Ala Phe Ser Ser His Asp Met Ser Trp Val Arg Gln
145                 150                 155                 160

Thr Pro Glu Lys Arg Leu Glu Trp Val Ala Tyr Ile Ser Gly Gly Gly
                165                 170                 175

Thr Asn Ile Tyr Tyr Ser Asp Thr Val Lys Gly Arg Phe Thr Ile Ser
                180                 185                 190

Arg Asp Asn Ala Lys Asn Thr Leu Tyr Leu Gln Met Ser Ser Leu Lys
                195                 200                 205
```

```
Ser Glu Asp Thr Ala Ile Tyr Tyr Cys Ala Arg Pro Asn Tyr Asn Tyr
    210             215             220

Gly Gly Ser Trp Phe Ala Tyr Trp Gly Gln Gly Thr Leu Val Thr Val
225             230             235             240

Ser Ala
```

COMPOSITIONS AND METHODS FOR TARGETING CLEC12A-EXPRESSING CANCERS

CROSS-REFERENCE TO RELATED APPLICATIONS

This application is a National Stage of International Application No. PCT/US2019/012664, filed Jan. 8, 2019, which claims benefit of U.S. Provisional Application Ser. No. 62/615,096, filed Jan. 9, 2018, Application Ser. No. 62/654,621, filed Apr. 9, 2018, Application Ser. No. 62/654,623, filed Apr. 9, 2018, Application Ser. No. 62/730,390, filed Sep. 12, 2018, Application Ser. No. 62/730,397, filed Sep. 12, 2018, Application Ser. No. 62/767,859, filed Nov. 15, 2018, and Application Ser. No. 62/767,865, filed Nov. 15, 2018, which are all hereby incorporated herein by reference in their entirety.

SEQUENCE LISTING

This application contains a sequence listing filed in electronic form as an ASCII.txt file entitled "320103-2040 Sequence Listing_ST25" created on Jan. 6, 2019. The content of the sequence listing is incorporated herein in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Compositions and methods for targeted treatment of CLEC12A-expressing cancers are disclosed. For example, anti-CLEC12A monoclonal antibodies from hybridomas 1F3, 1F8, 1G3, 2A10, 3F12, 4E3, 4E10, 5B2, 5F10, 6C7, 9A2, 11C7, 11H1, and 12D6 are provided herein. Also disclosed are recombinant, humanized, and/or chimeric antibodies comprising at least the antigen binding regions of one or more of these antibodies.

Also disclosed herein are multispecific, multivalent antibodies that are able to engage T-cells to destroy CLEC12A-expressing malignant cells. For example, the antibody can be a bi-specific T-cell engager. The antibodies can be engineered from fusion polypeptides, such as fusion polypeptides having the following formula:

$V_L I\text{-}V_H I\text{-}V_L T\text{-}V_H T$, $V_L T\text{-}V_H T\text{-}V_L I\text{-}V_H I$, $V_H T\text{-}V_L T\text{-}V_H I\text{-}V_L I$, $V_H I\text{-}V_L I\text{-}V_H T\text{-}V_L T$, $V_L I\text{-}V_H I\text{-}V_H T\text{-}V_L T$, $V_L T\text{-}V_H T\text{-}V_H I\text{-}V_L I$, wherein "$V_L I$" is a light chain variable domain specific for an immune cell antigen;

wherein "$V_H T$" is a heavy chain variable domain specific for CLEC12A;

wherein "$V_L T$" is a light chain variable domain specific for CLEC12A;

wherein "$V_H I$" is a heavy chain variable domain specific for the immune cell antigen; and wherein "-" consists of a peptide linker or a peptide bond.

The immune cell antigen can be a cell surface molecule that is expressed on human NK cells, T cells, monocytes, macrophages or granulocytes. For example, the cell surface molecule can be antigen CD2, CD3, CD16, CD64, CD89; NKp30, NKp44, NKp46, NKp80 (KLR-F1), NKG2C or NKG2D.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

Also disclosed is a pharmaceutical composition comprising a molecule disclosed herein in a pharmaceutically acceptable carrier. Also disclosed is a method for treating cancer in a subject that involves administering to the subject a therapeutically effective amount of a disclosed pharmaceutical composition. In some cases, the cancer can be any CLEC12A-expressing malignancy. In some cases, the cancer comprises a myelodysplastic syndrome, acute myeloid leukemia, or bi-phenotypic leukemia.

Also disclosed are chimeric antigen receptor (CAR) polypeptides that can be used with adoptive cell transfer to target and kill CLEC12A-expressing cancers. The disclosed CAR polypeptides contain in an ectodomain an anti-CLEC12A binding agent that can bind CLEC12A-expressing cancer cells. Also disclosed is an immune effector cell genetically modified to express the disclosed CAR polypeptide.

The anti-CLEC12A binding agent is in some embodiments an antibody fragment that specifically binds CLEC12A. For example, the antigen binding domain can be a Fab or a single-chain variable fragment (scFv) of an antibody that specifically binds CLEC12A. The anti-CLEC12A binding agent is in some embodiments an aptamer that specifically binds CLEC12A. For example, the anti-CLEC12A binding agent can be a peptide aptamer selected from a random sequence pool based on its ability to bind CLEC12A. The anti-CLEC12A binding agent can also be a natural ligand of CLEC12A, or a variant and/or fragment thereof capable of binding CLEC12A.

In some embodiments, the anti-CLEC12A region of the disclosed antibody or CAR is derived from hybridoma 1F3, 1F8, 1G3, 2A10, 3F12, 4E3, 4E10, 5B2, 5F10, 6C7, 9A2, 11C7, 11H1, 12D6, or combinations thereof. In some embodiments, the anti-CLEC12A region (e.g. scFv) can comprise a variable heavy ($V_H$) domain having CDR1, CDR2 and CDR3 sequences and a variable light ($V_L$) domain having CDR1, CDR2 and CDR3 sequences.

In some embodiments, the CDR1 sequence of the $V_H$ domain comprises the amino acid sequence GFTFSSFA (SEQ ID NO:1) SFAVS (SEQ ID NO:2), or SHDMS (SEQ ID NO:3); the CDR2 sequence of the $V_H$ domain comprises the amino acid sequence ISSGGAYT (SEQ ID NO:4) or TISSGGAYTFYKDSVKGRFT (SEQ ID NO:5), or YIS-GGGTNIYYSDTVKGRFT (SEQ ID NO:6); the CDR3 sequence of the $V_H$ domain comprises the amino acid sequence ARHSGYDGYYLYAMDY (SEQ ID NO:7), HSGYDGYYLYAMDY (SEQ ID NO:8), or PNYNYGGSWFAY (SEQ ID NO: 9); the CDR1 sequence of the $V_L$ comprises the amino acid sequence SSVHY (SEQ ID NO:10), ASSSVHYMH (SEQ ID NO:11), or SASSSVHYMH (SEQ ID NO:12); the CDR2 sequence of the $V_L$ domain comprises the amino acid sequence DTSX (SEQ ID NO:13) or DTSKLAS (SEQ ID NO:14); and the CDR3 sequence of the $V_L$ domain comprises the amino acid sequence QQWTSNPPT (SEQ ID NO:15).

In some embodiments, the anti-CLEC12A $V_H$ domain comprises the amino acid sequence

```
                                      (SEQ ID NO: 16, 1F3H8)
ELILVESGGGLVKPGGSLKLSCAVSGFTFSSFAMSWVRQTPEKRLEWVAT

ISSGGAYTFYKDSVKGRFTISRDNAKNTLYLQMSSLRSEDSAMYYCARHS

GYDGYYLYAMDYWGQGTSVTVSS.
```

Therefore, in some embodiments, the anti-CLEC12A $V_H$ domain is encoded by the nucleic acid sequence

```
                                      (SEQ ID NO: 17, 1F3H8)
GAACTAATACTGGTGGAGTCTGGGGGAGGCTTAGTGAAGCCTGGAGGGTC

CCTGAAACTCTCCTGTGCAGTCTCTGGATTCACTTTCAGTTCCTTTGCCA

TGTCTTGGGTTCGCCAGACTCCGGAGAAGAGGCTGGAGTGGGTCGCAACC

ATTAGTAGTGGTGGAGCTTACACCTTCTATAAAGACAGTGTGAAGGGGCG

ATTCACCATCTCCAGAGACAATGCCAAGAATACCCTGTACCTGCAAATGA

GCAGTCTGAGGTCTGAGGACTCGGCCATGTATTACTGTGCAAGACATAGC

GGCTATGATGGTTACTACCTCTATGCTATGGACTACTGGGGTCAAGGAAC

CTCAGTCACCGTCTCCTCA.
```

In some embodiments, the anti-CLEC12A $V_H$ domain comprises the amino acid sequence

```
                                      (SEQ ID NO: 18, 1F3A10)
GVQCELILVESGGGLVKPGGSLKLSCAVSGFTFSSFAVSWVRQTPEKRLE

WVATISSGGAYTFYKDSVKGRFTISRDNAKNTLYLQMSSLRSEDSAMYYC

ARHSGYDGYYLYAMDYWGQGTSVTVSS.
```

Therefore, in some embodiments, the anti-CLEC12A $V_H$ domain is encoded by the nucleic acid sequence

```
                                      (SEQ ID NO: 19, 1F3A10)
GGTGTCCAGTGTGAACTAATACTGGTGGAGTCTGGGGGAGGCTTAGTGAA

GCCTGGAGGGTCCCTGAAACTCTCCTGTGCAGTCTCTGGATTCACTTTCA

GTTCCTTTGCCGTGTCCTGGGTTCGCCAGACTCCGGAGAAGAGGCTGGAG

TGGGTCGCAACCATTAGTAGTGGTGGAGCTTACACCTTCTATAAAGACAG

TGTGAAGGGGCGATTCACCATCTCCAGAGACAATGCCAAGAATACCCTGT

ACCTGCAAATGAGCAGTCTGAGGTCTGAGGACTCGGCCATGTATTACTGT

GCAAGACATAGCGGCTATGATGGTTACTACCTCTATGCTATGGACTACTG

GGGTCAAGGAACCTCAGTCACCGTCTCCTCA.
```

In some embodiments, the anti-CLEC12A $V_H$ domain comprises the amino acid sequence

```
                                      (SEQ ID NO: 20, 1F3F3)
EVQLEESGGGLVQPGGSLKVSCAVSGLAFSSHDMSWVRQTPEKRLEWVAY

ISGGGTNIYYSDTVKGRFTISRDNAKNTLYLQMSSLKSEDTAIYYCARPN

YNYGGSWFAYWGQGTLVTVSA.
```

Therefore, in some embodiments, the anti-CLEC12A $V_H$ domain is encoded by the nucleic acid sequence

```
                                      (SEQ ID NO: 21, 1F3F3)
GAGGTGCAGCTGGAGGAGTCTGGGGGAGGCTTAGTGCAGCCGGGAGGGTC

CCTGAAAGTCTCCTGTGCAGTTTCCGGACTCGCTTTCAGCAGCCATGACA

TGTCTTGGGTTCGCCAGACTCCGGAGAAGCGGCTGGAGTGGGTCGCATAC

ATTAGTGGAGGTGGTACTAATATCTATTATTCAGACACTGTGAAGGGCCG

ATTCACCATCTCCAGAGACAATGCCAAGAACACCCTGTACCTGCAAATGA

GCAGTCTGAAGTCTGAAGACACAGCCATTTATTACTGTGCAAGACCCAAT

TATAATTACGGCGGTTCCTGGTTTGCTTACTGGGGCCAAGGGACTCTGGT

CACTGTCTCTGCA.
```

In some embodiments, the anti-CLEC12A $V_L$ domain comprises the amino acid sequence

```
                                 (SEQ ID NO: 22, 1F3H8, 1F3F3, 1F3A10)
QIVLTQSPEIMSASPGEKVTMTCSASSSVHYMHWYQQKSGTSPKRWIYDT

SKLASGVPGRFSGSGSGTSYSLTISSMESEDAATYYCQQWTSNPPTFGGG

TKLEIK.
```

Therefore, in some embodiments, the anti-CLEC12A $V_L$ domain is encoded by the nucleic acid sequence

```
                                 (SEQ ID NO: 23, 1F3H8, 1F3F3, 1F3A10)
CAAATTGTTCTCACCCAGTCTCCAGAAATCATGTCTGCATCTCCAGGGGA

GAAGGTCACCATGACCTGCAGTGCCAGCTCAAGTGTACATTACATGCACT

GGTACCAGCAGAAGTCAGGCACCTCCCCCAAAAGATGGATTTATGACACA

TCCAAACTGGCTTCTGGAGTCCCTGGTCGCTTCAGTGGCAGTGGGTCTGG

GACCTCTTACTCTCTCACAATCAGCAGCATGGAGTCTGAAGATGCTGCCA

CTTATTACTGCCAGCAGTGGACTAGTAACCCACCCACGTTCGGAGGGGGG

ACCAAGCTGGAAATTAAACG.
```

The heavy and light chains are preferably separated by a linker. Suitable linkers for scFv antibodies are known in the art. In some embodiments, the linker comprises the amino acid sequence GGGGSGGGGSGGGGS (SEQ ID NO:24). The scFv can have the formula $NH_3$-$V_H$-linker-$V_L$-COOH or $NH_3$-$V_L$-linker-$V_H$-COOH.

In some embodiments, the anti-CLEC12A scFv comprises an amino acid sequence:

```
                                      (SEQ ID NO: 25, 1F3H8)
ELILVESGGGLVKPGGSLKLSCAVSGFTFSSFAMSWVRQTPEKRLEWVAT

ISSGGAYTFYKDSVKGRFTISRDNAKNTLYLQMSSLRSEDSAMYYCARHS
```

GYDGYYLYAMDYWGQGTSVTVSSGGGGSGGGGSGGGGSQIVLTQSPEIMS

ASPGEKVTMTCSASSSVHYMHWYQQKSGTSPKRWIYDTSKLASGVPGRFS

GSGSGTSYSLTISSMESEDAATYYCQQWTSNPPTFGGGTKLEIK.

In some embodiments, the anti-CLEC12A scFv comprises an amino acid sequence:

(SEQ ID NO: 26, 1F3A10)
GVQCELILVESGGGLVKPGGSLKLSCAVSGFTFSSFAVSWVRQTPEKRLE

WVATISSGGAYTFYKDSVKGRFTISRDNAKNTLYLQMSSLRSEDSAMYYC

ARHSGYDGYYLYAMDYWGQGTSVTVSSGGGGSGGGGSGGGGSQIVLTQSP

EIMSASPGEKVTMTCSASSSVHYMHWYQQKSGTSPKRWIYDTSKLASGVP

GRFSGSGSGTSYSLTISSMESEDAATYYCQQWTSNPPTFGGGTKLEIK.

In some embodiments, the anti-CLEC12A scFv comprises an amino acid sequence:

(SEQ ID NO: 27, 1F3F3)
EVQLEESGGGLVQPGGSLKVSCAVSGLAFSSHDMSVWRQTPEKRLEWVAY

ISGGGTNIYYSDTVKGRFTISRDNAKNTLYLQMSSLKSEDTAIYYCARPN

YNYGGSWFAYWGQGTLVTVSAGGGGSGGGGSGGGGSQIVLTQSPEIMSAS

PGEKVTMTCSASSSVHYMHWYQQKSGTSPKRWIYDTSKLASGVPGRFSGS

GSGTSYSLTISSMESEDAATYYCQQWTSNPPTFGGGTKLEIK.

In some embodiments, the anti-CLEC12A scFv comprises an amino acid sequence:

(SEQ ID NO: 28)
QIVLTQSPEIMSASPGEKVTMTCSASSSVHYMHWYQQKSGTSPKRWIYDT

SKLASGVPGRFSGSGSGTSYSLTISSMESEDAATYYCQQWTSNPPTFGGG

TKLEIKGGGGSGGGGSGGGGSELILVESGGGLVKPGGSLKLSCAVSGFTF

SSFAMSWVRQTPEKRLEWVATISSGGAYTFYKDSVKGRFTISRDNAKNTL

YLQMSSLRSEDSAMYYCARHSGYDGYYLYAMDYWGQGTSVTVSS.

In some embodiments, the anti-CLEC12A scFv comprises an amino acid sequence:

(SEQ ID NO: 29)
QIVLTQSPEIMSASPGEKVTMTCSASSSVHYMHWYQQKSGTSPKRWIYDT

SKLASGVPGRFSGSGSGTSYSLTISSMESEDAATYYCQQWTSNPPTFGGG

TKLEIKGGGGSGGGGSGGGGSGVQCELILVESGGGLVKPGGSLKLSCAVS

GFTFSSFAVSWVRQTPEKRLEWVATISSGGAYTFYKDSVKGRFTISRDN

AKNTLYLQMSSLRSEDSAMYYCARHSGYDGYYLYAMDYWGQGTSVTVSS.

In some embodiments, the anti-CLEC12A scFv comprises an amino acid sequence:

(SEQ ID NO: 30)
QIVLTQSPEIMSASPGEKVTMTCSASSSVHYMHWYQQKSGTSPKRWIYDT

SKLASGVPGRFSGSGSGTSYSLTISSMESEDAATYYCQQWTSNPPTFGGG

TKLEIKGGGGSGGGGSGGGGSEVQLEESGGGLVQPGGSLKVSCAVSGLAF

SSHDMSWVRQTPEKRLEWVAYISGGGTNIYYSDTVKGRFTISRDNAKNT

LYLQMSSLKSEDTAIYYCARPNYNYGGSWFAYWGQGTLVTVSA.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination thereof, but does not contain a CD3 zeta (CD3ζ) signaling domain (SD).

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to CLEC12A.

Also disclosed is a method of providing an anti-tumor immunity in a subject with a CLEC12A-expressing cancer that involves administering to the subject an effective amount of an immune effector cell genetically modified with a disclosed CLEC12A-specific CAR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A to 2I show immunephenotype of anti-CLEC12A CARs. Healthy T cells isolated from PBMCs were transduced with anti-CLEC12A CARs. Following 1-week of culturing without antigen stimulation, cells were stained for CD3, CD4, CD8, PD1, CCR7, and CD45RA, and data were collected on a flow cytometer. Transduction efficiency was determined based on mCherry expression (FIGS. 2A and 2B). Live, CAR positive T cells were analyzed for CD4, CD8, and PD1 expression (FIGS. 2C-2H). T cells subsets were also analyzed based on CCR7 and CD45RA expression (FIG. 2I). EFF=effector, EM=effector memory, CM=central memory, N=Naïve.

FIGS. 3A to 3F show CD4 and CD8 immunephenotype of anti-CLEC12A CARs. CD4 and CD8 T cells were analyzed for expression of PD1 (FIGS. 3A & 3B, 3D & 3E) and for T cells subsets (FIGS. 3C & 3F). EFF=effector, EM=effector memory, CM=central memory, N=Naïve.

DETAILED DESCRIPTION

Figures 1A, 1B:
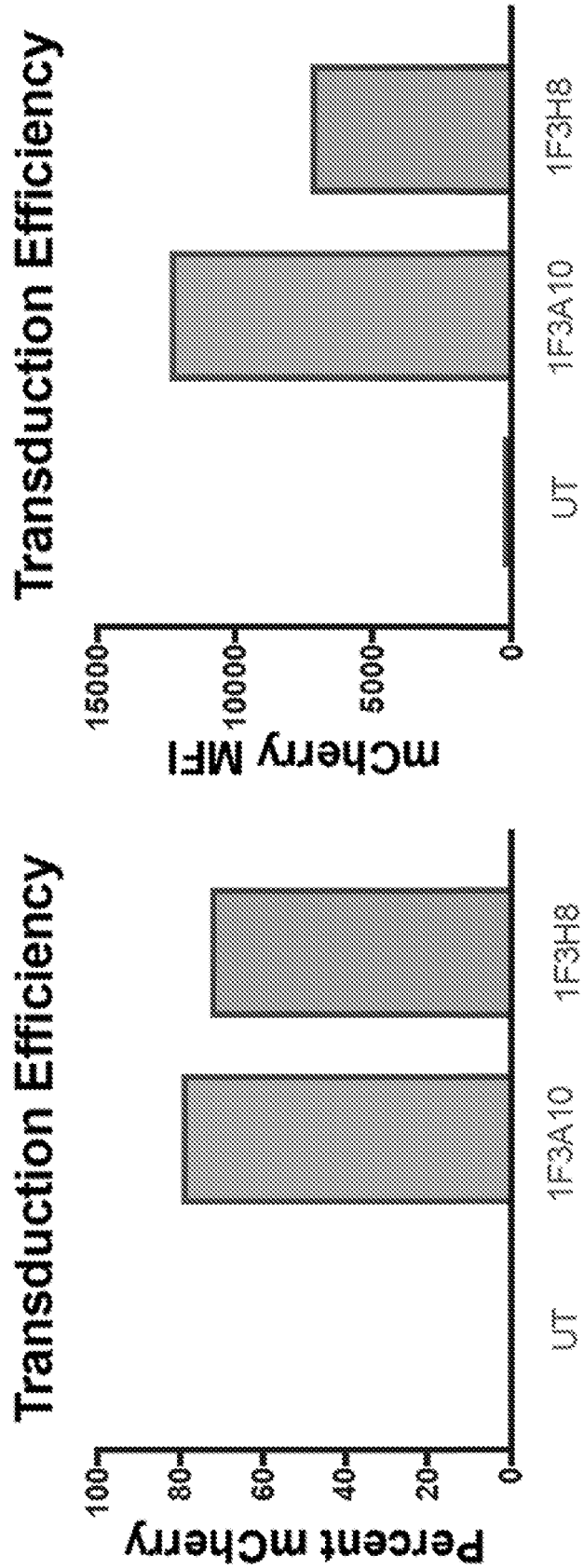
FIGS. 1A to 1D shows CHO cells overexpressing CLEC12A (CHO-CLEC12A) were used as target cells. Gammaretroviruses expressing anti-CLEC12A CARs were transduced into primary T cells isolated from healthy PBMCs. Transduction efficiency of each CAR was determined by flow cytometric analysis of mCherry expression (FIGS. 1A and 1B). CAR positive cells were added to target cells at effector to target ratios of either 1:1 (FIG. 1C) or 1:5 (FIG. 1D). UT=Untransduced, MFI=median fluorescent intensity.
Figure 1C:
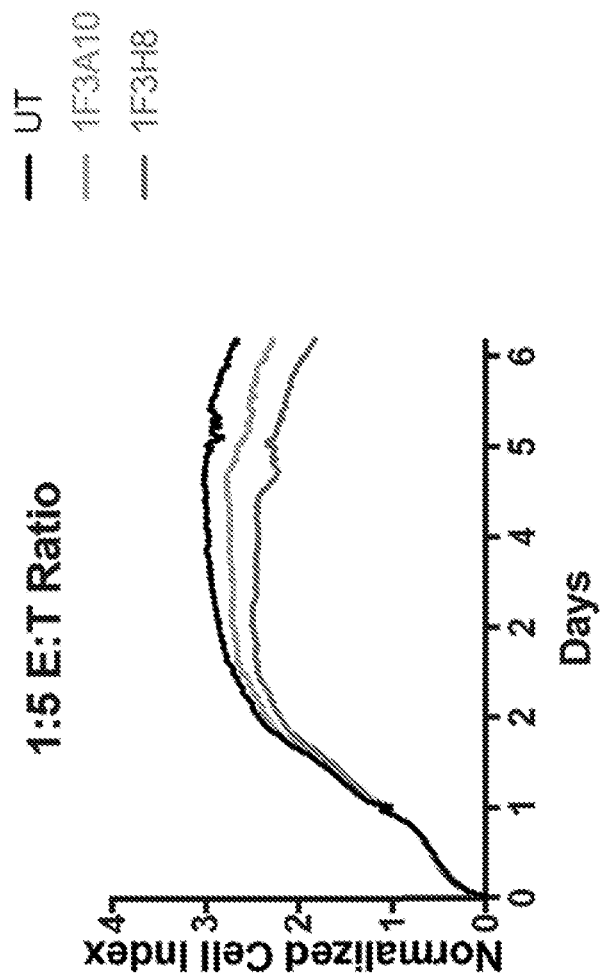

Disclosed herein are bispecific antibodies and chimeric antigen receptors (CAR), that can specifically recognize tumor-associated antigens (TAA) on CLEC12A-expressing cancers. Also disclosed are immune effector cells, such as T cells or Natural Killer (NK) cells, that are engineered to express these CARs. Therefore, also disclosed are methods for providing an anti-tumor immunity in a subject with CLEC12A-expressing cancers using the disclosed antibodies and immune effector cells.

Antibodies

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A bi-specific antibody designed to selectively bind CD3 and CLEC12A would trigger non-specific T-cell activation & cytokine storm. A bi-specific diabody designed to selectively bind CD3 and CLEC12A would have a molecular weight (55-60 kD) less than the renal clearance threshold, which would result in rapid elimination. As such, diabodies must be administered by a continuous infusion. The disclosed tetravalent, bi-specific antibody can have a molecular weight (e.g., 105-110 kD) greater than the renal filtration threshold with markedly extended PK.

Provided are fusion polypeptides capable of forming a multivalent engineered antibody that is able to engage T-cells to destroy CLEC12A-expressing malignant cells. The engineered antibody may comprise for example, at least one scFv, at least one Fab fragment, at least one Fv fragment, etc. It may be bivalent, trivalent, tetravalent, etc. The multivalent antibodies is multispecific, e.g., bispecific, trispecific, tetraspecific, etc. The multivalent antibodies may be in any form, such as a diabody, triabody, tetrabody, etc.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bi-specific antibodies, which are obtained by the noncovalent association of two single-chain fusion products, consisting of the VH domain from one antibody connected by a short linker to the VL domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein. Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest (e.g., CLEC12A). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

Pharmaceutical Composition

Also disclosed is a pharmaceutical composition comprising a disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, PA 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid—or base—addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed is a method for treating a CLEC12A-expressing cancer in a subject by administering to the subject a therapeutically effective amount of the disclosed pharmaceutical composition. The method can further involve administering to the subject a chemotherapy such as fludarabine, cytarabine, cyclophosphamide, idarubicin, daunorubicin, or a targeted inhibitor such as imbruvica, midostaurin, idelalisib, or an immune agents such as PD1 or PDL1 inhibitors.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a CLEC12A-expressing cancer. Thus, the method can further comprise identifying a subject at risk for a CLEC12A-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

CLEC12A-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a CLEC12A-specific chimeric antigen receptor (CAR) that can be that can be expressed in immune effector cells to enhance antitumor activity against CLEC12A-specific CARs.

The disclosed CAR is generally made up of three domains: an ectodomain, a transmembrane domain, and an endodomain. The ectodomain comprises the CLEC12A-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain a signaling domain (ISD) and a co-stimulatory signaling region (CSR).

A "signaling domain (SD)" generally contains immunoreceptor tyrosine-based activation motifs (ITAMs) that activate a signaling cascade when the ITAM is phosphorylated.

The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-CLEC12A-HG-TM-CSR-SD; or

SP-CLEC12A-HG-TM-SD-CSR;

wherein "SP" represents an optional signal peptide,
wherein "CLEC12A" represents a CLEC12A-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3 domain. TanCAR T cell activation is achieved only when target cells co-express both targets.

A dual CAR T cell expresses two separate CARs with different ligand binding targets; one CAR includes only the CD3 domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank acc no. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS)

to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3 signaling domain by itself or combined with any other desired cytoplasmic domain(s) useful in the context of the CAR of the invention. For example, the cytoplasmic domain of the CAR can comprise a CD3 chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CLEC12A scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of CLEC12A-binding region, co-stimulatory signaling regions, and intracellular signaling domain that can occur in the disclosed CARs.

TABLE 1

First Generation CARs

| ScFv | Signal Domain |
|---|---|
| CLEC12A | CD8 |
| CLEC12A | CD3ζ |
| CLEC12A | CD3δ |
| CLEC12A | CD3γ |
| CLEC12A | CD3ε |
| CLEC12A | FcγRI-γ |
| CLEC12A | FcγRIII-γ |
| CLEC12A | FcεRIβ |
| CLEC12A | FcεRIγ |
| CLEC12A | DAP10 |
| CLEC12A | DAP12 |
| CLEC12A | CD32 |
| CLEC12A | CD79a |

TABLE 2

Second Generation CARs

| ScFv | Co-stimulatory Signal | Signal Domain | ScFv | Co-stimulatory Signal | Signal Domain |
|---|---|---|---|---|---|
| CLEC12A | CD28 | CD8 | CLEC12A | CD80 | FcεRIβ |
| CLEC12A | CD28 | CD3ζ | CLEC12A | CD80 | FcεRIγ |
| CLEC12A | CD28 | CD3δ | CLEC12A | CD80 | DAP10 |
| CLEC12A | CD28 | CD3γ | CLEC12A | CD80 | DAP12 |
| CLEC12A | CD28 | CD3ε | CLEC12A | CD80 | CD32 |
| CLEC12A | CD28 | FcγRI-γ | CLEC12A | CD80 | CD79a |

TABLE 2-continued

Second Generation CARs

| ScFv | Co-stimulatory Signal | Signal Domain | ScFv | Co-stimulatory Signal | Signal Domain |
|---|---|---|---|---|---|
| CLEC12A | CD28 | FcγRIII-γ | CLEC12A | CD80 | CD79b |
| CLEC12A | CD28 | FcεRIβ | CLEC12A | CD86 | CD8 |
| CLEC12A | CD28 | FcεRIγ | CLEC12A | CD86 | CD3ζ |
| CLEC12A | CD28 | DAP10 | CLEC12A | CD86 | CD3δ |
| CLEC12A | CD28 | DAP12 | CLEC12A | CD86 | CD3γ |
| CLEC12A | CD28 | CD32 | CLEC12A | CD86 | CD3ε |
| CLEC12A | CD28 | CD79a | CLEC12A | CD86 | FcγRI-γ |
| CLEC12A | CD28 | CD79b | CLEC12A | CD86 | FcγRIII-γ |
| CLEC12A | CD8 | CD8 | CLEC12A | CD86 | FcεRIβ |
| CLEC12A | CD8 | CD3ζ | CLEC12A | CD86 | FcεRIγ |
| CLEC12A | CD8 | CD3δ | CLEC12A | CD86 | DAP10 |
| CLEC12A | CD8 | CD3γ | CLEC12A | CD86 | DAP12 |
| CLEC12A | CD8 | CD3ε | CLEC12A | CD86 | CD32 |
| CLEC12A | CD8 | FcγRI-γ | CLEC12A | CD86 | CD79a |
| CLEC12A | CD8 | FcγRIII-γ | CLEC12A | CD86 | CD79b |
| CLEC12A | CD8 | FcεRIβ | CLEC12A | OX40 | CD8 |
| CLEC12A | CD8 | FcεRIγ | CLEC12A | OX40 | CD3ζ |
| CLEC12A | CD8 | DAP10 | CLEC12A | OX40 | CD3δ |
| CLEC12A | CD8 | DAP12 | CLEC12A | OX40 | CD3γ |
| CLEC12A | CD8 | CD32 | CLEC12A | OX40 | CD3ε |
| CLEC12A | CD8 | CD79a | CLEC12A | OX40 | FcγRI-γ |
| CLEC12A | CD8 | CD79b | CLEC12A | OX40 | FcγRIII-γ |
| CLEC12A | CD4 | CD8 | CLEC12A | OX40 | FcεRIβ |
| CLEC12A | CD4 | CD3ζ | CLEC12A | OX40 | FcεRIγ |
| CLEC12A | CD4 | CD3δ | CLEC12A | OX40 | DAP10 |
| CLEC12A | CD4 | CD3γ | CLEC12A | OX40 | DAP12 |
| CLEC12A | CD4 | CD3ε | CLEC12A | OX40 | CD32 |
| CLEC12A | CD4 | FcγRI-γ | CLEC12A | OX40 | CD79a |
| CLEC12A | CD4 | FcγRIII-γ | CLEC12A | OX40 | CD79b |
| CLEC12A | CD4 | FcεRIβ | CLEC12A | DAP10 | CD8 |
| CLEC12A | CD4 | FcεRIγ | CLEC12A | DAP10 | CD3ζ |
| CLEC12A | CD4 | DAP10 | CLEC12A | DAP10 | CD3δ |
| CLEC12A | CD4 | DAP12 | CLEC12A | DAP10 | CD3γ |
| CLEC12A | CD4 | CD32 | CLEC12A | DAP10 | CD3ε |
| CLEC12A | CD4 | CD79a | CLEC12A | DAP10 | FcγRI-γ |
| CLEC12A | CD4 | CD79b | CLEC12A | DAP10 | FcγRIII-γ |
| CLEC12A | b2c | CD8 | CLEC12A | DAP10 | FcεRIβ |
| CLEC12A | b2c | CD3ζ | CLEC12A | DAP10 | FcεRIγ |
| CLEC12A | b2c | CD3δ | CLEC12A | DAP10 | DAP10 |
| CLEC12A | b2c | CD3γ | CLEC12A | DAP10 | DAP12 |
| CLEC12A | b2c | CD3ε | CLEC12A | DAP10 | CD32 |
| CLEC12A | b2c | FcγRI-γ | CLEC12A | DAP10 | CD79a |
| CLEC12A | b2c | FcγRIII-γ | CLEC12A | DAP10 | CD79b |
| CLEC12A | b2c | FcεRIβ | CLEC12A | DAP12 | CD8 |
| CLEC12A | b2c | FcεRIγ | CLEC12A | DAP12 | CD3ζ |
| CLEC12A | b2c | DAP10 | CLEC12A | DAP12 | CD3δ |
| CLEC12A | b2c | DAP12 | CLEC12A | DAP12 | CD3γ |
| CLEC12A | b2c | CD32 | CLEC12A | DAP12 | CD3ε |
| CLEC12A | b2c | CD79a | CLEC12A | DAP12 | FcγRI-γ |
| CLEC12A | b2c | CD79b | CLEC12A | DAP12 | FcγRIII-γ |
| CLEC12A | CD137/41BB | CD8 | CLEC12A | DAP12 | FcεRIβ |
| CLEC12A | CD137/41BB | CD3ζ | CLEC12A | DAP12 | FcεRIγ |
| CLEC12A | CD137/41BB | CD3δ | CLEC12A | DAP12 | DAP10 |
| CLEC12A | CD137/41BB | CD3γ | CLEC12A | DAP12 | DAP12 |
| CLEC12A | CD137/41BB | CD3ε | CLEC12A | DAP12 | CD32 |
| CLEC12A | CD137/41BB | FcγRI-γ | CLEC12A | DAP12 | CD79a |
| CLEC12A | CD137/41BB | FcγRIII-γ | CLEC12A | DAP12 | CD79b |
| CLEC12A | CD137/41BB | FcεRIβ | CLEC12A | MyD88 | CD8 |
| CLEC12A | CD137/41BB | FcεRIγ | CLEC12A | MyD88 | CD3ζ |
| CLEC12A | CD137/41BB | DAP10 | CLEC12A | MyD88 | CD3δ |
| CLEC12A | CD137/41BB | DAP12 | CLEC12A | MyD88 | CD3γ |
| CLEC12A | CD137/41BB | CD32 | CLEC12A | MyD88 | CD3ε |
| CLEC12A | CD137/41BB | CD79a | CLEC12A | MyD88 | FcγRI-γ |
| CLEC12A | CD137/41BB | CD79b | CLEC12A | MyD88 | FcγRIII-γ |
| CLEC12A | ICOS | CD8 | CLEC12A | MyD88 | FcεRIβ |
| CLEC12A | ICOS | CD3ζ | CLEC12A | MyD88 | FcεRIγ |
| CLEC12A | ICOS | CD3δ | CLEC12A | MyD88 | DAP10 |
| CLEC12A | ICOS | CD3γ | CLEC12A | MyD88 | DAP12 |
| CLEC12A | ICOS | CD3ε | CLEC12A | MyD88 | CD32 |
| CLEC12A | ICOS | FcγRI-γ | CLEC12A | MyD88 | CD79a |
| CLEC12A | ICOS | FcγRIII-γ | CLEC12A | MyD88 | CD79b |
| CLEC12A | ICOS | FcγRIβ | CLEC12A | CD7 | CD8 |
| CLEC12A | ICOS | FcεRIγ | CLEC12A | CD7 | CD3ζ |
| CLEC12A | ICOS | DAP10 | CLEC12A | CD7 | CD3δ |
| CLEC12A | ICOS | DAP12 | CLEC12A | CD7 | CD3γ |

TABLE 2-continued

Second Generation CARs

| ScFv | Co-stimulatory Signal | Signal Domain | ScFv | Co-stimulatory Signal | Signal Domain |
|---|---|---|---|---|---|
| CLEC12A | ICOS | CD32 | CLEC12A | CD7 | CD3ε |
| CLEC12A | ICOS | CD79a | CLEC12A | CD7 | FcγRI-γ |
| CLEC12A | ICOS | CD79b | CLEC12A | CD7 | FcγRIII-γ |
| CLEC12A | CD27 | CD8 | CLEC12A | CD7 | FcεRIβ |
| CLEC12A | CD27 | CD3ζ | CLEC12A | CD7 | FcεRIγ |
| CLEC12A | CD27 | CD3δ | CLEC12A | CD7 | DAP10 |
| CLEC12A | CD27 | CD3γ | CLEC12A | CD7 | DAP12 |
| CLEC12A | CD27 | CD3ε | CLEC12A | CD7 | CD32 |
| CLEC12A | CD27 | FcγRI-γ | CLEC12A | CD7 | CD79a |
| CLEC12A | CD27 | FcγRIII-γ | CLEC12A | CD7 | CD79b |
| CLEC12A | CD27 | FcεRIβ | CLEC12A | BTNL3 | CD8 |
| CLEC12A | CD27 | FcεRIγ | CLEC12A | BTNL3 | CD3ζ |
| CLEC12A | CD27 | DAP10 | CLEC12A | BTNL3 | CD3δ |
| CLEC12A | CD27 | DAP12 | CLEC12A | BTNL3 | CD3γ |
| CLEC12A | CD27 | CD32 | CLEC12A | BTNL3 | CD3ε |
| CLEC12A | CD27 | CD79a | CLEC12A | BTNL3 | FcγRI-γ |
| CLEC12A | CD27 | CD79b | CLEC12A | BTNL3 | FcγRIII-γ |
| CLEC12A | CD28δ | CD8 | CLEC12A | BTNL3 | FcεRIβ |
| CLEC12A | CD28δ | CD3ζ | CLEC12A | BTNL3 | FcεRIγ |
| CLEC12A | CD28δ | CD3δ | CLEC12A | BTNL3 | DAP10 |
| CLEC12A | CD28δ | CD3γ | CLEC12A | BTNL3 | DAP12 |
| CLEC12A | CD28δ | CD3ε | CLEC12A | BTNL3 | CD32 |
| CLEC12A | CD28δ | FcγRI-γ | CLEC12A | BTNL3 | CD79a |
| CLEC12A | CD28δ | FcγRIII-γ | CLEC12A | BTNL3 | CD79b |
| CLEC12A | CD28δ | FcεRIβ | CLEC12A | NKG2D | CD8 |
| CLEC12A | CD28δ | FcεRIγ | CLEC12A | NKG2D | CD3ζ |
| CLEC12A | CD28δ | DAP10 | CLEC12A | NKG2D | CD3δ |
| CLEC12A | CD28δ | DAP12 | CLEC12A | NKG2D | CD3γ |
| CLEC12A | CD28δ | CD32 | CLEC12A | NKG2D | CD3ε |
| CLEC12A | CD28δ | CD79a | CLEC12A | NKG2D | FcγRI-γ |
| CLEC12A | CD28δ | CD79b | CLEC12A | NKG2D | FcγRIII-γ |
| CLEC12A | CD80 | CD8 | CLEC12A | NKG2D | FcεRIβ |
| CLEC12A | CD80 | CD3ζ | CLEC12A | NKG2D | FcεRIγ |
| CLEC12A | CD80 | CD3δ | CLEC12A | NKG2D | DAP10 |
| CLEC12A | CD80 | CD3γ | CLEC12A | NKG2D | DAP12 |
| CLEC12A | CD80 | CD3ε | CLEC12A | NKG2D | CD32 |
| CLEC12A | CD80 | FcγRI-γ | CLEC12A | NKG2D | CD79a |
| CLEC12A | CD80 | FcγRIII-γ | CLEC12A | NKG2D | CD79b |

TABLE 3

Third Generation CARs

| ScFv | Co-stimulatory Signal | Co-stimulatory Signal | Signal Domain | ScFv | Co-stimulatory Signal | Co-stimulatory Signal | Signal Domain |
|---|---|---|---|---|---|---|---|
| CLEC12A | CD28 | CD28 | CD8 | CLEC12A | CD28 | CD8 | CD79a |
| CLEC12A | CD28 | CD28 | CD3ζ | CLEC12A | CD28 | CD8 | CD79b |
| CLEC12A | CD28 | CD28 | CD3δ | CLEC12A | CD28 | CD4 | CD8 |
| CLEC12A | CD28 | CD28 | CD3γ | CLEC12A | CD28 | CD4 | CD3ζ |
| CLEC12A | CD28 | CD28 | CD3ε | CLEC12A | CD28 | CD4 | CD3δ |
| CLEC12A | CD28 | CD28 | FcγRI-γ | CLEC12A | CD28 | CD4 | CD3γ |
| CLEC12A | CD28 | CD28 | FcγRIII-γ | CLEC12A | CD28 | CD4 | CD3ε |
| CLEC12A | CD28 | CD28 | FcεRIβ | CLEC12A | CD28 | CD4 | FcγRI-γ |
| CLEC12A | CD28 | CD28 | FcεRIγ | CLEC12A | CD28 | CD4 | FcγRIII-γ |
| CLEC12A | CD28 | CD28 | DAP10 | CLEC12A | CD28 | CD4 | FcεRIβ |
| CLEC12A | CD28 | CD28 | DAP12 | CLEC12A | CD28 | CD4 | FcεRIγ |
| CLEC12A | CD28 | CD28 | CD32 | CLEC12A | CD28 | CD4 | DAP10 |
| CLEC12A | CD28 | CD28 | CD79a | CLEC12A | CD28 | CD4 | DAP12 |
| CLEC12A | CD28 | CD28 | CD79b | CLEC12A | CD28 | CD4 | CD32 |
| CLEC12A | CD28 | CD8 | CD8 | CLEC12A | CD28 | CD4 | CD79a |
| CLEC12A | CD28 | CD8 | CD3ζ | CLEC12A | CD28 | CD4 | CD79b |
| CLEC12A | CD28 | CD8 | CD3δ | CLEC12A | CD28 | b2c | CD8 |
| CLEC12A | CD28 | CD8 | CD3γ | CLEC12A | CD28 | b2c | CD3ζ |
| CLEC12A | CD28 | CD8 | CD3ε | CLEC12A | CD28 | b2c | CD3δ |
| CLEC12A | CD28 | CD8 | FcγRI-γ | CLEC12A | CD28 | b2c | CD3γ |
| CLEC12A | CD28 | CD8 | FcγRIII-γ | CLEC12A | CD28 | b2c | CD3ε |
| CLEC12A | CD28 | CD8 | FcεRIβ | CLEC12A | CD28 | b2c | FcγRI-γ |
| CLEC12A | CD28 | CD8 | FcεRIγ | CLEC12A | CD28 | b2c | FcγRIII-γ |
| CLEC12A | CD28 | CD8 | DAP10 | CLEC12A | CD28 | b2c | FcεRIβ |
| CLEC12A | CD28 | CD8 | DAP12 | CLEC12A | CD28 | b2c | FcεRIγ |
| CLEC12A | CD28 | CD8 | CD32 | CLEC12A | CD28 | b2c | DAP10 |

TABLE 3-continued

Third Generation CARs

| ScFv | Co-stimulatory Signal | Co-stimulatory Signal | Signal Domain |
|---|---|---|---|
| CLEC12A | CD28 | b2c | DAP12 |
| CLEC12A | CD28 | b2c | CD32 |
| CLEC12A | CD28 | b2c | CD79a |
| CLEC12A | CD28 | b2c | CD79b |
| CLEC12A | CD28 | CD137/41BB | CD8 |
| CLEC12A | CD28 | CD137/41BB | CD3ζ |
| CLEC12A | CD28 | CD137/41BB | CD3δ |
| CLEC12A | CD28 | CD137/41BB | CD3γ |
| CLEC12A | CD28 | CD137/41BB | CD3ε |
| CLEC12A | CD28 | CD137/41BB | FcγRI-γ |
| CLEC12A | CD28 | CD137/41BB | FcγRIII-γ |
| CLEC12A | CD28 | CD137/41BB | FcεRIβ |
| CLEC12A | CD28 | CD137/41BB | FcεRIγ |
| CLEC12A | CD28 | CD137/41BB | DAP10 |
| CLEC12A | CD28 | CD137/41BB | DAP12 |
| CLEC12A | CD28 | CD137/41BB | CD32 |
| CLEC12A | CD28 | CD137/41BB | CD79a |
| CLEC12A | CD28 | CD137/41BB | CD79b |
| CLEC12A | CD28 | ICOS | CD8 |
| CLEC12A | CD28 | ICOS | CD3ζ |
| CLEC12A | CD28 | ICOS | CD3δ |
| CLEC12A | CD28 | ICOS | CD3γ |
| CLEC12A | CD28 | ICOS | CD3ε |
| CLEC12A | CD28 | ICOS | FcγRI-γ |
| CLEC12A | CD28 | ICOS | FcγRIII-γ |
| CLEC12A | CD28 | ICOS | FcεRIβ |
| CLEC12A | CD28 | ICOS | FcεRIγ |
| CLEC12A | CD28 | ICOS | DAP10 |
| CLEC12A | CD28 | ICOS | DAP12 |
| CLEC12A | CD28 | ICOS | CD32 |
| CLEC12A | CD28 | ICOS | CD79a |
| CLEC12A | CD28 | ICOS | CD79b |
| CLEC12A | CD28 | CD27 | CD8 |
| CLEC12A | CD28 | CD27 | CD3ζ |
| CLEC12A | CD28 | CD27 | CD3δ |
| CLEC12A | CD28 | CD27 | CD3γ |
| CLEC12A | CD28 | CD27 | CD3ε |
| CLEC12A | CD28 | CD27 | FcγRI-γ |
| CLEC12A | CD28 | CD27 | FcγRIII-γ |
| CLEC12A | CD28 | CD27 | FcεRIβ |
| CLEC12A | CD28 | CD27 | FcεRIγ |
| CLEC12A | CD28 | CD27 | DAP10 |
| CLEC12A | CD28 | CD27 | DAP12 |
| CLEC12A | CD28 | CD27 | CD32 |
| CLEC12A | CD28 | CD27 | CD79a |
| CLEC12A | CD28 | CD27 | CD79b |
| CLEC12A | CD28 | CD28δ | CD8 |
| CLEC12A | CD28 | CD28δ | CD3ζ |
| CLEC12A | CD28 | CD28δ | CD3δ |
| CLEC12A | CD28 | CD28δ | CD3γ |
| CLEC12A | CD28 | CD28δ | CD3ε |
| CLEC12A | CD28 | CD28δ | FcγRI-γ |
| CLEC12A | CD28 | CD28δ | FcγRIII-γ |
| CLEC12A | CD28 | CD28δ | FcεRIβ |
| CLEC12A | CD28 | CD28δ | FcεRIγ |
| CLEC12A | CD28 | CD28δ | DAP10 |
| CLEC12A | CD28 | CD28δ | DAP12 |
| CLEC12A | CD28 | CD28δ | CD32 |
| CLEC12A | CD28 | CD28δ | CD79a |
| CLEC12A | CD28 | CD28δ | CD79b |
| CLEC12A | CD28 | CD80 | CD8 |
| CLEC12A | CD28 | CD80 | CD3ζ |
| CLEC12A | CD28 | CD80 | CD3δ |
| CLEC12A | CD28 | CD80 | CD3γ |
| CLEC12A | CD28 | CD80 | CD3ε |
| CLEC12A | CD28 | CD80 | FcγRI-γ |
| CLEC12A | CD28 | CD80 | FcγRIII-γ |
| CLEC12A | CD28 | CD80 | FcεRIβ |
| CLEC12A | CD28 | CD80 | FcεRIγ |
| CLEC12A | CD28 | CD80 | DAP10 |
| CLEC12A | CD28 | CD80 | DAP12 |
| CLEC12A | CD28 | CD80 | CD32 |
| CLEC12A | CD28 | CD80 | CD79a |
| CLEC12A | CD28 | CD80 | CD79b |
| CLEC12A | CD28 | CD86 | CD8 |
| CLEC12A | CD28 | CD86 | CD3ζ |
| CLEC12A | CD28 | CD86 | CD3δ |
| CLEC12A | CD28 | CD86 | CD3γ |
| CLEC12A | CD28 | CD86 | CD3ε |
| CLEC12A | CD28 | CD86 | FcγRI-γ |
| CLEC12A | CD28 | CD86 | FcγRIII-γ |
| CLEC12A | CD28 | CD86 | FcεRIβ |
| CLEC12A | CD28 | CD86 | FcεRIγ |
| CLEC12A | CD28 | CD86 | DAP10 |
| CLEC12A | CD28 | CD86 | DAP12 |
| CLEC12A | CD28 | CD86 | CD32 |
| CLEC12A | CD28 | CD86 | CD79a |
| CLEC12A | CD28 | CD86 | CD79b |
| CLEC12A | CD28 | OX40 | CD8 |
| CLEC12A | CD28 | OX40 | CD3ζ |
| CLEC12A | CD28 | OX40 | CD3δ |
| CLEC12A | CD28 | OX40 | CD3γ |
| CLEC12A | CD28 | OX40 | CD3ε |
| CLEC12A | CD28 | OX40 | FcγRI-γ |
| CLEC12A | CD28 | OX40 | FcγRIII-γ |
| CLEC12A | CD28 | OX40 | FcεRIβ |
| CLEC12A | CD28 | OX40 | FcεRIγ |
| CLEC12A | CD28 | OX40 | DAP10 |
| CLEC12A | CD28O | OX40 | DAP12 |
| CLEC12A | OD28 | OX40 | CD32 |
| CLEC12A | CD28 | OX40 | CD79a |
| CLEC12A | CD28 | OX40 | CD79b |
| CLEC12A | CD28 | DAP10 | CD8 |
| CLEC12A | CD28 | DAP10 | CD3ζ |
| CLEC12A | CD28 | DAP10 | CD3δ |
| CLEC12A | CD28 | DAP10 | CD3γ |
| CLEC12A | CD28 | DAP10 | CD3ε |
| CLEC12A | CD28 | DAP10 | FcγRI-γ |
| CLEC12A | CD28 | DAP10 | FcγRIII-γ |
| CLEC12A | CD28 | DAP10 | FcεRIβ |
| CLEC12A | CD28 | DAP10 | FcεRIγ |
| CLEC12A | CD28 | DAP10 | DAP10 |
| CLEC12A | CD28 | DAP10 | DAP12 |
| CLEC12A | CD28 | DAP10 | CD32 |
| CLEC12A | CD28 | DAP10 | CD79a |
| CLEC12A | CD28 | DAP10 | CD79b |
| CLEC12A | CD28 | DAP12 | CD8 |
| CLEC12A | CD28 | DAP12 | CD3ζ |
| CLEC12A | CD28 | DAP12 | CD3δ |
| CLEC12A | CD28 | DAP12 | CD3γ |
| CLEC12A | CD28 | DAP12 | CD3ε |
| CLEC12A | CD28 | DAP12 | FcγRI-γ |
| CLEC12A | CD28 | DAP12 | FcγRIII-γ |
| CLEC12A | CD28 | DAP12 | FcεRIβ |
| CLEC12A | CD28 | DAP12 | FcεRIγ |
| CLEC12A | CD28 | DAP12 | DAP10 |
| CLEC12A | CD28 | DAP12 | DAP12 |
| CLEC12A | CD28 | DAP12 | CD32 |
| CLEC12A | CD28 | DAP12 | CD79a |
| CLEC12A | CD28 | DAP12 | CD79b |
| CLEC12A | CD28 | MyD88 | CD8 |
| CLEC12A | CD28 | MyD88 | CD3ζ |
| CLEC12A | CD28 | MyD88 | CD3δ |
| CLEC12A | CD28 | MyD88 | CD3γ |
| CLEC12A | CD28 | MyD88 | CD3ε |
| CLEC12A | CD28 | MyD88 | FcγRI-γ |
| CLEC12A | CD28 | MyD88 | FcγRIII-γ |
| CLEC12A | CD28 | MyD88 | FcεRIβ |
| CLEC12A | CD28 | MyD88 | FcεRIγ |
| CLEC12A | CD28 | MyD88 | DAP10 |
| CLEC12A | CD28 | MyD88 | DAP12 |
| CLEC12A | CD28 | MyD88 | CD32 |
| CLEC12A | CD28 | MyD88 | CD79a |
| CLEC12A | CD28 | MyD88 | CD79b |
| CLEC12A | CD28 | CD7 | CD8 |
| CLEC12A | CD28 | CD7 | CD3ζ |
| CLEC12A | CD28 | CD7 | CD3δ |
| CLEC12A | CD28 | CD7 | CD3γ |
| CLEC12A | CD28 | CD7 | CD3ε |
| CLEC12A | CD28 | CD7 | FcγRI-γ |

TABLE 3-continued

Third Generation CARs

| ScFv | Co-stimulatory Signal | Co-stimulatory Signal | Signal Domain |
|---|---|---|---|
| CLEC12A | CD28 | CD7 | FcγRIII-γ |
| CLEC12A | CD28 | CD7 | FcεRIβ |
| CLEC12A | CD28 | CD7 | FcεRIγ |
| CLEC12A | CD28 | CD7 | DAP10 |
| CLEC12A | CD28 | CD7 | DAP12 |
| CLEC12A | CD28 | CD7 | CD32 |
| CLEC12A | CD28 | CD7 | CD79a |
| CLEC12A | CD28 | CD7 | CD79b |
| CLEC12A | CD28 | BTNL3 | CD8 |
| CLEC12A | CD28 | BTNL3 | CD3ζ |
| CLEC12A | CD28 | BTNL3 | CD3δ |
| CLEC12A | CD28 | BTNL3 | CD3γ |
| CLEC12A | CD28 | BTNL3 | CD3ε |
| CLEC12A | CD28 | BTNL3 | FcγRI-γ |
| CLEC12A | CD28 | BTNL3 | FcγRIII-γ |
| CLEC12A | CD28 | BTNL3 | FcεRIβ |
| CLEC12A | CD28 | BTNL3 | FcεRIγ |
| CLEC12A | CD28 | BTNL3 | DAP10 |
| CLEC12A | CD28 | BTNL3 | DAP12 |
| CLEC12A | CD28 | BTNL3 | CD32 |
| CLEC12A | CD28 | BTNL3 | CD79a |
| CLEC12A | CD28 | BTNL3 | CD79b |
| CLEC12A | CD28 | NKG2D | CD8 |
| CLEC12A | CD28 | NKG2D | CD3ζ |
| CLEC12A | CD28 | NKG2D | CD3δ |
| CLEC12A | CD28 | NKG2D | CD3γ |
| CLEC12A | CD28 | NKG2D | CD3ε |
| CLEC12A | CD28 | NKG2D | FcγRI-γ |
| CLEC12A | CD28 | NKG2D | FcγRIII-γ |
| CLEC12A | CD28 | NKG2D | FcεRIβ |
| CLEC12A | CD28 | NKG2D | FcεRIγ |
| CLEC12A | CD28 | NKG2D | DAP10 |
| CLEC12A | CD28 | NKG2D | DAP12 |
| CLEC12A | CD28 | NKG2D | CD32 |
| CLEC12A | CD28 | NKG2D | CD79a |
| CLEC12A | CD28 | NKG2D | CD79b |
| CLEC12A | CD8 | CD28 | CD8 |
| CLEC12A | CD8 | CD28 | CD3ζ |
| CLEC12A | CD8 | CD28 | CD3δ |
| CLEC12A | CD8 | CD28 | CD3γ |
| CLEC12A | CD8 | CD28 | CD3E |
| CLEC12A | CD8 | CD28 | FcγRI-γ |
| CLEC12A | CD8 | CD28 | FcγRIII-γ |
| CLEC12A | CD8 | CD28 | FcεRIβ |
| CLEC12A | CD8 | CD28 | FcεRIγ |
| CLEC12A | CD8 | CD28 | DAP10 |
| CLEC12A | CD8 | CD28 | DAP12 |
| CLEC12A | CD8 | CD28 | CD32 |
| CLEC12A | CD8 | CD28 | CD79a |
| CLEC12A | CD8 | CD28 | CD79b |
| CLEC12A | CD8 | CD8 | CD8 |
| CLEC12A | CD8 | CD8 | CD3ζ |
| CLEC12A | CD8 | CD8 | CD3δ |
| CLEC12A | CD8 | CD8 | CD3γ |
| CLEC12A | CD8 | CD8 | CD3ε |
| CLEC12A | CD8 | CD8 | FcγRI-γ |
| CLEC12A | CD8 | CD8 | FcγRIII-γ |
| CLEC12A | CD8 | CD8 | FcεRIβ |
| CLEC12A | CD8 | CD8 | FcεRIγ |
| CLEC12A | CD8 | CD8 | DAP10 |
| CLEC12A | CD8 | CD8 | DAP12 |
| CLEC12A | CD8 | CD8 | CD32 |
| CLEC12A | CD8 | CD8 | CD79a |
| CLEC12A | CD8 | CD8 | CD79b |
| CLEC12A | CD8 | CD4 | CD8 |
| CLEC12A | CD8 | CD4 | CD3ζ |
| CLEC12A | CD8 | CD4 | CD3δ |
| CLEC12A | CD8 | CD4 | CD3γ |
| CLEC12A | CD8 | CD4 | CD3ε |
| CLEC12A | CD8 | CD4 | FcγRI-γ |
| CLEC12A | CD8 | CD4 | FcγRIII-γ |
| CLEC12A | CD8 | CD4 | FcεRIβ |
| CLEC12A | CD8 | CD4 | FcεRIγ |
| CLEC12A | CD8 | CD4 | DAP10 |
| CLEC12A | CD8 | CD4 | DAP12 |
| CLEC12A | CD8 | CD4 | CD32 |
| CLEC12A | CD8 | CD4 | CD79a |
| CLEC12A | CD8 | CD4 | CD79b |
| CLEC12A | CD8 | b2c | CD8 |
| CLEC12A | CD8 | b2c | CD3ζ |
| CLEC12A | CD8 | b2c | CD3δ |
| CLEC12A | CD8 | b2c | CD3γ |
| CLEC12A | CD8 | b2c | CD3ε |
| CLEC12A | CD8 | b2c | FcγRI-γ |
| CLEC12A | CD8 | b2c | FcγRIII-γ |
| CLEC12A | CD8 | b2c | FcεRIβ |
| CLEC12A | CD8 | b2c | FcεRIγ |
| CLEC12A | CD8 | b2c | DAP10 |
| CLEC12A | CD8 | b2c | DAP12 |
| CLEC12A | CD8 | b2c | CD32 |
| CLEC12A | CD8 | b2c | CD79a |
| CLEC12A | CD8 | b2c | CD79b |
| CLEC12A | CD8 | CD137/41BB | CD8 |
| CLEC12A | CD8 | CD137/41BB | CD3ζ |
| CLEC12A | CD8 | CD137/41BB | CD3δ |
| CLEC12A | CD8 | CD137/41BB | CD3γ |
| CLEC12A | CD8 | CD137/41BB | CD3ε |
| CLEC12A | CD8 | CD137/41BB | FcγRI-γ |
| CLEC12A | CD8 | CD137/41BB | FcγRIII-γ |
| CLEC12A | CD8 | CD137/41BB | FcεRIβ |
| CLEC12A | CD8 | CD137/41BB | FcεRIγ |
| CLEC12A | CD8 | CD137/41BB | DAP10 |
| CLEC12A | CD8 | CD137/41BB | DAP12 |
| CLEC12A | CD8 | CD137/41BB | CD32 |
| CLEC12A | CD8 | CD137/41BB | CD79a |
| CLEC12A | CD8 | CD137/41BB | CD79b |
| CLEC12A | CD8 | ICOS | CD8 |
| CLEC12A | CD8 | ICOS | CD3ζ |
| CLEC12A | CD8 | ICOS | CD3δ |
| CLEC12A | CD8 | ICOS | CD3γ |
| CLEC12A | CD8 | ICOS | CD3ε |
| CLEC12A | CD8 | ICOS | FcγRI-γ |
| CLEC12A | CD8 | ICOS | FcγRIII-γ |
| CLEC12A | CD8 | ICOS | FcεRIβ |
| CLEC12A | CD8 | ICOS | FcεRIγ |
| CLEC12A | CD8 | ICOS | DAP10 |
| CLEC12A | CD8 | ICOS | DAP12 |
| CLEC12A | CD8 | ICOS | CD32 |
| CLEC12A | CD8 | ICOS | CD79a |
| CLEC12A | CD8 | ICOS | CD79b |
| CLEC12A | CD8 | CD27 | CD8 |
| CLEC12A | CD8 | CD27 | CD3ζ |
| CLEC12A | CD8 | CD27 | CD3δ |
| CLEC12A | CD8 | CD27 | CD3γ |
| CLEC12A | CD8 | CD27 | CD3ε |
| CLEC12A | CD8 | CD27 | FcγRI-γ |
| CLEC12A | CD8 | CD27 | FcγRIII-γ |
| CLEC12A | CD8 | CD27 | FcεRIβ |
| CLEC12A | CD8 | CD27 | FcεRIγ |
| CLEC12A | CD8 | CD27 | DAP10 |
| CLEC12A | CD8 | CD27 | DAP12 |
| CLEC12A | CD8 | CD27 | CD32 |
| CLEC12A | CD8 | CD27 | CD79a |
| CLEC12A | CD8 | CD27 | CD79b |
| CLEC12A | CD8 | CD28δ | CD8 |
| CLEC12A | CD8 | CD28δ | CD3ζ |
| CLEC12A | CD8 | CD28δ | CD3δ |
| CLEC12A | CD8 | CD28δ | CD3ε |
| CLEC12A | CD8 | CD28δ | FcγRI-γ |
| CLEC12A | CD8 | CD28δ | FcγRIII-γ |
| CLEC12A | CD8 | CD28δ | FcεRIβ |
| CLEC12A | CD8 | CD28δ | FcεRIγ |
| CLEC12A | CD8 | CD28δ | DAP10 |
| CLEC12A | CD8 | CD28δ | DAP12 |
| CLEC12A | CD8 | CD28δ | CD32 |
| CLEC12A | CD8 | CD28δ | CD79a |
| CLEC12A | CD8 | CD28δ | CD79b |
| CLEC12A | CD8 | CD80 | CD8 |
| CLEC12A | CD8 | CD80 | CD3ζ |

TABLE 3-continued

Third Generation CARs

| ScFv | Co-stimulatory Signal | Co-stimulatory Signal | Signal Domain |
|---|---|---|---|
| CLEC12A | CD8 | CD80 | CD3δ |
| CLEC12A | CD8 | CD80 | CD3γ |
| CLEC12A | CD8 | CD80 | CD3ε |
| CLEC12A | CD8 | CD80 | FcγRI-γ |
| CLEC12A | CD8 | CD80 | FcγRIII-γ |
| CLEC12A | CD8 | CD80 | FcεRIβ |
| CLEC12A | CD8 | CD80 | FcεRIγ |
| CLEC12A | CD8 | CD80 | DAP10 |
| CLEC12A | CD8 | CD80 | DAP12 |
| CLEC12A | CD8 | CD80 | CD32 |
| CLEC12A | CD8 | CD80 | CD79a |
| CLEC12A | CD8 | CD80 | CD79b |
| CLEC12A | CD8 | CD86 | CD8 |
| CLEC12A | CD8 | CD86 | CD3ζ |
| CLEC12A | CD8 | CD86 | CD3δ |
| CLEC12A | CD8 | CD86 | CD3γ |
| CLEC12A | CD8 | CD86 | CD3ε |
| CLEC12A | CD8 | CD86 | FcγRI-γ |
| CLEC12A | CD8 | CD86 | FcγRIII-γ |
| CLEC12A | CD8 | CD86 | FcεRIβ |
| CLEC12A | CD8 | CD86 | FcεRIγ |
| CLEC12A | CD8 | CD86 | DAP10 |
| CLEC12A | CD8 | CD86 | DAP12 |
| CLEC12A | CD8 | CD86 | CD32 |
| CLEC12A | CD8 | CD86 | CD79a |
| CLEC12A | CD8 | CD86 | CD79b |
| CLEC12A | CD8 | OX40 | CD8 |
| CLEC12A | CD8 | OX40 | CD3ζ |
| CLEC12A | CD8 | OX40 | CD3δ |
| CLEC12A | CD8 | OX40 | CD3γ |
| CLEC12A | CD8 | OX40 | CD3ε |
| CLEC12A | CD8 | OX40 | FcγRI-γ |
| CLEC12A | CD8 | OX40 | FcγRIII-γ |
| CLEC12A | CD8 | OX40 | FcεRIβ |
| CLEC12A | CD8 | OX40 | FcεRIγ |
| CLEC12A | CD8 | OX40 | DAP10 |
| CLEC12A | CD8 | OX40 | DAP12 |
| CLEC12A | CD8 | OX40 | CD32 |
| CLEC12A | CD8 | OX40 | CD79a |
| CLEC12A | CD8 | OX40 | CD79b |
| CLEC12A | CD8 | DAP10 | CD8 |
| CLEC12A | CD8 | DAP10 | CD3ζ |
| CLEC12A | CD8 | DAP10 | CD3δ |
| CLEC12A | CD8 | DAP10 | CD3γ |
| CLEC12A | CD8 | DAP10 | CD3ε |
| CLEC12A | CD8 | DAP10 | FcγRI-γ |
| CLEC12A | CD8 | DAP10 | FcγRIII-γ |
| CLEC12A | CD8 | DAP10 | FcεRIβ |
| CLEC12A | CD8 | DAP10 | FcεRIγ |
| CLEC12A | CD8 | DAP10 | DAP10 |
| CLEC12A | CD8 | DAP10 | DAP12 |
| CLEC12A | CD8 | DAP10 | CD32 |
| CLEC12A | CD8 | DAP10 | CD79a |
| CLEC12A | CD8 | DAP10 | CD79b |
| CLEC12A | CD8 | DAP12 | CD8 |
| CLEC12A | CD8 | DAP12 | CD3ζ |
| CLEC12A | CD8 | DAP12 | CD3δ |
| CLEC12A | CD8 | DAP12 | CD3γ |
| CLEC12A | CD8 | DAP12 | CD3ε |
| CLEC12A | CD8 | DAP12 | FcγRI-γ |
| CLEC12A | CD8 | DAP12 | FcγRIII-γ |
| CLEC12A | CD8 | DAP12 | FcεRIβ |
| CLEC12A | CD8 | DAP12 | FcεRIγ |
| CLEC12A | CD8 | DAP12 | DAP10 |
| CLEC12A | CD8 | DAP12 | DAP12 |
| CLEC12A | CD8 | DAP12 | CD32 |
| CLEC12A | CD8 | DAP12 | CD79a |
| CLEC12A | CD8 | DAP12 | CD79b |
| CLEC12A | CD8 | MyD88 | CD8 |
| CLEC12A | CD8 | MyD88 | CD3ζ |
| CLEC12A | CD8 | MyD88 | CD3δ |
| CLEC12A | CD8 | MyD88 | CD3γ |
| CLEC12A | CD8 | MyD88 | CD3ε |
| CLEC12A | CD8 | MyD88 | FcγRI-γ |
| CLEC12A | CD8 | MyD88 | FcγRIII-γ |
| CLEC12A | CD8 | MyD88 | FcεRIβ |
| CLEC12A | CD8 | MyD88 | FcεRIγ |
| CLEC12A | CD8 | MyD88 | DAP10 |
| CLEC12A | CD8 | MyD88 | DAP12 |
| CLEC12A | CD8 | MyD88 | CD32 |
| CLEC12A | CD8 | MyD88 | CD79a |
| CLEC12A | CD8 | MyD88 | CD79b |
| CLEC12A | CD8 | CD7 | CD8 |
| CLEC12A | CD8 | CD7 | CD3ζ |
| CLEC12A | CD8 | CD7 | CD3δ |
| CLEC12A | CD8 | CD7 | CD3γ |
| CLEC12A | CD8 | CD7 | CD3ε |
| CLEC12A | CD8 | CD7 | FcγRI-γ |
| CLEC12A | CD8 | CD7 | FcγRIII-γ |
| CLEC12A | CD8 | CD7 | FcεRIβ |
| CLEC12A | CD8 | CD7 | FcεRIγ |
| CLEC12A | CD8 | CD7 | DAP10 |
| CLEC12A | CD8 | CD7 | DAP12 |
| CLEC12A | CD8 | CD7 | CD32 |
| CLEC12A | CD8 | CD7 | CD79a |
| CLEC12A | CD8 | CD7 | CD79b |
| CLEC12A | CD8 | BTNL3 | CD8 |
| CLEC12A | CD8 | BTNL3 | CD3ζ |
| CLEC12A | CD8 | BTNL3 | CD3δ |
| CLEC12A | CD8 | BTNL3 | CD3γ |
| CLEC12A | CD8 | BTNL3 | CD3ε |
| CLEC12A | CD8 | BTNL3 | FcγRI-γ |
| CLEC12A | CD8 | BTNL3 | FcγRIII-γ |
| CLEC12A | CD8 | BTNL3 | FcεRIβ |
| CLEC12A | CD8 | BTNL3 | FcεRIγ |
| CLEC12A | CD8 | BTNL3 | DAP10 |
| CLEC12A | CD8 | BTNL3 | DAP12 |
| CLEC12A | CD8 | BTNL3 | CD32 |
| CLEC12A | CD8 | BTNL3 | CD79a |
| CLEC12A | CD8 | BTNL3 | CD79b |
| CLEC12A | CD8 | NKG2D | CD8 |
| CLEC12A | CD8 | NKG2D | CD3ζ |
| CLEC12A | CD8 | NKG2D | CD3δ |
| CLEC12A | CD8 | NKG2D | CD3γ |
| CLEC12A | CD8 | NKG2D | CD3ε |
| CLEC12A | CD8 | NKG2D | FcγRI-γ |
| CLEC12A | CD8 | NKG2D | FcγRIII-γ |
| CLEC12A | CD8 | NKG2D | FcεRIβ |
| CLEC12A | CD8 | NKG2D | FcεRIγ |
| CLEC12A | CD8 | NKG2D | DAP10 |
| CLEC12A | CD8 | NKG2D | DAP12 |
| CLEC12A | CD8 | NKG2D | CD32 |
| CLEC12A | CD8 | NKG2D | CD79a |
| CLEC12A | CD8 | NKG2D | CD79b |
| CLEC12A | CD4 | CD28 | CD8 |
| CLEC12A | CD4 | CD28 | CD3ζ |
| CLEC12A | CD4 | CD28 | CD3δ |
| CLEC12A | CD4 | CD28 | CD3γ |
| CLEC12A | CD4 | CD28 | CD3ε |
| CLEC12A | CD4 | CD28 | FcγRI-γ |
| CLEC12A | CD4 | CD28 | FcγRIII-γ |
| CLEC12A | CD4 | CD28 | FcεRIβ |
| CLEC12A | CD4 | CD28 | FcεRIγ |
| CLEC12A | CD4 | CD28 | DAP10 |
| CLEC12A | CD4 | CD28 | DAP12 |
| CLEC12A | CD4 | CD28 | CD32 |
| CLEC12A | CD4 | CD28 | CD79a |
| CLEC12A | CD4 | CD28 | CD79b |
| CLEC12A | CD4 | CD8 | CD8 |
| CLEC12A | CD4 | CD8 | CD3ζ |
| CLEC12A | CD4 | CD8 | CD3δ |
| CLEC12A | CD4 | CD8 | CD3γ |
| CLEC12A | CD4 | CD8 | CD3ε |
| CLEC12A | CD4 | CD8 | FcγRI-γ |
| CLEC12A | CD4 | CD8 | FcγRIII-γ |
| CLEC12A | CD4 | CD8 | FcεRIβ |
| CLEC12A | CD4 | CD8 | FcεRIγ |
| CLEC12A | CD4 | CD8 | DAP10 |
| CLEC12A | CD4 | CD8 | DAP12 |
| CLEC12A | CD4 | CD8 | CD32 |

TABLE 3-continued

Third Generation CARs

| ScFv | Co-stimulatory Signal | Co-stimulatory Signal | Signal Domain |
|---|---|---|---|
| CLEC12A | CD4 | CD8 | CD79a |
| CLEC12A | CD4 | CD8 | CD79b |
| CLEC12A | CD4 | CD4 | CD8 |
| CLEC12A | CD4 | CD4 | CD3ζ |
| CLEC12A | CD4 | CD4 | CD3δ |
| CLEC12A | CD4 | CD4 | CD3γ |
| CLEC12A | CD4 | CD4 | CD3ε |
| CLEC12A | CD4 | CD4 | FcγRI-γ |
| CLEC12A | CD4 | CD4 | FcγRIII-γ |
| CLEC12A | CD4 | CD4 | FcεRIβ |
| CLEC12A | CD4 | CD4 | FcεRIγ |
| CLEC12A | CD4 | CD4 | DAP10 |
| CLEC12A | CD4 | CD4 | DAP12 |
| CLEC12A | CD4 | CD4 | CD32 |
| CLEC12A | CD4 | CD4 | CD79a |
| CLEC12A | CD4 | CD4 | CD79b |
| CLEC12A | CD4 | b2c | CD8 |
| CLEC12A | CD4 | b2c | CD3ζ |
| CLEC12A | CD4 | b2c | CD3δ |
| CLEC12A | CD4 | b2c | CD3γ |
| CLEC12A | CD4 | b2c | CD3ε |
| CLEC12A | CD4 | b2c | FcγRI-γ |
| CLEC12A | CD4 | b2c | FcγRIII-γ |
| CLEC12A | CD4 | b2c | FcεRIβ |
| CLEC12A | CD4 | b2c | FcεRIγ |
| CLEC12A | CD4 | b2c | DAP10 |
| CLEC12A | CD4 | b2c | DAP12 |
| CLEC12A | CD4 | b2c | CD32 |
| CLEC12A | CD4 | b2c | CD79a |
| CLEC12A | CD4 | b2c | CD79b |
| CLEC12A | CD4 | CD137/41BB | CD8 |
| CLEC12A | CD4 | CD137/41BB | CD3ζ |
| CLEC12A | CD4 | CD137/41BB | CD3δ |
| CLEC12A | CD4 | CD137/41BB | CD3γ |
| CLEC12A | CD4 | CD137/41BB | CD3ε |
| CLEC12A | CD4 | CD137/41BB | FcγRI-γ |
| CLEC12A | CD4 | CD137/41BB | FcγRIII-γ |
| CLEC12A | CD4 | CD137/41BB | FcεRIβ |
| CLEC12A | CD4 | CD137/41BB | FcεRIγ |
| CLEC12A | CD4 | CD137/41BB | DAP10 |
| CLEC12A | CD4 | CD137/41BB | DAP12 |
| CLEC12A | CD4 | CD137/41BB | CD32 |
| CLEC12A | CD4 | CD137/41BB | CD79a |
| CLEC12A | CD4 | CD137/41BB | CD79b |
| CLEC12A | CD4 | ICOS | CD8 |
| CLEC12A | CD4 | ICOS | CD3ζ |
| CLEC12A | CD4 | ICOS | CD3δ |
| CLEC12A | CD4 | ICOS | CD3γ |
| CLEC12A | CD4 | ICOS | CD3ε |
| CLEC12A | CD4 | ICOS | FcγRI-γ |
| CLEC12A | CD4 | ICOS | FcγRIII-γ |
| CLEC12A | CD4 | ICOS | FcεRIβ |
| CLEC12A | CD4 | ICOS | FcεRIγ |
| CLEC12A | CD4 | ICOS | DAP10 |
| CLEC12A | CD4 | ICOS | DAP12 |
| CLEC12A | CD4 | ICOS | CD32 |
| CLEC12A | CD4 | ICOS | CD79a |
| CLEC12A | CD4 | ICOS | CD79b |
| CLEC12A | CD4 | CD27 | CD8 |
| CLEC12A | CD4 | CD27 | CD3ζ |
| CLEC12A | CD4 | CD27 | CD3δ |
| CLEC12A | CD4 | CD27 | CD3γ |
| CLEC12A | CD4 | CD27 | CD3ε |
| CLEC12A | CD4 | CD27 | FcγRI-γ |
| CLEC12A | CD4 | CD27 | FcγRIII-γ |
| CLEC12A | CD4 | CD27 | FcεRIβ |
| CLEC12A | CD4 | CD27 | FcεRIγ |
| CLEC12A | CD4 | CD27 | DAP10 |
| CLEC12A | CD4 | CD27 | DAP12 |
| CLEC12A | CD4 | CD27 | CD32 |
| CLEC12A | CD4 | CD27 | CD79a |
| CLEC12A | CD4 | CD27 | CD79b |
| CLEC12A | CD4 | CD28δ | CD8 |
| CLEC12A | CD4 | CD28δ | CD3ζ |
| CLEC12A | CD4 | CD28δ | CD3δ |
| CLEC12A | CD4 | CD28δ | CD3γ |
| CLEC12A | CD4 | CD28δ | CD3ε |
| CLEC12A | CD4 | CD28δ | FcγRI-γ |
| CLEC12A | CD4 | CD28δ | FcγRIII-γ |
| CLEC12A | CD4 | CD28δ | FcεRIβ |
| CLEC12A | CD4 | CD28δ | FcεRIγ |
| CLEC12A | CD4 | CD28δ | DAP10 |
| CLEC12A | CD4 | CD28δ | DAP12 |
| CLEC12A | CD4 | CD28δ | CD32 |
| CLEC12A | CD4 | CD28δ | CD79a |
| CLEC12A | CD4 | CD28δ | CD79b |
| CLEC12A | CD4 | CD80 | CD8 |
| CLEC12A | CD4 | CD80 | CD3ζ |
| CLEC12A | CD4 | CD80 | CD3δ |
| CLEC12A | CD4 | CD80 | CD3γ |
| CLEC12A | CD4 | CD80 | CD3ε |
| CLEC12A | CD4 | CD80 | FcγRI-γ |
| CLEC12A | CD4 | CD80 | FcγRIII-γ |
| CLEC12A | CD4 | CD80 | FcεRIβ |
| CLEC12A | CD4 | CD80 | FcεRIγ |
| CLEC12A | CD4 | CD80 | DAP10 |
| CLEC12A | CD4 | CD80 | DAP12 |
| CLEC12A | CD4 | CD80 | CD32 |
| CLEC12A | CD4 | CD80 | CD79a |
| CLEC12A | CD4 | CD80 | CD79b |
| CLEC12A | CD4 | CD86 | CD8 |
| CLEC12A | CD4 | CD86 | CD3ζ |
| CLEC12A | CD4 | CD86 | CD3δ |
| CLEC12A | CD4 | CD86 | CD3γ |
| CLEC12A | CD4 | CD86 | CD3ε |
| CLEC12A | CD4 | CD86 | FcγRI-γ |
| CLEC12A | CD4 | CD86 | FcγRIII-γ |
| CLEC12A | CD4 | CD86 | FcεRIβ |
| CLEC12A | CD4 | CD86 | FcεRIγ |
| CLEC12A | CD4 | CD86 | DAP10 |
| CLEC12A | CD4 | CD86 | DAP12 |
| CLEC12A | CD4 | CD86 | CD32 |
| CLEC12A | CD4 | CD86 | CD79a |
| CLEC12A | CD4 | CD86 | CD79b |
| CLEC12A | CD4 | OX40 | CD8 |
| CLEC12A | CD4 | OX40 | CD3ζ |
| CLEC12A | CD4 | OX40 | CD3δ |
| CLEC12A | CD4 | OX40 | CD3γ |
| CLEC12A | CD4 | OX40 | CD3ε |
| CLEC12A | CD4 | OX40 | FcγRI-γ |
| CLEC12A | CD4 | OX40 | FcγRIII-γ |
| CLEC12A | CD4 | OX40 | FcεRIβ |
| CLEC12A | CD4 | OX40 | FcεRIγ |
| CLEC12A | CD4 | OX40 | DAP10 |
| CLEC12A | CD4 | OX40 | DAP12 |
| CLEC12A | CD4 | OX40 | CD32 |
| CLEC12A | CD4 | OX40 | CD79a |
| CLEC12A | CD4 | OX40 | CD79b |
| CLEC12A | CD4 | DAP10 | CD8 |
| CLEC12A | CD4 | DAP10 | CD3ζ |
| CLEC12A | CD4 | DAP10 | CD3δ |
| CLEC12A | CD4 | DAP10 | CD3γ |
| CLEC12A | CD4 | DAP10 | CD3ε |
| CLEC12A | CD4 | DAP10 | FcγRI-γ |
| CLEC12A | CD4 | DAP10 | FcγRIII-γ |
| CLEC12A | CD4 | DAP10 | FcεRIβ |
| CLEC12A | CD4 | DAP10 | FcεRIγ |
| CLEC12A | CD4 | DAP10 | DAP10 |
| CLEC12A | CD4 | DAP10 | DAP12 |
| CLEC12A | CD4 | DAP10 | CD32 |
| CLEC12A | CD4 | DAP10 | CD79a |
| CLEC12A | CD4 | DAP10 | CD79b |
| CLEC12A | CD4 | DAP12 | CD8 |
| CLEC12A | CD4 | DAP12 | CD3ζ |
| CLEC12A | CD4 | DAP12 | CD3δ |
| CLEC12A | CD4 | DAP12 | CD3γ |
| CLEC12A | CD4 | DAP12 | CD3ε |
| CLEC12A | CD4 | DAP12 | FcγRI-γ |
| CLEC12A | CD4 | DAP12 | FcγRIII-γ |
| CLEC12A | CD4 | DAP12 | FcεRIβ |

TABLE 3-continued

Third Generation CARs

| ScFv | Co-stimulatory Signal | Co-stimulatory Signal | Signal Domain |
|---|---|---|---|
| CLEC12A | CD4 | DAP12 | FcεRIγ |
| CLEC12A | CD4 | DAP12 | DAP10 |
| CLEC12A | CD4 | DAP12 | DAP12 |
| CLEC12A | CD4 | DAP12 | CD32 |
| CLEC12A | CD4 | DAP12 | CD79a |
| CLEC12A | CD4 | DAP12 | CD79b |
| CLEC12A | CD4 | MyD88 | CD8 |
| CLEC12A | CD4 | MyD88 | CD3ζ |
| CLEC12A | CD4 | MyD88 | CD3δ |
| CLEC12A | CD4 | MyD88 | CD3γ |
| CLEC12A | CD4 | MyD88 | CD3ε |
| CLEC12A | CD4 | MyD88 | FcγRI-γ |
| CLEC12A | CD4 | MyD88 | FcγRIII-γ |
| CLEC12A | CD4 | MyD88 | FcεRIβ |
| CLEC12A | CD4 | MyD88 | FcεRIγ |
| CLEC12A | CD4 | MyD88 | DAP10 |
| CLEC12A | CD4 | MyD88 | DAP12 |
| CLEC12A | CD4 | MyD88 | CD32 |
| CLEC12A | CD4 | MyD88 | CD79a |
| CLEC12A | CD4 | MyD88 | CD79b |
| CLEC12A | CD4 | CD7 | CD8 |
| CLEC12A | CD4 | CD7 | CD3ζ |
| CLEC12A | CD4 | CD7 | CD3δ |
| CLEC12A | CD4 | CD7 | CD3γ |
| CLEC12A | CD4 | CD7 | CD3ε |
| CLEC12A | CD4 | CD7 | FcγRI-γ |
| CLEC12A | CD4 | CD7 | FcγRIII-γ |
| CLEC12A | CD4 | CD7 | FcεRIβ |
| CLEC12A | CD4 | CD7 | FcεRIγ |
| CLEC12A | CD4 | CD7 | DAP10 |
| CLEC12A | CD4 | CD7 | DAP12 |
| CLEC12A | CD4 | CD7 | CD32 |
| CLEC12A | CD4 | CD7 | CD79a |
| CLEC12A | CD4 | CD7 | CD79b |
| CLEC12A | CD4 | BTNL3 | CD8 |
| CLEC12A | CD4 | BTNL3 | CD3ζ |
| CLEC12A | CD4 | BTNL3 | CD3δ |
| CLEC12A | CD4 | BTNL3 | CD3γ |
| CLEC12A | CD4 | BTNL3 | CD3ε |
| CLEC12A | CD4 | BTNL3 | FcγRI-γ |
| CLEC12A | CD4 | BTNL3 | FcγRIII-γ |
| CLEC12A | CD4 | BTNL3 | FcεRIβ |
| CLEC12A | CD4 | BTNL3 | FcεRIγ |
| CLEC12A | CD4 | BTNL3 | DAP10 |
| CLEC12A | CD4 | BTNL3 | DAP12 |
| CLEC12A | CD4 | BTNL3 | CD32 |
| CLEC12A | CD4 | BTNL3 | CD79a |
| CLEC12A | CD4 | BTNL3 | CD79b |
| CLEC12A | CD4 | NKG2D | CD8 |
| CLEC12A | CD4 | NKG2D | CD3ζ |
| CLEC12A | CD4 | NKG2D | CD3δ |
| CLEC12A | CD4 | NKG2D | CD3γ |
| CLEC12A | CD4 | NKG2D | CD3ε |
| CLEC12A | CD4 | NKG2D | FcγRI-γ |
| CLEC12A | CD4 | NKG2D | FcγRIII-γ |
| CLEC12A | CD4 | NKG2D | FcεRIβ |
| CLEC12A | CD4 | NKG2D | FcεRIγ |
| CLEC12A | CD4 | NKG2D | DAP10 |
| CLEC12A | CD4 | NKG2D | DAP12 |
| CLEC12A | CD4 | NKG2D | CD32 |
| CLEC12A | CD4 | NKG2D | CD79a |
| CLEC12A | CD4 | NKG2D | CD79b |
| CLEC12A | b2c | CD28 | CD8 |
| CLEC12A | b2c | CD28 | CD3ζ |
| CLEC12A | b2c | CD28 | CD3δ |
| CLEC12A | b2c | CD28 | CD3γ |
| CLEC12A | b2c | CD28 | CD3ε |
| CLEC12A | b2c | CD28 | FcγRI-γ |
| CLEC12A | b2c | CD28 | FcγRIII-γ |
| CLEC12A | b2c | CD28 | FcεRIβ |
| CLEC12A | b2c | CD28 | FcεRIγ |
| CLEC12A | b2c | CD28 | DAP10 |
| CLEC12A | b2c | CD28 | DAP12 |
| CLEC12A | b2c | CD28 | CD32 |
| CLEC12A | b2c | CD28 | CD79a |
| CLEC12A | b2c | CD28 | CD79b |
| CLEC12A | b2c | CD8 | CD8 |
| CLEC12A | b2c | CD8 | CD3ζ |
| CLEC12A | b2c | CD8 | CD3δ |
| CLEC12A | b2c | CD8 | CD3γ |
| CLEC12A | b2c | CD8 | CD3ε |
| CLEC12A | b2c | CD8 | FcγRI-γ |
| CLEC12A | b2c | CD8 | FcγRIII-γ |
| CLEC12A | b2c | CD8 | FcεRIβ |
| CLEC12A | b2c | CD8 | FcεRIγ |
| CLEC12A | b2c | CD8 | DAP10 |
| CLEC12A | b2c | CD8 | DAP12 |
| CLEC12A | b2c | CD8 | CD32 |
| CLEC12A | b2c | CD8 | CD79a |
| CLEC12A | b2c | CD8 | CD79b |
| CLEC12A | b2c | CD4 | CD8 |
| CLEC12A | b2c | CD4 | CD3ζ |
| CLEC12A | b2c | CD4 | CD3δ |
| CLEC12A | b2c | CD4 | CD3γ |
| CLEC12A | b2c | CD4 | CD3ε |
| CLEC12A | b2c | CD4 | FcγRI-γ |
| CLEC12A | b2c | CD4 | FcγRIII-γ |
| CLEC12A | b2c | CD4 | FcεRIβ |
| CLEC12A | b2c | CD4 | FcεRIγ |
| CLEC12A | b2c | CD4 | DAP10 |
| CLEC12A | b2c | CD4 | DAP12 |
| CLEC12A | b2c | CD4 | CD32 |
| CLEC12A | b2c | CD4 | CD79a |
| CLEC12A | b2c | CD4 | CD79b |
| CLEC12A | b2c | b2c | CD8 |
| CLEC12A | b2c | b2c | CD3ζ |
| CLEC12A | b2c | b2c | CD3δ |
| CLEC12A | b2c | b2c | CD3γ |
| CLEC12A | b2c | b2c | CD3ε |
| CLEC12A | b2c | b2c | FcγRI-γ |
| CLEC12A | b2c | b2c | FcγRIII-γ |
| CLEC12A | b2c | b2c | FcεRIβ |
| CLEC12A | b2c | b2c | FcεRIγ |
| CLEC12A | b2c | b2c | DAP10 |
| CLEC12A | b2c | b2c | DAP12 |
| CLEC12A | b2c | b2c | CD32 |
| CLEC12A | b2c | b2c | CD79a |
| CLEC12A | b2c | b2c | CD79b |
| CLEC12A | b2c | CD137/41BB | CD8 |
| CLEC12A | b2c | CD137/41BB | CD3ζ |
| CLEC12A | b2c | CD137/41BB | CD3δ |
| CLEC12A | b2c | CD137/41BB | CD3δ |
| CLEC12A | b2c | CD137/41BB | CD3ε |
| CLEC12A | b2c | CD137/41BB | FcγRI-γ |
| CLEC12A | b2c | CD137/41BB | FcδRIII-γ |
| CLEC12A | b2c | CD137/41BB | FcεRIβ |
| CLEC12A | b2c | CD137/41BB | FcεRIγ |
| CLEC12A | b2c | CD137/41BB | DAP10 |
| CLEC12A | b2c | CD137/41BB | DAP12 |
| CLEC12A | b2c | CD137/41BB | CD32 |
| CLEC12A | b2c | CD137/41BB | CD79a |
| CLEC12A | b2c | CD137/41BB | CD79b |
| CLEC12A | b2c | ICOS | CD8 |
| CLEC12A | b2c | ICOS | CD3ζ |
| CLEC12A | b2c | ICOS | CD3δ |
| CLEC12A | b2c | ICOS | CD3γ |
| CLEC12A | b2c | ICOS | CD3ε |
| CLEC12A | b2c | ICOS | FcγRI-γ |
| CLEC12A | b2c | ICOS | FcγRIII-γ |
| CLEC12A | b2c | ICOS | FcεRIβ |
| CLEC12A | b2c | ICOS | FcεRIγ |
| CLEC12A | b2c | ICOS | DAP10 |
| CLEC12A | b2c | ICOS | DAP12 |
| CLEC12A | b2c | ICOS | CD32 |
| CLEC12A | b2c | ICOS | CD79a |
| CLEC12A | b2c | ICOS | CD79b |
| CLEC12A | b2c | CD27 | CD8 |
| CLEC12A | b2c | CD27 | CD3ζ |
| CLEC12A | b2c | CD27 | CD3δ |
| CLEC12A | b2c | CD27 | CD3γ |

TABLE 3-continued

Third Generation CARs

| ScFv | Co-stimulatory Signal | Co-stimulatory Signal | Signal Domain |
|---|---|---|---|
| CLEC12A | b2c | CD27 | CD3ε |
| CLEC12A | b2c | CD27 | FcγRI-γ |
| CLEC12A | b2c | CD27 | FcγRIII-γ |
| CLEC12A | b2c | CD27 | FcεRIβ |
| CLEC12A | b2c | CD27 | FcεRIγ |
| CLEC12A | b2c | CD27 | DAP10 |
| CLEC12A | b2c | CD27 | DAP12 |
| CLEC12A | b2c | CD27 | CD32 |
| CLEC12A | b2c | CD27 | CD79a |
| CLEC12A | b2c | CD27 | CD79b |
| CLEC12A | b2c | CD28δ | CD8 |
| CLEC12A | b2c | CD28δ | CD3ζ |
| CLEC12A | b2c | CD28δ | CD3δ |
| CLEC12A | b2c | CD28δ | CD3γ |
| CLEC12A | b2c | CD28δ | CD3ε |
| CLEC12A | b2c | CD28δ | FcγRI-γ |
| CLEC12A | b2c | CD28δ | FcγRIII-γ |
| CLEC12A | b2c | CD28δ | FcεRIβ |
| CLEC12A | b2c | CD28δ | FcεRIγ |
| CLEC12A | b2c | CD28δ | DAP10 |
| CLEC12A | b2c | CD28δ | DAP12 |
| CLEC12A | b2c | CD28δ | CD32 |
| CLEC12A | b2c | CD28δ | CD79a |
| CLEC12A | b2c | CD28δ | CD79b |
| CLEC12A | b2c | CD80 | CD8 |
| CLEC12A | b2c | CD80 | CD3ζ |
| CLEC12A | b2c | CD80 | CD3δ |
| CLEC12A | b2c | CD80 | CD3γ |
| CLEC12A | b2c | CD80 | CD3ε |
| CLEC12A | b2c | CD80 | FcγRI-γ |
| CLEC12A | b2c | CD80 | FcγRIII-γ |
| CLEC12A | b2c | CD80 | FcεRIβ |
| CLEC12A | b2c | CD80 | FcεRIγ |
| CLEC12A | b2c | CD80 | DAP10 |
| CLEC12A | b2c | CD80 | DAP12 |
| CLEC12A | b2c | CD80 | CD32 |
| CLEC12A | b2c | CD80 | CD79a |
| CLEC12A | b2c | CD80 | CD79b |
| CLEC12A | b2c | CD86 | CD8 |
| CLEC12A | b2c | CD86 | CD3ζ |
| CLEC12A | b2c | CD86 | CD3δ |
| CLEC12A | b2c | CD86 | CD3γ |
| CLEC12A | b2c | CD86 | CD3ε |
| CLEC12A | b2c | CD86 | FcγRI-γ |
| CLEC12A | b2c | CD86 | FcγRIII-γ |
| CLEC12A | b2c | CD86 | FcεRIβ |
| CLEC12A | b2c | CD86 | FcεRIγ |
| CLEC12A | b2c | CD86 | DAP10 |
| CLEC12A | b2c | CD86 | DAP12 |
| CLEC12A | b2c | CD86 | CD32 |
| CLEC12A | b2c | CD86 | CD79a |
| CLEC12A | b2c | CD86 | CD79b |
| CLEC12A | b2c | OX40 | CD8 |
| CLEC12A | b2c | OX40 | CD3ζ |
| CLEC12A | b2c | OX40 | CD3δ |
| CLEC12A | b2c | OX40 | CD3γ |
| CLEC12A | b2c | OX40 | CD3ε |
| CLEC12A | b2c | OX40 | FcγRI-γ |
| CLEC12A | b2c | OX40 | FcγRIII-γ |
| CLEC12A | b2c | OX40 | FcεRIβ |
| CLEC12A | b2c | OX40 | FcεRIγ |
| CLEC12A | b2c | OX40 | DAP10 |
| CLEC12A | b2c | OX40 | DAP12 |
| CLEC12A | b2c | OX40 | CD32 |
| CLEC12A | b2c | OX40 | CD79a |
| CLEC12A | b2c | OX40 | CD79b |
| CLEC12A | b2c | DAP10 | CD8 |
| CLEC12A | b2c | DAP10 | CD3ζ |
| CLEC12A | b2c | DAP10 | CD3δ |
| CLEC12A | b2c | DAP10 | CD3γ |
| CLEC12A | b2c | DAP10 | CD3ε |
| CLEC12A | b2c | DAP10 | FcγRI-γ |
| CLEC12A | b2c | DAP10 | FcγRIII-γ |
| CLEC12A | b2c | DAP10 | FcεRIβ |
| CLEC12A | b2c | DAP10 | FcεRIγ |
| CLEC12A | b2c | DAP10 | DAP10 |
| CLEC12A | b2c | DAP10 | DAP12 |
| CLEC12A | b2c | DAP10 | CD32 |
| CLEC12A | b2c | DAP10 | CD79a |
| CLEC12A | b2c | DAP10 | CD79b |
| CLEC12A | b2c | DAP12 | CD8 |
| CLEC12A | b2c | DAP12 | CD3ζ |
| CLEC12A | b2c | DAP12 | CD3δ |
| CLEC12A | b2c | DAP12 | CD3γ |
| CLEC12A | b2c | DAP12 | CD3ε |
| CLEC12A | b2c | DAP12 | FcγRI-γ |
| CLEC12A | b2c | DAP12 | FcγRIII-γ |
| CLEC12A | b2c | DAP12 | FcεRIβ |
| CLEC12A | b2c | DAP12 | FcεRIγ |
| CLEC12A | b2c | DAP12 | DAP10 |
| CLEC12A | b2c | DAP12 | DAP12 |
| CLEC12A | b2c | DAP12 | CD32 |
| CLEC12A | b2c | DAP12 | CD79a |
| CLEC12A | b2c | DAP12 | CD79b |
| CLEC12A | b2c | MyD88 | CD8 |
| CLEC12A | b2c | MyD88 | CD3ζ |
| CLEC12A | b2c | MyD88 | CD3δ |
| CLEC12A | b2c | MyD88 | CD3γ |
| CLEC12A | b2c | MyD88 | CD3ε |
| CLEC12A | b2c | MyD88 | FcγRI-γ |
| CLEC12A | b2c | MyD88 | FcγRIII-γ |
| CLEC12A | b2c | MyD88 | FcεRIβ |
| CLEC12A | b2c | MyD88 | FcεRIγ |
| CLEC12A | b2c | MyD88 | DAP10 |
| CLEC12A | b2c | MyD88 | DAP12 |
| CLEC12A | b2c | MyD88 | CD32 |
| CLEC12A | b2c | MyD88 | CD79a |
| CLEC12A | b2c | MyD88 | CD79b |
| CLEC12A | b2c | CD7 | CD8 |
| CLEC12A | b2c | CD7 | CD3ζ |
| CLEC12A | b2c | CD7 | CD3δ |
| CLEC12A | b2c | CD7 | CD3γ |
| CLEC12A | b2c | CD7 | CD3ε |
| CLEC12A | b2c | CD7 | FcγRI-γ |
| CLEC12A | b2c | CD7 | FcγRIII-γ |
| CLEC12A | b2c | CD7 | FcεRIβ |
| CLEC12A | b2c | CD7 | FcεRIγ |
| CLEC12A | b2c | CD7 | DAP10 |
| CLEC12A | b2c | CD7 | DAP12 |
| CLEC12A | b2c | CD7 | CD32 |
| CLEC12A | b2c | CD7 | CD79a |
| CLEC12A | b2c | CD7 | CD79b |
| CLEC12A | b2c | BTNL3 | CD8 |
| CLEC12A | b2c | BTNL3 | CD3ζ |
| CLEC12A | b2c | BTNL3 | CD3δ |
| CLEC12A | b2c | BTNL3 | CD3γ |
| CLEC12A | b2c | BTNL3 | CD3ε |
| CLEC12A | b2c | BTNL3 | FcγRI-γ |
| CLEC12A | b2c | BTNL3 | FcγRIII-γ |
| CLEC12A | b2c | BTNL3 | FcεRIβ |
| CLEC12A | b2c | BTNL3 | FcεRIγ |
| CLEC12A | b2c | BTNL3 | DAP10 |
| CLEC12A | b2c | BTNL3 | DAP12 |
| CLEC12A | b2c | BTNL3 | CD32 |
| CLEC12A | b2c | BTNL3 | CD79a |
| CLEC12A | b2c | BTNL3 | CD79b |
| CLEC12A | b2c | NKG2D | CD8 |
| CLEC12A | b2c | NKG2D | CD3ζ |
| CLEC12A | b2c | NKG2D | CD3δ |
| CLEC12A | b2c | NKG2D | CD3γ |
| CLEC12A | b2c | NKG2D | CD3ε |
| CLEC12A | b2c | NKG2D | FcγRI-γ |
| CLEC12A | b2c | NKG2D | FcγRIII-γ |
| CLEC12A | b2c | NKG2D | FcεRIβ |
| CLEC12A | b2c | NKG2D | FcεRIγ |
| CLEC12A | b2c | NKG2D | DAP10 |
| CLEC12A | b2c | NKG2D | DAP12 |
| CLEC12A | b2c | NKG2D | CD32 |
| CLEC12A | b2c | NKG2D | CD79a |
| CLEC12A | b2c | NKG2D | CD79b |

TABLE 3-continued

Third Generation CARs

| ScFv | Co-stimulatory Signal | Co-stimulatory Signal | Signal Domain |
|---|---|---|---|
| CLEC12A | CD137/41BB | CD28 | CD8 |
| CLEC12A | CD137/41BB | CD28 | CD3ζ |
| CLEC12A | CD137/41BB | CD28 | CD3δ |
| CLEC12A | CD137/41BB | CD28 | CD3γ |
| CLEC12A | CD137/41BB | CD28 | CD3ε |
| CLEC12A | CD137/41BB | CD28 | FcγRI-γ |
| CLEC12A | CD137/41BB | CD28 | FcγRIII-γ |
| CLEC12A | CD137/41BB | CD28 | FcεRIβ |
| CLEC12A | CD137/41BB | CD28 | FcεRIγ |
| CLEC12A | CD137/41BB | CD28 | DAP10 |
| CLEC12A | CD137/41BB | CD28 | DAP12 |
| CLEC12A | CD137/41BB | CD28 | CD32 |
| CLEC12A | CD137/41BB | CD28 | CD79a |
| CLEC12A | CD137/41BB | CD28 | CD79b |
| CLEC12A | CD137/41BB | CD8 | CD8 |
| CLEC12A | CD137/41BB | CD8 | CD3ζ |
| CLEC12A | CD137/41BB | CD8 | CD3δ |
| CLEC12A | CD137/41BB | CD8 | CD3γ |
| CLEC12A | CD137/41BB | CD8 | CD3ε |
| CLEC12A | CD137/41BB | CD8 | FcγRI-γ |
| CLEC12A | CD137/41BB | CD8 | FcγRIII-γ |
| CLEC12A | CD137/41BB | CD8 | FcεRIβ |
| CLEC12A | CD137/41BB | CD8 | FcεRIγ |
| CLEC12A | CD137/41BB | CD8 | DAP10 |
| CLEC12A | CD137/41BB | CD8 | DAP12 |
| CLEC12A | CD137/41BB | CD8 | CD32 |
| CLEC12A | CD137/41BB | CD8 | CD79a |
| CLEC12A | CD137/41BB | CD8 | CD79b |
| CLEC12A | CD137/41BB | CD4 | CD8 |
| CLEC12A | CD137/41BB | CD4 | CD3ζ |
| CLEC12A | CD137/41BB | CD4 | CD3δ |
| CLEC12A | CD137/41BB | CD4 | CD3γ |
| CLEC12A | CD137/41BB | CD4 | CD3ε |
| CLEC12A | CD137/41BB | CD4 | FcγRI-γ |
| CLEC12A | CD137/41BB | CD4 | FcγRIII-γ |
| CLEC12A | CD137/41BB | CD4 | FcεRIβ |
| CLEC12A | CD137/41BB | CD4 | FcεRIγ |
| CLEC12A | CD137/41BB | CD4 | DAP10 |
| CLEC12A | CD137/41BB | CD4 | DAP12 |
| CLEC12A | CD137/41BB | CD4 | CD32 |
| CLEC12A | CD137/41BB | CD4 | CD79a |
| CLEC12A | CD137/41BB | CD4 | CD79b |
| CLEC12A | CD137/41BB | b2c | CD8 |
| CLEC12A | CD137/41BB | b2c | CD3ζ |
| CLEC12A | CD137/41BB | b2c | CD3δ |
| CLEC12A | CD137/41BB | b2c | CD3γ |
| CLEC12A | CD137/41BB | b2c | CD3ε |
| CLEC12A | CD137/41BB | b2c | FcγRI-γ |
| CLEC12A | CD137/41BB | b2c | FcγRIII-γ |
| CLEC12A | CD137/41BB | b2c | FcεRIβ |
| CLEC12A | CD137/41BB | b2c | FcεRIγ |
| CLEC12A | CD137/41BB | b2c | DAP10 |
| CLEC12A | CD137/41BB | b2c | DAP12 |
| CLEC12A | CD137/41BB | b2c | CD32 |
| CLEC12A | CD137/41BB | b2c | CD79a |
| CLEC12A | CD137/41BB | b2c | CD79b |
| CLEC12A | CD137/41BB | CD137/41BB | CD8 |
| CLEC12A | CD137/41BB | CD137/41BB | CD3ζ |
| CLEC12A | CD137/41BB | CD137/41BB | CD3δ |
| CLEC12A | CD137/41BB | CD137/41BB | CD3γ |
| CLEC12A | CD137/41BB | CD137/41BB | CD3ε |
| CLEC12A | CD137/41BB | CD137/41BB | FcγRI-γ |
| CLEC12A | CD137/41BB | CD137/41BB | FcγRIII-γ |
| CLEC12A | CD137/41BB | CD137/41BB | FcεRIβ |
| CLEC12A | CD137/41BB | CD137/41BB | FcεRIγ |
| CLEC12A | CD137/41BB | CD137/41BB | DAP10 |
| CLEC12A | CD137/41BB | CD137/41BB | DAP12 |
| CLEC12A | CD137/41BB | CD137/41BB | CD32 |
| CLEC12A | CD137/41BB | CD137/41BB | CD79a |
| CLEC12A | CD137/41BB | CD137/41BB | CD79b |
| CLEC12A | CD137/41BB | ICOS | CD8 |
| CLEC12A | CD137/41BB | ICOS | CD3ζ |
| CLEC12A | CD137/41BB | ICOS | CD3δ |
| CLEC12A | CD137/41BB | ICOS | CD3γ |
| CLEC12A | CD137/41BB | ICOS | CD3ε |
| CLEC12A | CD137/41BB | ICOS | FcγRI-γ |
| CLEC12A | CD137/41BB | ICOS | FcγRIII-γ |
| CLEC12A | CD137/41BB | ICOS | FcεRIβ |
| CLEC12A | CD137/41BB | ICOS | FcεRIγ |
| CLEC12A | CD137/41BB | ICOS | DAP10 |
| CLEC12A | CD137/41BB | ICOS | DAP12 |
| CLEC12A | CD137/41BB | ICOS | CD32 |
| CLEC12A | CD137/41BB | ICOS | CD79a |
| CLEC12A | CD137/41BB | ICOS | CD79b |
| CLEC12A | CD137/41BB | CD27 | CD8 |
| CLEC12A | CD137/41BB | CD27 | CD3ζ |
| CLEC12A | CD137/41BB | CD27 | CD3δ |
| CLEC12A | CD137/41BB | CD27 | CD3ε |
| CLEC12A | CD137/41BB | CD27 | FcγRI-γ |
| CLEC12A | CD137/41BB | CD27 | FcγRIII-γ |
| CLEC12A | CD137/41BB | CD27 | FcεRIβ |
| CLEC12A | CD137/41BB | CD27 | FcεRIγ |
| CLEC12A | CD137/41BB | CD27 | DAP10 |
| CLEC12A | CD137/41BB | CD27 | DAP12 |
| CLEC12A | CD137/41BB | CD27 | CD32 |
| CLEC12A | CD137/41BB | CD27 | CD79a |
| CLEC12A | CD137/41BB | CD27 | CD79b |
| CLEC12A | CD137/41BB | CD28δ | CD8 |
| CLEC12A | CD137/41BB | CD28δ | CD3ζ |
| CLEC12A | CD137/41BB | CD28δ | CD3δ |
| CLEC12A | CD137/41BB | CD28δ | CD3ε |
| CLEC12A | CD137/41BB | CD28δ | FcγRI-γ |
| CLEC12A | CD137/41BB | CD28δ | FcγRIII-γ |
| CLEC12A | CD137/41BB | CD28δ | FcεRIβ |
| CLEC12A | CD137/41BB | CD28δ | FcεRIγ |
| CLEC12A | CD137/41BB | CD28δ | DAP10 |
| CLEC12A | CD137/41BB | CD28δ | DAP12 |
| CLEC12A | CD137/41BB | CD28δ | CD32 |
| CLEC12A | CD137/41BB | CD28δ | CD79a |
| CLEC12A | CD137/41BB | CD28δ | CD79b |
| CLEC12A | CD137/41BB | CD80 | CD8 |
| CLEC12A | CD137/41BB | CD80 | CD3ζ |
| CLEC12A | CD137/41BB | CD80 | CD3δ |
| CLEC12A | CD137/41BB | CD80 | CD3γ |
| CLEC12A | CD137/41BB | CD80 | CD3ε |
| CLEC12A | CD137/41BB | CD80 | FcγRI-γ |
| CLEC12A | CD137/41BB | CD80 | FcγRIII-γ |
| CLEC12A | CD137/41BB | CD80 | FcεRIβ |
| CLEC12A | CD137/41BB | CD80 | FcεRIγ |
| CLEC12A | CD137/41BB | CD80 | DAP10 |
| CLEC12A | CD137/41BB | CD80 | DAP12 |
| CLEC12A | CD137/41BB | CD80 | CD32 |
| CLEC12A | CD137/41BB | CD80 | CD79a |
| CLEC12A | CD137/41BB | CD80 | CD79b |
| CLEC12A | CD137/41BB | CD86 | CD8 |
| CLEC12A | CD137/41BB | CD86 | CD3ζ |
| CLEC12A | CD137/41BB | CD86 | CD3δ |
| CLEC12A | CD137/41BB | CD86 | CD3γ |
| CLEC12A | CD137/41BB | CD86 | CD3ε |
| CLEC12A | CD137/41BB | CD86 | FcγRI-γ |
| CLEC12A | CD137/41BB | CD86 | FcγRIII-γ |
| CLEC12A | CD137/41BB | CD86 | FcεRIβ |
| CLEC12A | CD137/41BB | CD86 | FcεRIγ |
| CLEC12A | CD137/41BB | CD86 | DAP10 |
| CLEC12A | CD137/41BB | CD86 | DAP12 |
| CLEC12A | CD137/41BB | CD86 | CD32 |
| CLEC12A | CD137/41BB | CD86 | CD79a |
| CLEC12A | CD137/41BB | CD86 | CD79b |
| CLEC12A | CD137/41BB | OX40 | CD8 |
| CLEC12A | CD137/41BB | OX40 | CD3ζ |
| CLEC12A | CD137/41BB | OX40 | CD3δ |
| CLEC12A | CD137/41BB | OX40 | CD3γ |
| CLEC12A | CD137/41BB | OX40 | CD3ε |
| CLEC12A | CD137/41BB | OX40 | FcγRI-γ |
| CLEC12A | CD137/41BB | OX40 | FcγRIII-γ |
| CLEC12A | CD137/41BB | OX40 | FcεRIβ |
| CLEC12A | CD137/41BB | OX40 | FcεRIγ |
| CLEC12A | CD137/41BB | OX40 | DAP10 |

TABLE 3-continued

Third Generation CARs

| ScFv | Co-stimulatory Signal | Co-stimulatory Signal | Signal Domain |
|---|---|---|---|
| CLEC12A | CD137/41BB | OX40 | DAP12 |
| CLEC12A | CD137/41BB | OX40 | CD32 |
| CLEC12A | CD137/41BB | OX40 | CD79a |
| CLEC12A | CD137/41BB | OX40 | CD79b |
| CLEC12A | CD137/41BB | DAP10 | CD8 |
| CLEC12A | CD137/41BB | DAP10 | CD3ζ |
| CLEC12A | CD137/41BB | DAP10 | CD3δ |
| CLEC12A | CD137/41BB | DAP10 | CD3γ |
| CLEC12A | CD137/41BB | DAP10 | CD3ε |
| CLEC12A | CD137/41BB | DAP10 | FcγRI-γ |
| CLEC12A | CD137/41BB | DAP10 | FcγRIII-γ |
| CLEC12A | CD137/41BB | DAP10 | FcεRIβ |
| CLEC12A | CD137/41BB | DAP10 | FcεRIγ |
| CLEC12A | CD137/41BB | DAP10 | DAP10 |
| CLEC12A | CD137/41BB | DAP10 | DAP12 |
| CLEC12A | CD137/41BB | DAP10 | CD32 |
| CLEC12A | CD137/41BB | DAP10 | CD79a |
| CLEC12A | CD137/41BB | DAP10 | CD79b |
| CLEC12A | CD137/41BB | DAP12 | CD8 |
| CLEC12A | CD137/41BB | DAP12 | CD3ζ |
| CLEC12A | CD137/41BB | DAP12 | CD3δ |
| CLEC12A | CD137/41BB | DAP12 | CD3γ |
| CLEC12A | CD137/41BB | DAP12 | CD3ε |
| CLEC12A | CD137/41BB | DAP12 | FcγRI-γ |
| CLEC12A | CD137/41BB | DAP12 | FcγRIII-γ |
| CLEC12A | CD137/41BB | DAP12 | FcεRIβ |
| CLEC12A | CD137/41BB | DAP12 | FcεRIγ |
| CLEC12A | CD137/41BB | DAP12 | DAP10 |
| CLEC12A | CD137/41BB | DAP12 | DAP12 |
| CLEC12A | CD137/41BB | DAP12 | CD32 |
| CLEC12A | CD137/41BB | DAP12 | CD79a |
| CLEC12A | CD137/41BB | DAP12 | CD79b |
| CLEC12A | CD137/41BB | MyD88 | CD8 |
| CLEC12A | CD137/41BB | MyD88 | CD3ζ |
| CLEC12A | CD137/41BB | MyD88 | CD3δ |
| CLEC12A | CD137/41BB | MyD88 | CD3γ |
| CLEC12A | CD137/41BB | MyD88 | CD3ε |
| CLEC12A | CD137/41BB | MyD88 | FcγRI-γ |
| CLEC12A | CD137/41BB | MyD88 | FcγRIII-γ |
| CLEC12A | CD137/41BB | MyD88 | FcεRIβ |
| CLEC12A | CD137/41BB | MyD88 | FcεRIγ |
| CLEC12A | CD137/41BB | MyD88 | DAP10 |
| CLEC12A | CD137/41BB | MyD88 | DAP12 |
| CLEC12A | CD137/41BB | MyD88 | CD32 |
| CLEC12A | CD137/41BB | MyD88 | CD79a |
| CLEC12A | CD137/41BB | MyD88 | CD79b |
| CLEC12A | CD137/41BB | CD7 | CD8 |
| CLEC12A | CD137/41BB | CD7 | CD3ζ |
| CLEC12A | CD137/41BB | CD7 | CD3δ |
| CLEC12A | CD137/41BB | CD7 | CD3γ |
| CLEC12A | CD137/41BB | CD7 | CD3ε |
| CLEC12A | CD137/41BB | CD7 | FcγRI-γ |
| CLEC12A | CD137/41BB | CD7 | FcγRIII-γ |
| CLEC12A | CD137/41BB | CD7 | FcεRIβ |
| CLEC12A | CD137/41BB | CD7 | FcεRIγ |
| CLEC12A | CD137/41BB | CD7 | DAP10 |
| CLEC12A | CD137/41BB | CD7 | DAP12 |
| CLEC12A | CD137/41BB | CD7 | CD32 |
| CLEC12A | CD137/41BB | CD7 | CD79a |
| CLEC12A | CD137/41BB | CD7 | CD79b |
| CLEC12A | CD137/41BB | BTNL3 | CD8 |
| CLEC12A | CD137/41BB | BTNL3 | CD3ζ |
| CLEC12A | CD137/41BB | BTNL3 | CD3δ |
| CLEC12A | CD137/41BB | BTNL3 | CD3γ |
| CLEC12A | CD137/41BB | BTNL3 | CD3ε |
| CLEC12A | CD137/41BB | BTNL3 | FcγRI-γ |
| CLEC12A | CD137/41BB | BTNL3 | FcγRIII-γ |
| CLEC12A | CD137/41BB | BTNL3 | FcεRIβ |
| CLEC12A | CD137/41BB | BTNL3 | FcεRIγ |
| CLEC12A | CD137/41BB | BTNL3 | DAP10 |
| CLEC12A | CD137/41BB | BTNL3 | DAP12 |
| CLEC12A | CD137/41BB | BTNL3 | CD32 |
| CLEC12A | CD137/41BB | BTNL3 | CD79a |
| CLEC12A | CD137/41BB | BTNL3 | CD79b |
| CLEC12A | CD137/41BB | NKG2D | CD8 |
| CLEC12A | CD137/41BB | NKG2D | CD3ζ |
| CLEC12A | CD137/41BB | NKG2D | CD3δ |
| CLEC12A | CD137/41BB | NKG2D | CD3γ |
| CLEC12A | CD137/41BB | NKG2D | CD3ε |
| CLEC12A | CD137/41BB | NKG2D | FcγRI-γ |
| CLEC12A | CD137/41BB | NKG2D | FcγRIII-γ |
| CLEC12A | CD137/41BB | NKG2D | FcεRIβ |
| CLEC12A | CD137/41BB | NKG2D | FcεRIγ |
| CLEC12A | CD137/41BB | NKG2D | DAP10 |
| CLEC12A | CD137/41BB | NKG2D | DAP12 |
| CLEC12A | CD137/41BB | NKG2D | CD32 |
| CLEC12A | CD137/41BB | NKG2D | CD79a |
| CLEC12A | CD137/41BB | NKG2D | CD79b |
| CLEC12A | ICOS | CD28 | CD8 |
| CLEC12A | ICOS | CD28 | CD3ζ |
| CLEC12A | ICOS | CD28 | CD3δ |
| CLEC12A | ICOS | CD28 | CD3γ |
| CLEC12A | ICOS | CD28 | CD3ε |
| CLEC12A | ICOS | CD28 | FcγRI-γ |
| CLEC12A | ICOS | CD28 | FcγRIII-γ |
| CLEC12A | ICOS | CD28 | FcεRIβ |
| CLEC12A | ICOS | CD28 | FcεRIγ |
| CLEC12A | ICOS | CD28 | DAP10 |
| CLEC12A | ICOS | CD28 | DAP12 |
| CLEC12A | ICOS | CD28 | CD32 |
| CLEC12A | ICOS | CD28 | CD79a |
| CLEC12A | ICOS | CD28 | CD79b |
| CLEC12A | ICOS | CD8 | CD8 |
| CLEC12A | ICOS | CD8 | CD3ζ |
| CLEC12A | ICOS | CD8 | CD3δ |
| CLEC12A | ICOS | CD8 | CD3γ |
| CLEC12A | ICOS | CD8 | CD3ε |
| CLEC12A | ICOS | CD8 | FcγRI-γ |
| CLEC12A | ICOS | CD8 | FcγRIII-γ |
| CLEC12A | ICOS | CD8 | FcεRIβ |
| CLEC12A | ICOS | CD8 | FcεRIγ |
| CLEC12A | ICOS | CD8 | DAP10 |
| CLEC12A | ICOS | CD8 | DAP12 |
| CLEC12A | ICOS | CD8 | CD32 |
| CLEC12A | ICOS | CD8 | CD79a |
| CLEC12A | ICOS | CD8 | CD79b |
| CLEC12A | ICOS | CD4 | CD8 |
| CLEC12A | ICOS | CD4 | CD3ζ |
| CLEC12A | ICOS | CD4 | CD3δ |
| CLEC12A | ICOS | CD4 | CD3γ |
| CLEC12A | ICOS | CD4 | CD3ε |
| CLEC12A | ICOS | CD4 | FcγRI-γ |
| CLEC12A | ICOS | CD4 | FcγRIII-γ |
| CLEC12A | ICOS | CD4 | FcεRIβ |
| CLEC12A | ICOS | CD4 | FcεRIγ |
| CLEC12A | ICOS | CD4 | DAP10 |
| CLEC12A | ICOS | CD4 | DAP12 |
| CLEC12A | ICOS | CD4 | CD32 |
| CLEC12A | ICOS | CD4 | CD79a |
| CLEC12A | ICOS | CD4 | CD79b |
| CLEC12A | ICOS | b2c | CD8 |
| CLEC12A | ICOS | b2c | CD3ζ |
| CLEC12A | ICOS | b2c | CD3δ |
| CLEC12A | ICOS | b2c | CD3γ |
| CLEC12A | ICOS | b2c | CD3ε |
| CLEC12A | ICOS | b2c | FcγRI-γ |
| CLEC12A | ICOS | b2c | FcγRIII-γ |
| CLEC12A | ICOS | b2c | FcεRIβ |
| CLEC12A | ICOS | b2c | FcεRIγ |
| CLEC12A | ICOS | b2c | DAP10 |
| CLEC12A | ICOS | b2c | DAP12 |
| CLEC12A | ICOS | b2c | CD32 |
| CLEC12A | ICOS | b2c | CD79a |
| CLEC12A | ICOS | b2c | CD79b |
| CLEC12A | ICOS | CD137/41BB | CD8 |
| CLEC12A | ICOS | CD137/41BB | CD3ζ |
| CLEC12A | ICOS | CD137/41BB | CD3δ |
| CLEC12A | ICOS | CD137/41BB | CD3γ |
| CLEC12A | ICOS | CD137/41BB | CD3ε |
| CLEC12A | ICOS | CD137/41BB | FcγRI-γ |

TABLE 3-continued

Third Generation CARs

| ScFv | Co-stimulatory Signal | Co-stimulatory Signal | Signal Domain |
|---|---|---|---|
| CLEC12A | ICOS | CD137/41BB | FcγRIII-γ |
| CLEC12A | ICOS | CD137/41BB | FcεRIβ |
| CLEC12A | ICOS | CD137/41BB | FcεRIγ |
| CLEC12A | ICOS | CD137/41BB | DAP10 |
| CLEC12A | ICOS | CD137/41BB | DAP12 |
| CLEC12A | ICOS | CD137/41BB | CD32 |
| CLEC12A | ICOS | CD137/41BB | CD79a |
| CLEC12A | ICOS | CD137/41BB | CD79b |
| CLEC12A | ICOS | ICOS | CD8 |
| CLEC12A | ICOS | ICOS | CD3ζ |
| CLEC12A | ICOS | ICOS | CD3δ |
| CLEC12A | ICOS | ICOS | CD3γ |
| CLEC12A | ICOS | ICOS | CD3ε |
| CLEC12A | ICOS | ICOS | FcγRI-γ |
| CLEC12A | ICOS | ICOS | FcγRIII-γ |
| CLEC12A | ICOS | ICOS | FcεRIβ |
| CLEC12A | ICOS | ICOS | FcεRIγ |
| CLEC12A | ICOS | ICOS | DAP10 |
| CLEC12A | ICOS | ICOS | DAP12 |
| CLEC12A | ICOS | ICOS | CD32 |
| CLEC12A | ICOS | ICOS | CD79a |
| CLEC12A | ICOS | ICOS | CD79b |
| CLEC12A | ICOS | CD27 | CD8 |
| CLEC12A | ICOS | CD27 | CD3ζ |
| CLEC12A | ICOS | CD27 | CD3δ |
| CLEC12A | ICOS | CD27 | CD3γ |
| CLEC12A | ICOS | CD27 | CD3ε |
| CLEC12A | ICOS | CD27 | FcγRI-γ |
| CLEC12A | ICOS | CD27 | FcγRIII-γ |
| CLEC12A | ICOS | CD27 | FcεRIβ |
| CLEC12A | ICOS | CD27 | FcεRIγ |
| CLEC12A | ICOS | CD27 | DAP10 |
| CLEC12A | ICOS | CD27 | DAP12 |
| CLEC12A | ICOS | CD27 | CD32 |
| CLEC12A | ICOS | CD27 | CD79a |
| CLEC12A | ICOS | CD27 | CD79b |
| CLEC12A | ICOS | CD28δ | CD8 |
| CLEC12A | ICOS | CD28δ | CD3ζ |
| CLEC12A | ICOS | CD28δ | CD3δ |
| CLEC12A | ICOS | CD28δ | CD3γ |
| CLEC12A | ICOS | CD28δ | CD3ε |
| CLEC12A | ICOS | CD28δ | FcγRI-γ |
| CLEC12A | ICOS | CD28δ | FcγRIII-γ |
| CLEC12A | ICOS | CD28δ | FcεRIβ |
| CLEC12A | ICOS | CD28δ | FcεRIγ |
| CLEC12A | ICOS | CD28δ | DAP10 |
| CLEC12A | ICOS | CD28δ | DAP12 |
| CLEC12A | ICOS | CD28δ | CD32 |
| CLEC12A | ICOS | CD28δ | CD79a |
| CLEC12A | ICOS | CD28δ | CD79b |
| CLEC12A | ICOS | CD80 | CD8 |
| CLEC12A | ICOS | CD80 | CD3ζ |
| CLEC12A | ICOS | CD80 | CD3δ |
| CLEC12A | ICOS | CD80 | CD3γ |
| CLEC12A | ICOS | CD80 | CD3ε |
| CLEC12A | ICOS | CD80 | FcγRI-γ |
| CLEC12A | ICOS | CD80 | FcγRIII-γ |
| CLEC12A | ICOS | CD80 | FcεRIβ |
| CLEC12A | ICOS | CD80 | FcεRIγ |
| CLEC12A | ICOS | CD80 | DAP10 |
| CLEC12A | ICOS | CD80 | DAP12 |
| CLEC12A | ICOS | CD80 | CD32 |
| CLEC12A | ICOS | CD80 | CD79a |
| CLEC12A | ICOS | CD80 | CD79b |
| CLEC12A | ICOS | CD86 | CD8 |
| CLEC12A | ICOS | CD86 | CD3ζ |
| CLEC12A | ICOS | CD86 | CD3δ |
| CLEC12A | ICOS | CD86 | CD3γ |
| CLEC12A | ICOS | CD86 | CD3ε |
| CLEC12A | ICOS | CD86 | FcγRI-γ |
| CLEC12A | ICOS | CD86 | FcγRIII-γ |
| CLEC12A | ICOS | CD86 | FcεRIβ |
| CLEC12A | ICOS | CD86 | FcεRIγ |
| CLEC12A | ICOS | CD86 | DAP10 |
| CLEC12A | ICOS | CD86 | DAP12 |
| CLEC12A | ICOS | CD86 | CD32 |
| CLEC12A | ICOS | CD86 | CD79a |
| CLEC12A | ICOS | CD86 | CD79b |
| CLEC12A | ICOS | OX40 | CD8 |
| CLEC12A | ICOS | OX40 | CD3ζ |
| CLEC12A | ICOS | OX40 | CD3δ |
| CLEC12A | ICOS | OX40 | CD3γ |
| CLEC12A | ICOS | OX40 | CD3ε |
| CLEC12A | ICOS | OX40 | FcγRI-γ |
| CLEC12A | ICOS | OX40 | FcγRIII-γ |
| CLEC12A | ICOS | OX40 | FcεRIβ |
| CLEC12A | ICOS | OX40 | FcεRIγ |
| CLEC12A | ICOS | OX40 | DAP10 |
| CLEC12A | ICOS | OX40 | DAP12 |
| CLEC12A | ICOS | OX40 | CD32 |
| CLEC12A | ICOS | OX40 | CD79a |
| CLEC12A | ICOS | OX40 | CD79b |
| CLEC12A | ICOS | DAP10 | CD8 |
| CLEC12A | ICOS | DAP10 | CD3ζ |
| CLEC12A | ICOS | DAP10 | CD3δ |
| CLEC12A | ICOS | DAP10 | CD3γ |
| CLEC12A | ICOS | DAP10 | CD3ε |
| CLEC12A | ICOS | DAP10 | FcγRI-γ |
| CLEC12A | ICOS | DAP10 | FcγRIII-γ |
| CLEC12A | ICOS | DAP10 | FcεRIβ |
| CLEC12A | ICOS | DAP10 | FcεRIγ |
| CLEC12A | ICOS | DAP10 | DAP10 |
| CLEC12A | ICOS | DAP10 | DAP12 |
| CLEC12A | ICOS | DAP10 | CD32 |
| CLEC12A | ICOS | DAP10 | CD79a |
| CLEC12A | ICOS | DAP10 | CD79b |
| CLEC12A | ICOS | DAP12 | CD8 |
| CLEC12A | ICOS | DAP12 | CD3ζ |
| CLEC12A | ICOS | DAP12 | CD3δ |
| CLEC12A | ICOS | DAP12 | CD3γ |
| CLEC12A | ICOS | DAP12 | CD3ε |
| CLEC12A | ICOS | DAP12 | FcγRI-γ |
| CLEC12A | ICOS | DAP12 | FcγRIII-γ |
| CLEC12A | ICOS | DAP12 | FcεRIβ |
| CLEC12A | ICOS | DAP12 | FcεRIγ |
| CLEC12A | ICOS | DAP12 | DAP10 |
| CLEC12A | ICOS | DAP12 | DAP12 |
| CLEC12A | ICOS | DAP12 | CD32 |
| CLEC12A | ICOS | DAP12 | CD79a |
| CLEC12A | ICOS | DAP12 | CD79b |
| CLEC12A | ICOS | MyD88 | CD8 |
| CLEC12A | ICOS | MyD88 | CD3ζ |
| CLEC12A | ICOS | MyD88 | CD3δ |
| CLEC12A | ICOS | MyD88 | CD3γ |
| CLEC12A | ICOS | MyD88 | CD3ε |
| CLEC12A | ICOS | MyD88 | FcγRI-γ |
| CLEC12A | ICOS | MyD88 | FcγRIII-γ |
| CLEC12A | ICOS | MyD88 | FcεRIβ |
| CLEC12A | ICOS | MyD88 | FcεRIγ |
| CLEC12A | ICOS | MyD88 | DAP10 |
| CLEC12A | ICOS | MyD88 | DAP12 |
| CLEC12A | ICOS | MyD88 | CD32 |
| CLEC12A | ICOS | MyD88 | CD79a |
| CLEC12A | ICOS | MyD88 | CD79b |
| CLEC12A | ICOS | CD7 | CD8 |
| CLEC12A | ICOS | CD7 | CD3ζ |
| CLEC12A | ICOS | CD7 | CD3δ |
| CLEC12A | ICOS | CD7 | CD3γ |
| CLEC12A | ICOS | CD7 | CD3ε |
| CLEC12A | ICOS | CD7 | FcγRI-γ |
| CLEC12A | ICOS | CD7 | FcγRIII-γ |
| CLEC12A | ICOS | CD7 | FcεRIβ |
| CLEC12A | ICOS | CD7 | FcεRIγ |
| CLEC12A | ICOS | CD7 | DAP10 |
| CLEC12A | ICOS | CD7 | DAP12 |
| CLEC12A | ICOS | CD7 | CD32 |
| CLEC12A | ICOS | CD7 | CD79a |
| CLEC12A | ICOS | CD7 | CD79b |
| CLEC12A | ICOS | BTNL3 | CD8 |
| CLEC12A | ICOS | BTNL3 | CD3ζ |

TABLE 3-continued

Third Generation CARs

| ScFv | Co-stimulatory Signal | Co-stimulatory Signal | Signal Domain |
|---|---|---|---|
| CLEC12A | ICOS | BTNL3 | CD3δ |
| CLEC12A | ICOS | BTNL3 | CD3γ |
| CLEC12A | ICOS | BTNL3 | CD3ε |
| CLEC12A | ICOS | BTNL3 | FcγRI-γ |
| CLEC12A | ICOS | BTNL3 | FcγRIII-γ |
| CLEC12A | ICOS | BTNL3 | FcεRIβ |
| CLEC12A | ICOS | BTNL3 | FcεRIγ |
| CLEC12A | ICOS | BTNL3 | DAP10 |
| CLEC12A | ICOS | BTNL3 | DAP12 |
| CLEC12A | ICOS | BTNL3 | CD32 |
| CLEC12A | ICOS | BTNL3 | CD79a |
| CLEC12A | ICOS | BTNL3 | CD79b |
| CLEC12A | ICOS | NKG2D | CD8 |
| CLEC12A | ICOS | NKG2D | CD3ζ |
| CLEC12A | ICOS | NKG2D | CD3δ |
| CLEC12A | ICOS | NKG2D | CD3γ |
| CLEC12A | ICOS | NKG2D | CD3ε |
| CLEC12A | ICOS | NKG2D | FcγRI-γ |
| CLEC12A | ICOS | NKG2D | FcγRIII-γ |
| CLEC12A | ICOS | NKG2D | FcεRIβ |
| CLEC12A | ICOS | NKG2D | FcεRIγ |
| CLEC12A | ICOS | NKG2D | DAP10 |
| CLEC12A | ICOS | NKG2D | DAP12 |
| CLEC12A | ICOS | NKG2D | CD32 |
| CLEC12A | ICOS | NKG2D | CD79a |
| CLEC12A | ICOS | NKG2D | CD79b |
| CLEC12A | CD27 | CD28 | CD8 |
| CLEC12A | CD27 | CD28 | CD3ζ |
| CLEC12A | CD27 | CD28 | CD3δ |
| CLEC12A | CD27 | CD28 | CD3γ |
| CLEC12A | CD27 | CD28 | CD3ε |
| CLEC12A | CD27 | CD28 | FcγRI-γ |
| CLEC12A | CD27 | CD28 | FcγRIII-γ |
| CLEC12A | CD27 | CD28 | FcεRIβ |
| CLEC12A | CD27 | CD28 | FcεRIγ |
| CLEC12A | CD27 | CD28 | DAP10 |
| CLEC12A | CD27 | CD28 | DAP12 |
| CLEC12A | CD27 | CD28 | CD32 |
| CLEC12A | CD27 | CD28 | CD79a |
| CLEC12A | CD27 | CD28 | CD79b |
| CLEC12A | CD27 | CD8 | CD8 |
| CLEC12A | CD27 | CD8 | CD3ζ |
| CLEC12A | CD27 | CD8 | CD3δ |
| CLEC12A | CD27 | CD8 | CD3γ |
| CLEC12A | CD27 | CD8 | CD3ε |
| CLEC12A | CD27 | CD8 | FcγRI-γ |
| CLEC12A | CD27 | CD8 | FcγRIII-γ |
| CLEC12A | CD27 | CD8 | FcεRIβ |
| CLEC12A | CD27 | CD8 | FcεRIγ |
| CLEC12A | CD27 | CD8 | DAP10 |
| CLEC12A | CD27 | CD8 | DAP12 |
| CLEC12A | CD27 | CD8 | CD32 |
| CLEC12A | CD27 | CD8 | CD79a |
| CLEC12A | CD27 | CD8 | CD79b |
| CLEC12A | CD27 | CD4 | CD8 |
| CLEC12A | CD27 | CD4 | CD3ζ |
| CLEC12A | CD27 | CD4 | CD3δ |
| CLEC12A | CD27 | CD4 | CD3γ |
| CLEC12A | CD27 | CD4 | CD3ε |
| CLEC12A | CD27 | CD4 | FcγRI-γ |
| CLEC12A | CD27 | CD4 | FcγRIII-γ |
| CLEC12A | CD27 | CD4 | FcεRIβ |
| CLEC12A | CD27 | CD4 | FcεRIγ |
| CLEC12A | CD27 | CD4 | DAP10 |
| CLEC12A | CD27 | CD4 | DAP12 |
| CLEC12A | CD27 | CD4 | CD32 |
| CLEC12A | CD27 | CD4 | CD79a |
| CLEC12A | CD27 | CD4 | CD79b |
| CLEC12A | CD27 | b2c | CD8 |
| CLEC12A | CD27 | b2c | CD3ζ |
| CLEC12A | CD27 | b2c | CD3δ |
| CLEC12A | CD27 | b2c | CD3γ |
| CLEC12A | CD27 | b2c | CD3ε |
| CLEC12A | CD27 | b2c | FcγRI-γ |
| CLEC12A | CD27 | b2c | FcγRIII-γ |
| CLEC12A | CD27 | b2c | FcεRIβ |
| CLEC12A | CD27 | b2c | FcεRIγ |
| CLEC12A | CD27 | b2c | DAP10 |
| CLEC12A | CD27 | b2c | DAP12 |
| CLEC12A | CD27 | b2c | CD32 |
| CLEC12A | CD27 | b2c | CD79a |
| CLEC12A | CD27 | b2c | CD79b |
| CLEC12A | CD27 | CD137/41BB | CD8 |
| CLEC12A | CD27 | CD137/41BB | CD3ζ |
| CLEC12A | CD27 | CD137/41BB | CD3δ |
| CLEC12A | CD27 | CD137/41BB | CD3γ |
| CLEC12A | CD27 | CD137/41BB | CD3ε |
| CLEC12A | CD27 | CD137/41BB | FcγRI-γ |
| CLEC12A | CD27 | CD137/41BB | FcγRIII-γ |
| CLEC12A | CD27 | CD137/41BB | FcεRIβ |
| CLEC12A | CD27 | CD137/41BB | FcεRIγ |
| CLEC12A | CD27 | CD137/41BB | DAP10 |
| CLEC12A | CD27 | CD137/41BB | DAP12 |
| CLEC12A | CD27 | CD137/41BB | CD32 |
| CLEC12A | CD27 | CD137/41BB | CD79a |
| CLEC12A | CD27 | CD137/41BB | CD79b |
| CLEC12A | CD27 | ICOS | CD8 |
| CLEC12A | CD27 | ICOS | CD3ζ |
| CLEC12A | CD27 | ICOS | CD3δ |
| CLEC12A | CD27 | ICOS | CD3γ |
| CLEC12A | CD27 | ICOS | CD3ε |
| CLEC12A | CD27 | ICOS | FcγRI-γ |
| CLEC12A | CD27 | ICOS | FcγRIII-γ |
| CLEC12A | CD27 | ICOS | FcεRIβ |
| CLEC12A | CD27 | ICOS | FcεRIγ |
| CLEC12A | CD27 | ICOS | DAP10 |
| CLEC12A | CD27 | ICOS | DAP12 |
| CLEC12A | CD27 | ICOS | CD32 |
| CLEC12A | CD27 | ICOS | CD79a |
| CLEC12A | CD27 | ICOS | CD79b |
| CLEC12A | CD27 | CD27 | CD8 |
| CLEC12A | CD27 | CD27 | CD3ζ |
| CLEC12A | CD27 | CD27 | CD3δ |
| CLEC12A | CD27 | CD27 | CD3γ |
| CLEC12A | CD27 | CD27 | CD3ε |
| CLEC12A | CD27 | CD27 | FcγRI-γ |
| CLEC12A | CD27 | CD27 | FcγRIII-γ |
| CLEC12A | CD27 | CD27 | FcεRIβ |
| CLEC12A | CD27 | CD27 | FcεRIγ |
| CLEC12A | CD27 | CD27 | DAP10 |
| CLEC12A | CD27 | CD27 | DAP12 |
| CLEC12A | CD27 | CD27 | CD32 |
| CLEC12A | CD27 | CD27 | CD79a |
| CLEC12A | CD27 | CD27 | CD79b |
| CLEC12A | CD27 | CD28δ | CD8 |
| CLEC12A | CD27 | CD28δ | CD3ζ |
| CLEC12A | CD27 | CD28δ | CD3δ |
| CLEC12A | CD27 | CD28δ | CD3γ |
| CLEC12A | CD27 | CD28δ | CD3ε |
| CLEC12A | CD27 | CD28δ | FcγRI-γ |
| CLEC12A | CD27 | CD28δ | FcγRIII-γ |
| CLEC12A | CD27 | CD28δ | FcεRIβ |
| CLEC12A | CD27 | CD28δ | FcεRIγ |
| CLEC12A | CD27 | CD28δ | DAP10 |
| CLEC12A | CD27 | CD28δ | DAP12 |
| CLEC12A | CD27 | CD28δ | CD32 |
| CLEC12A | CD27 | CD28δ | CD79a |
| CLEC12A | CD27 | CD28δ | CD79b |
| CLEC12A | CD27 | CD80 | CD8 |
| CLEC12A | CD27 | CD80 | CD3ζ |
| CLEC12A | CD27 | CD80 | CD3δ |
| CLEC12A | CD27 | CD80 | CD3γ |
| CLEC12A | CD27 | CD80 | CD3ε |
| CLEC12A | CD27 | CD80 | FcδRI-δ |
| CLEC12A | CD27 | CD80 | FcγRIII-γ |
| CLEC12A | CD27 | CD80 | FcεRIβ |
| CLEC12A | CD27 | CD80 | FcεRIγ |
| CLEC12A | CD27 | CD80 | DAP10 |
| CLEC12A | CD27 | CD80 | DAP12 |
| CLEC12A | CD27 | CD80 | CD32 |

TABLE 3-continued

Third Generation CARs

| ScFv | Co-stimulatory Signal | Co-stimulatory Signal | Signal Domain |
|---|---|---|---|
| CLEC12A | CD27 | CD80 | CD79a |
| CLEC12A | CD27 | CD80 | CD79b |
| CLEC12A | CD27 | CD86 | CD8 |
| CLEC12A | CD27 | CD86 | CD3ζ |
| CLEC12A | CD27 | CD86 | CD3δ |
| CLEC12A | CD27 | CD86 | CD3γ |
| CLEC12A | CD27 | CD86 | CD3ε |
| CLEC12A | CD27 | CD86 | FcγRI-γ |
| CLEC12A | CD27 | CD86 | FcγRIII-γ |
| CLEC12A | CD27 | CD86 | FcεRIβ |
| CLEC12A | CD27 | CD86 | FcεRIγ |
| CLEC12A | CD27 | CD86 | DAP10 |
| CLEC12A | CD27 | CD86 | DAP12 |
| CLEC12A | CD27 | CD86 | CD32 |
| CLEC12A | CD27 | CD86 | CD79a |
| CLEC12A | CD27 | CD86 | CD79b |
| CLEC12A | CD27 | OX40 | CD8 |
| CLEC12A | CD27 | OX40 | CD3ζ |
| CLEC12A | CD27 | OX40 | CD3δ |
| CLEC12A | CD27 | OX40 | CD3γ |
| CLEC12A | CD27 | OX40 | CD3ε |
| CLEC12A | CD27 | OX40 | FcγRI-γ |
| CLEC12A | CD27 | OX40 | FcγRIII-γ |
| CLEC12A | CD27 | OX40 | FcεRIβ |
| CLEC12A | CD27 | OX40 | FcεRIγ |
| CLEC12A | CD27 | OX40 | DAP10 |
| CLEC12A | CD27 | OX40 | DAP12 |
| CLEC12A | CD27 | OX40 | CD32 |
| CLEC12A | CD27 | OX40 | CD79a |
| CLEC12A | CD27 | OX40 | CD79b |
| CLEC12A | CD27 | DAP10 | CD8 |
| CLEC12A | CD27 | DAP10 | CD3ζ |
| CLEC12A | CD27 | DAP10 | CD3δ |
| CLEC12A | CD27 | DAP10 | CD3γ |
| CLEC12A | CD27 | DAP10 | CD3ε |
| CLEC12A | CD27 | DAP10 | FcγRI-γ |
| CLEC12A | CD27 | DAP10 | FcγRIII-γ |
| CLEC12A | CD27 | DAP10 | FcεRIβ |
| CLEC12A | CD27 | DAP10 | FcεRIγ |
| CLEC12A | CD27 | DAP10 | DAP10 |
| CLEC12A | CD27 | DAP10 | DAP12 |
| CLEC12A | CD27 | DAP10 | CD32 |
| CLEC12A | CD27 | DAP10 | CD79a |
| CLEC12A | CD27 | DAP10 | CD79b |
| CLEC12A | CD27 | DAP12 | CD8 |
| CLEC12A | CD27 | DAP12 | CD3ζ |
| CLEC12A | CD27 | DAP12 | CD3δ |
| CLEC12A | CD27 | DAP12 | CD3γ |
| CLEC12A | CD27 | DAP12 | CD3ε |
| CLEC12A | CD27 | DAP12 | FcγRI-γ |
| CLEC12A | CD27 | DAP12 | FcγRIII-γ |
| CLEC12A | CD27 | DAP12 | FcεRIβ |
| CLEC12A | CD27 | DAP12 | FcεRIγ |
| CLEC12A | CD27 | DAP12 | DAP10 |
| CLEC12A | CD27 | DAP12 | DAP12 |
| CLEC12A | CD27 | DAP12 | CD32 |
| CLEC12A | CD27 | DAP12 | CD79a |
| CLEC12A | CD27 | DAP12 | CD79b |
| CLEC12A | CD27 | MyD88 | CD8 |
| CLEC12A | CD27 | MyD88 | CD3ζ |
| CLEC12A | CD27 | MyD88 | CD3δ |
| CLEC12A | CD27 | MyD88 | CD3γ |
| CLEC12A | CD27 | MyD88 | CD3ε |
| CLEC12A | CD27 | MyD88 | FcγRI-γ |
| CLEC12A | CD27 | MyD88 | FcγRIII-γ |
| CLEC12A | CD27 | MyD88 | FcεRIβ |
| CLEC12A | CD27 | MyD88 | FcεRIγ |
| CLEC12A | CD27 | MyD88 | DAP10 |
| CLEC12A | CD27 | MyD88 | DAP12 |
| CLEC12A | CD27 | MyD88 | CD32 |
| CLEC12A | CD27 | MyD88 | CD79a |
| CLEC12A | CD27 | MyD88 | CD79b |
| CLEC12A | CD27 | CD7 | CD8 |
| CLEC12A | CD27 | CD7 | CD3ζ |
| CLEC12A | CD27 | CD7 | CD3δ |
| CLEC12A | CD27 | CD7 | CD3γ |
| CLEC12A | CD27 | CD7 | CD3ε |
| CLEC12A | CD27 | CD7 | FcγRI-γ |
| CLEC12A | CD27 | CD7 | FcγRIII-γ |
| CLEC12A | CD27 | CD7 | FcεRIβ |
| CLEC12A | CD27 | CD7 | FcεRIγ |
| CLEC12A | CD27 | CD7 | DAP10 |
| CLEC12A | CD27 | CD7 | DAP12 |
| CLEC12A | CD27 | CD7 | CD32 |
| CLEC12A | CD27 | CD7 | CD79a |
| CLEC12A | CD27 | CD7 | CD79b |
| CLEC12A | CD27 | BTNL3 | CD8 |
| CLEC12A | CD27 | BTNL3 | CD3ζ |
| CLEC12A | CD27 | BTNL3 | CD3δ |
| CLEC12A | CD27 | BTNL3 | CD3γ |
| CLEC12A | CD27 | BTNL3 | CD3ε |
| CLEC12A | CD27 | BTNL3 | FcγRI-γ |
| CLEC12A | CD27 | BTNL3 | FcγRIII-γ |
| CLEC12A | CD27 | BTNL3 | FcεRIβ |
| CLEC12A | CD27 | BTNL3 | FcεRIγ |
| CLEC12A | CD27 | BTNL3 | DAP10 |
| CLEC12A | CD27 | BTNL3 | DAP12 |
| CLEC12A | CD27 | BTNL3 | CD32 |
| CLEC12A | CD27 | BTNL3 | CD79a |
| CLEC12A | CD27 | BTNL3 | CD79b |
| CLEC12A | CD27 | NKG2D | CD8 |
| CLEC12A | CD27 | NKG2D | CD3ζ |
| CLEC12A | CD27 | NKG2D | CD3δ |
| CLEC12A | CD27 | NKG2D | CD3γ |
| CLEC12A | CD27 | NKG2D | CD3ε |
| CLEC12A | CD27 | NKG2D | FcγRI-γ |
| CLEC12A | CD27 | NKG2D | FcγRIII-γ |
| CLEC12A | CD27 | NKG2D | FcεRIβ |
| CLEC12A | CD27 | NKG2D | FcεRIγ |
| CLEC12A | CD27 | NKG2D | DAP10 |
| CLEC12A | CD27 | NKG2D | DAP12 |
| CLEC12A | CD27 | NKG2D | CD32 |
| CLEC12A | CD27 | NKG2D | CD79a |
| CLEC12A | CD27 | NKG2D | CD79b |
| CLEC12A | CD28δ | CD28 | CD8 |
| CLEC12A | CD28δ | CD28 | CD3ζ |
| CLEC12A | CD28δ | CD28 | CD3δ |
| CLEC12A | CD28δ | CD28 | CD3γ |
| CLEC12A | CD28δ | CD28 | CD3ε |
| CLEC12A | CD28δ | CD28 | FcγRI-γ |
| CLEC12A | CD28δ | CD28 | FcγRIII-γ |
| CLEC12A | CD28δ | CD28 | FcεRIβ |
| CLEC12A | CD28δ | CD28 | FcεRIγ |
| CLEC12A | CD28δ | CD28 | DAP10 |
| CLEC12A | CD28δ | CD28 | DAP12 |
| CLEC12A | CD28δ | CD28 | CD32 |
| CLEC12A | CD28δ | CD28 | CD79a |
| CLEC12A | CD28δ | CD28 | CD79b |
| CLEC12A | CD28δ | CD8 | CD8 |
| CLEC12A | CD28δ | CD8 | CD3ζ |
| CLEC12A | CD28δ | CD8 | CD3δ |
| CLEC12A | CD28δ | CD8 | CD3γ |
| CLEC12A | CD28δ | CD8 | CD3ε |
| CLEC12A | CD28δ | CD8 | FcγRI-γ |
| CLEC12A | CD28δ | CD8 | FcγRIII-γ |
| CLEC12A | CD28δ | CD8 | FcεRIβ |
| CLEC12A | CD28δ | CD8 | FcεRIγ |
| CLEC12A | CD28δ | CD8 | DAP10 |
| CLEC12A | CD28δ | CD8 | DAP12 |
| CLEC12A | CD28δ | CD8 | CD32 |
| CLEC12A | CD28δ | CD8 | CD79a |
| CLEC12A | CD28δ | CD8 | CD79b |
| CLEC12A | CD28δ | CD4 | CD8 |
| CLEC12A | CD28δ | CD4 | CD3ζ |
| CLEC12A | CD28δ | CD4 | CD3δ |
| CLEC12A | CD28δ | CD4 | CD3γ |
| CLEC12A | CD28δ | CD4 | CD3ε |
| CLEC12A | CD28δ | CD4 | FcγRI-γ |
| CLEC12A | CD28δ | CD4 | FcγRIII-γ |
| CLEC12A | CD28δ | CD4 | FcεRIβ |

TABLE 3-continued

Third Generation CARs

| ScFv | Co-stimulatory Signal | Co-stimulatory Signal | Signal Domain |
|---|---|---|---|
| CLEC12A | CD28δ | CD4 | FcεRIγ |
| CLEC12A | CD28δ | CD4 | DAP10 |
| CLEC12A | CD28δ | CD4 | DAP12 |
| CLEC12A | CD28δ | CD4 | CD32 |
| CLEC12A | CD28δ | CD4 | CD79a |
| CLEC12A | CD28δ | CD4 | CD79b |
| CLEC12A | CD28δ | b2c | CD8 |
| CLEC12A | CD28δ | b2c | CD3ζ |
| CLEC12A | CD28δ | b2c | CD3δ |
| CLEC12A | CD28δ | b2c | CD3γ |
| CLEC12A | CD28δ | b2c | CD3ε |
| CLEC12A | CD28δ | b2c | FcγRI-γ |
| CLEC12A | CD28δ | b2c | FcγRIII-γ |
| CLEC12A | CD28δ | b2c | FcεRIβ |
| CLEC12A | CD28δ | b2c | FcεRIγ |
| CLEC12A | CD28δ | b2c | DAP10 |
| CLEC12A | CD28δ | b2c | DAP12 |
| CLEC12A | CD28δ | b2c | CD32 |
| CLEC12A | CD28δ | b2c | CD79a |
| CLEC12A | CD28δ | b2c | CD79b |
| CLEC12A | CD28δ | CD137/41BB | CD8 |
| CLEC12A | CD28δ | CD137/41BB | CD3ζ |
| CLEC12A | CD28δ | CD137/41BB | CD3δ |
| CLEC12A | CD28δ | CD137/41BB | CD3γ |
| CLEC12A | CD28δ | CD137/41BB | CD3ε |
| CLEC12A | CD28δ | CD137/41BB | FcγRI-γ |
| CLEC12A | CD28δ | CD137/41BB | FcγRIII-γ |
| CLEC12A | CD28δ | CD137/41BB | FcεRIβ |
| CLEC12A | CD28δ | CD137/41BB | FcεRIγ |
| CLEC12A | CD28δ | CD137/41BB | DAP10 |
| CLEC12A | CD28δ | CD137/41BB | DAP12 |
| CLEC12A | CD28δ | CD137/41BB | CD32 |
| CLEC12A | CD28δ | CD137/41BB | CD79a |
| CLEC12A | CD28δ | CD137/41BB | CD79b |
| CLEC12A | CD28δ | ICOS | CD8 |
| CLEC12A | CD28δ | ICOS | CD3ζ |
| CLEC12A | CD28δ | ICOS | CD3δ |
| CLEC12A | CD28δ | ICOS | CD3γ |
| CLEC12A | CD28δ | ICOS | CD3ε |
| CLEC12A | CD28δ | ICOS | FcγRI-γ |
| CLEC12A | CD28δ | ICOS | FcγRIII-γ |
| CLEC12A | CD28δ | ICOS | FcεRIβ |
| CLEC12A | CD28δ | ICOS | FcεRIγ |
| CLEC12A | CD28δ | ICOS | DAP10 |
| CLEC12A | CD28δ | ICOS | DAP12 |
| CLEC12A | CD28δ | ICOS | CD32 |
| CLEC12A | CD28δ | ICOS | CD79a |
| CLEC12A | CD28δ | ICOS | CD79b |
| CLEC12A | CD28δ | CD27 | CD8 |
| CLEC12A | CD28δ | CD27 | CD3ζ |
| CLEC12A | CD28δ | CD27 | CD3δ |
| CLEC12A | CD28δ | CD27 | CD3γ |
| CLEC12A | CD28δ | CD27 | CD3ε |
| CLEC12A | CD28δ | CD27 | FcγRI-γ |
| CLEC12A | CD28δ | CD27 | FcγRIII-γ |
| CLEC12A | CD28δ | CD27 | FcεRIβ |
| CLEC12A | CD28δ | CD27 | FcεRIγ |
| CLEC12A | CD28δ | CD27 | DAP10 |
| CLEC12A | CD28δ | CD27 | DAP12 |
| CLEC12A | CD28δ | CD27 | CD32 |
| CLEC12A | CD28δ | CD27 | CD79a |
| CLEC12A | CD28δ | CD27 | CD79b |
| CLEC12A | CD28δ | CD28δ | CD8 |
| CLEC12A | CD28δ | CD28δ | CD3ζ |
| CLEC12A | CD28δ | CD28δ | CD3δ |
| CLEC12A | CD28δ | CD28δ | CD3γ |
| CLEC12A | CD28δ | CD28δ | CD3ε |
| CLEC12A | CD28δ | CD28δ | FcγRI-γ |
| CLEC12A | CD28δ | CD28δ | FcγRIII-γ |
| CLEC12A | CD28δ | CD28δ | FcεRIβ |
| CLEC12A | CD28δ | CD28δ | FcεRIγ |
| CLEC12A | CD28δ | CD28δ | DAP10 |
| CLEC12A | CD28δ | CD28δ | DAP12 |
| CLEC12A | CD28δ | CD28δ | CD32 |
| CLEC12A | CD28δ | CD28δ | CD79a |
| CLEC12A | CD28δ | CD28δ | CD79b |
| CLEC12A | CD28δ | CD80 | CD8 |
| CLEC12A | CD28δ | CD80 | CD3ζ |
| CLEC12A | CD28δ | CD80 | CD3δ |
| CLEC12A | CD28δ | CD80 | CD3γ |
| CLEC12A | CD28δ | CD80 | CD3ε |
| CLEC12A | CD28δ | CD80 | FcγRI-γ |
| CLEC12A | CD28δ | CD80 | FcγRIII-γ |
| CLEC12A | CD28δ | CD80 | FcεRIβ |
| CLEC12A | CD28δ | CD80 | FcεRIγ |
| CLEC12A | CD28δ | CD80 | DAP10 |
| CLEC12A | CD28δ | CD80 | DAP12 |
| CLEC12A | CD28δ | CD80 | CD32 |
| CLEC12A | CD28δ | CD80 | CD79a |
| CLEC12A | CD28δ | CD80 | CD79b |
| CLEC12A | CD28δ | CD86 | CD8 |
| CLEC12A | CD28δ | CD86 | CD3ζ |
| CLEC12A | CD28δ | CD86 | CD3δ |
| CLEC12A | CD28δ | CD86 | CD3γ |
| CLEC12A | CD28δ | CD86 | CD3ε |
| CLEC12A | CD28δ | CD86 | FcγRI-γ |
| CLEC12A | CD28δ | CD86 | FcγRIII-γ |
| CLEC12A | CD28δ | CD86 | FcεRIβ |
| CLEC12A | CD28δ | CD86 | FcεRIγ |
| CLEC12A | CD28δ | CD86 | DAP10 |
| CLEC12A | CD28δ | CD86 | DAP12 |
| CLEC12A | CD28δ | CD86 | CD32 |
| CLEC12A | CD28δ | CD86 | CD79a |
| CLEC12A | CD28δ | CD86 | CD79b |
| CLEC12A | CD28δ | OX40 | CD8 |
| CLEC12A | CD28δ | OX40 | CD3ζ |
| CLEC12A | CD28δ | OX40 | CD3δ |
| CLEC12A | CD28δ | OX40 | CD3γ |
| CLEC12A | CD28δ | OX40 | CD3ε |
| CLEC12A | CD28δ | OX40 | FcγRI-γ |
| CLEC12A | CD28δ | OX40 | FcγRIII-γ |
| CLEC12A | CD28δ | OX40 | FcεRIβ |
| CLEC12A | CD28δ | OX40 | FcεRIγ |
| CLEC12A | CD28δ | OX40 | DAP10 |
| CLEC12A | CD28δ | OX40 | DAP12 |
| CLEC12A | CD28δ | OX40 | CD32 |
| CLEC12A | CD28δ | OX40 | CD79a |
| CLEC12A | CD28δ | OX40 | CD79b |
| CLEC12A | CD28δ | DAP10 | CD8 |
| CLEC12A | CD28δ | DAP10 | CD3ζ |
| CLEC12A | CD28δ | DAP10 | CD3δ |
| CLEC12A | CD28δ | DAP10 | CD3γ |
| CLEC12A | CD28δ | DAP10 | CD3ε |
| CLEC12A | CD28δ | DAP10 | FcγRI-γ |
| CLEC12A | CD28δ | DAP10 | FcγRIII-γ |
| CLEC12A | CD28δ | DAP10 | FcεRIβ |
| CLEC12A | CD28δ | DAP10 | FcεRIγ |
| CLEC12A | CD28δ | DAP10 | DAP10 |
| CLEC12A | CD28δ | DAP10 | DAP12 |
| CLEC12A | CD28δ | DAP10 | CD32 |
| CLEC12A | CD28δ | DAP10 | CD79a |
| CLEC12A | CD28δ | DAP10 | CD79b |
| CLEC12A | CD28δ | DAP12 | CD8 |
| CLEC12A | CD28δ | DAP12 | CD3ζ |
| CLEC12A | CD28δ | DAP12 | CD3δ |
| CLEC12A | CD28δ | DAP12 | CD3γ |
| CLEC12A | CD28δ | DAP12 | CD3ε |
| CLEC12A | CD28δ | DAP12 | FcγRI-γ |
| CLEC12A | CD28δ | DAP12 | FcγRIII-γ |
| CLEC12A | CD28δ | DAP12 | FcεRIβ |
| CLEC12A | CD28δ | DAP12 | FcεRIγ |
| CLEC12A | CD28δ | DAP12 | DAP10 |
| CLEC12A | CD28δ | DAP12 | DAP12 |
| CLEC12A | CD28δ | DAP12 | CD32 |
| CLEC12A | CD28δ | DAP12 | CD79a |
| CLEC12A | CD28δ | DAP12 | CD79b |
| CLEC12A | CD28δ | MyD88 | CD8 |
| CLEC12A | CD28δ | MyD88 | CD3ζ |
| CLEC12A | CD28δ | MyD88 | CD3δ |
| CLEC12A | CD28δ | MyD88 | CD3γ |

TABLE 3-continued

Third Generation CARs

| ScFv | Co-stimulatory Signal | Co-stimulatory Signal | Signal Domain |
|---|---|---|---|
| CLEC12A | CD28δ | MyD88 | CD3ε |
| CLEC12A | CD28δ | MyD88 | FcγRI-γ |
| CLEC12A | CD28δ | MyD88 | FcγRIII-γ |
| CLEC12A | CD28δ | MyD88 | FcεRIβ |
| CLEC12A | CD28δ | MyD88 | FcεRIγ |
| CLEC12A | CD28δ | MyD88 | DAP10 |
| CLEC12A | CD28δ | MyD88 | DAP12 |
| CLEC12A | CD28δ | MyD88 | CD32 |
| CLEC12A | CD28δ | MyD88 | CD79a |
| CLEC12A | CD28δ | MyD88 | CD79b |
| CLEC12A | CD28δ | CD7 | CD8 |
| CLEC12A | CD28δ | CD7 | CD3ζ |
| CLEC12A | CD28δ | CD7 | CD3δ |
| CLEC12A | CD28δ | CD7 | CD3γ |
| CLEC12A | CD28δ | CD7 | CD3ε |
| CLEC12A | CD28δ | CD7 | FcγRI-γ |
| CLEC12A | CD28δ | CD7 | FcγRIII-γ |
| CLEC12A | CD28δ | CD7 | FcεRIβ |
| CLEC12A | CD28δ | CD7 | FcεRIγ |
| CLEC12A | CD28δ | CD7 | DAP10 |
| CLEC12A | CD28δ | CD7 | DAP12 |
| CLEC12A | CD28δ | CD7 | CD32 |
| CLEC12A | CD28δ | CD7 | CD79a |
| CLEC12A | CD28δ | CD7 | CD79b |
| CLEC12A | CD28δ | BTNL3 | CD8 |
| CLEC12A | CD28δ | BTNL3 | CD3ζ |
| CLEC12A | CD28δ | BTNL3 | CD3δ |
| CLEC12A | CD28δ | BTNL3 | CD3γ |
| CLEC12A | CD28δ | BTNL3 | CD3ε |
| CLEC12A | CD28δ | BTNL3 | FcγRI-γ |
| CLEC12A | CD28δ | BTNL3 | FcγRIII-γ |
| CLEC12A | CD28δ | BTNL3 | FcεRIβ |
| CLEC12A | CD28δ | BTNL3 | FcεRIγ |
| CLEC12A | CD28δ | BTNL3 | DAP10 |
| CLEC12A | CD28δ | BTNL3 | DAP12 |
| CLEC12A | CD28δ | BTNL3 | CD32 |
| CLEC12A | CD28δ | BTNL3 | CD79a |
| CLEC12A | CD28δ | BTNL3 | CD79b |
| CLEC12A | CD28δ | NKG2D | CD8 |
| CLEC12A | CD28δ | NKG2D | CD3ζ |
| CLEC12A | CD28δ | NKG2D | CD3δ |
| CLEC12A | CD28δ | NKG2D | CD3γ |
| CLEC12A | CD28δ | NKG2D | CD3ε |
| CLEC12A | CD28δ | NKG2D | FcγRI-γ |
| CLEC12A | CD28δ | NKG2D | FcγRIII-γ |
| CLEC12A | CD28δ | NKG2D | FcεRIβ |
| CLEC12A | CD28δ | NKG2D | FcεRIγ |
| CLEC12A | CD28δ | NKG2D | DAP10 |
| CLEC12A | CD28δ | NKG2D | DAP12 |
| CLEC12A | CD28δ | NKG2D | CD32 |
| CLEC12A | CD28δ | NKG2D | CD79a |
| CLEC12A | CD28δ | NKG2D | CD79b |
| CLEC12A | CD80 | CD28 | CD8 |
| CLEC12A | CD80 | CD28 | CD3ζ |
| CLEC12A | CD80 | CD28 | CD3δ |
| CLEC12A | CD80 | CD28 | CD3γ |
| CLEC12A | CD80 | CD28 | CD3ε |
| CLEC12A | CD80 | CD28 | FcγRI-γ |
| CLEC12A | CD80 | CD28 | FcγRIII-γ |
| CLEC12A | CD80 | CD28 | FcεRIβ |
| CLEC12A | CD80 | CD28 | FcεRIγ |
| CLEC12A | CD80 | CD28 | DAP10 |
| CLEC12A | CD80 | CD28 | DAP12 |
| CLEC12A | CD80 | CD28 | CD32 |
| CLEC12A | CD80 | CD28 | CD79a |
| CLEC12A | CD80 | CD28 | CD79b |
| CLEC12A | CD80 | CD8 | CD8 |
| CLEC12A | CD80 | CD8 | CD3ζ |
| CLEC12A | CD80 | CD8 | CD3δ |
| CLEC12A | CD80 | CD8 | CD3γ |
| CLEC12A | CD80 | CD8 | CD3ε |
| CLEC12A | CD80 | CD8 | FcγRI-γ |
| CLEC12A | CD80 | CD8 | FcγRIII-γ |
| CLEC12A | CD80 | CD8 | FcεRIβ |
| CLEC12A | CD80 | CD8 | FcεRIγ |
| CLEC12A | CD80 | CD8 | DAP10 |
| CLEC12A | CD80 | CD8 | DAP12 |
| CLEC12A | CD80 | CD8 | CD32 |
| CLEC12A | CD80 | CD8 | CD79a |
| CLEC12A | CD80 | CD8 | CD79b |
| CLEC12A | CD80 | CD4 | CD8 |
| CLEC12A | CD80 | CD4 | CD3ζ |
| CLEC12A | CD80 | CD4 | CD3δ |
| CLEC12A | CD80 | CD4 | CD3γ |
| CLEC12A | CD80 | CD4 | CD3ε |
| CLEC12A | CD80 | CD4 | FcγRI-γ |
| CLEC12A | CD80 | CD4 | FcγRIII-γ |
| CLEC12A | CD80 | CD4 | FcεRIβ |
| CLEC12A | CD80 | CD4 | FcεRIγ |
| CLEC12A | CD80 | CD4 | DAP10 |
| CLEC12A | CD80 | CD4 | DAP12 |
| CLEC12A | CD80 | CD4 | CD32 |
| CLEC12A | CD80 | CD4 | CD79a |
| CLEC12A | CD80 | CD4 | CD79b |
| CLEC12A | CD80 | b2c | CD8 |
| CLEC12A | CD80 | b2c | CD3ζ |
| CLEC12A | CD80 | b2c | CD3δ |
| CLEC12A | CD80 | b2c | CD3γ |
| CLEC12A | CD80 | b2c | CD3ε |
| CLEC12A | CD80 | b2c | FcγRI-γ |
| CLEC12A | CD80 | b2c | FcγRIII-γ |
| CLEC12A | CD80 | b2c | FcεRIβ |
| CLEC12A | CD80 | b2c | FcεRIγ |
| CLEC12A | CD80 | b2c | DAP10 |
| CLEC12A | CD80 | b2c | DAP12 |
| CLEC12A | CD80 | b2c | CD32 |
| CLEC12A | CD80 | b2c | CD79a |
| CLEC12A | CD80 | b2c | CD79b |
| CLEC12A | CD80 | CD137/41BB | CD8 |
| CLEC12A | CD80 | CD137/41BB | CD3ζ |
| CLEC12A | CD80 | CD137/41BB | CD3δ |
| CLEC12A | CD80 | CD137/41BB | CD3γ |
| CLEC12A | CD80 | CD137/41BB | CD3ε |
| CLEC12A | CD80 | CD137/41BB | FcγRI-γ |
| CLEC12A | CD80 | CD137/41BB | FcγRIII-γ |
| CLEC12A | CD80 | CD137/41BB | FcεRIβ |
| CLEC12A | CD80 | CD137/41BB | FcεRIγ |
| CLEC12A | CD80 | CD137/41BB | DAP10 |
| CLEC12A | CD80 | CD137/41BB | DAP12 |
| CLEC12A | CD80 | CD137/41BB | CD32 |
| CLEC12A | CD80 | CD137/41BB | CD79a |
| CLEC12A | CD80 | CD137/41BB | CD79b |
| CLEC12A | CD80 | ICOS | CD8 |
| CLEC12A | CD80 | ICOS | CD3ζ |
| CLEC12A | CD80 | ICOS | CD3δ |
| CLEC12A | CD80 | ICOS | CD3γ |
| CLEC12A | CD80 | ICOS | CD3ε |
| CLEC12A | CD80 | ICOS | FcγRI-γ |
| CLEC12A | CD80 | ICOS | FcγRIII-γ |
| CLEC12A | CD80 | ICOS | FcεRIβ |
| CLEC12A | CD80 | ICOS | FcεRIγ |
| CLEC12A | CD80 | ICOS | DAP10 |
| CLEC12A | CD80 | ICOS | DAP12 |
| CLEC12A | CD80 | ICOS | CD32 |
| CLEC12A | CD80 | ICOS | CD79a |
| CLEC12A | CD80 | ICOS | CD79b |
| CLEC12A | CD80 | CD27 | CD8 |
| CLEC12A | CD80 | CD27 | CD3ζ |
| CLEC12A | CD80 | CD27 | CD3δ |
| CLEC12A | CD80 | CD27 | CD3ε |
| CLEC12A | CD80 | CD27 | FcγRI-γ |
| CLEC12A | CD80 | CD27 | FcγRIII-γ |
| CLEC12A | CD80 | CD27 | FcεRIβ |
| CLEC12A | CD80 | CD27 | FcεRIγ |
| CLEC12A | CD80 | CD27 | DAP10 |
| CLEC12A | CD80 | CD27 | DAP12 |
| CLEC12A | CD80 | CD27 | CD32 |
| CLEC12A | CD80 | CD27 | CD79a |
| CLEC12A | CD80 | CD27 | CD79b |

TABLE 3-continued

Third Generation CARs

| ScFv | Co-stimulatory Signal | Co-stimulatory Signal | Signal Domain |
|---|---|---|---|
| CLEC12A | CD80 | CD28δ | CD8 |
| CLEC12A | CD80 | CD28δ | CD3ζ |
| CLEC12A | CD80 | CD28δ | CD3δ |
| CLEC12A | CD80 | CD28δ | CD3γ |
| CLEC12A | CD80 | CD28δ | CD3ε |
| CLEC12A | CD80 | CD28δ | FcγRI-γ |
| CLEC12A | CD80 | CD28δ | FcγRIII-γ |
| CLEC12A | CD80 | CD28δ | FcεRIβ |
| CLEC12A | CD80 | CD28δ | FcεRIγ |
| CLEC12A | CD80 | CD28δ | DAP10 |
| CLEC12A | CD80 | CD28δ | DAP12 |
| CLEC12A | CD80 | CD28δ | CD32 |
| CLEC12A | CD80 | CD28δ | CD79a |
| CLEC12A | CD80 | CD28δ | CD79b |
| CLEC12A | CD80 | CD80 | CD8 |
| CLEC12A | CD80 | CD80 | CD3ζ |
| CLEC12A | CD80 | CD80 | CD3δ |
| CLEC12A | CD80 | CD80 | CD3γ |
| CLEC12A | CD80 | CD80 | CD3ε |
| CLEC12A | CD80 | CD80 | FcγRI-γ |
| CLEC12A | CD80 | CD80 | FcγRIII-γ |
| CLEC12A | CD80 | CD80 | FcεRIβ |
| CLEC12A | CD80 | CD80 | FcεRIγ |
| CLEC12A | CD80 | CD80 | DAP10 |
| CLEC12A | CD80 | CD80 | DAP12 |
| CLEC12A | CD80 | CD80 | CD32 |
| CLEC12A | CD80 | CD80 | CD79a |
| CLEC12A | CD80 | CD80 | CD79b |
| CLEC12A | CD80 | CD86 | CD8 |
| CLEC12A | CD80 | CD86 | CD3ζ |
| CLEC12A | CD80 | CD86 | CD3δ |
| CLEC12A | CD80 | CD86 | CD3γ |
| CLEC12A | CD80 | CD86 | CD3ε |
| CLEC12A | CD80 | CD86 | FcγRI-γ |
| CLEC12A | CD80 | CD86 | FcγRIII-γ |
| CLEC12A | CD80 | CD86 | FcεRIβ |
| CLEC12A | CD80 | CD86 | FcεRIγ |
| CLEC12A | CD80 | CD86 | DAP10 |
| CLEC12A | CD80 | CD86 | DAP12 |
| CLEC12A | CD80 | CD86 | CD32 |
| CLEC12A | CD80 | CD86 | CD79a |
| CLEC12A | CD80 | CD86 | CD79b |
| CLEC12A | CD80 | OX40 | CD8 |
| CLEC12A | CD80 | OX40 | CD3ζ |
| CLEC12A | CD80 | OX40 | CD3δ |
| CLEC12A | CD80 | OX40 | CD3γ |
| CLEC12A | CD80 | OX40 | CD3ε |
| CLEC12A | CD80 | OX40 | FcγRI-γ |
| CLEC12A | CD80 | OX40 | FcγRIII-γ |
| CLEC12A | CD80 | OX40 | FcεRIβ |
| CLEC12A | CD80 | OX40 | FcεRIγ |
| CLEC12A | CD80 | OX40 | DAP10 |
| CLEC12A | CD80 | OX40 | DAP12 |
| CLEC12A | CD80 | OX40 | CD32 |
| CLEC12A | CD80 | OX40 | CD79a |
| CLEC12A | CD80 | OX40 | CD79b |
| CLEC12A | CD80 | DAP10 | CD8 |
| CLEC12A | CD80 | DAP10 | CD3ζ |
| CLEC12A | CD80 | DAP10 | CD3δ |
| CLEC12A | CD80 | DAP10 | CD3γ |
| CLEC12A | CD80 | DAP10 | CD3ε |
| CLEC12A | CD80 | DAP10 | FcγRI-γ |
| CLEC12A | CD80 | DAP10 | FcγRIII-γ |
| CLEC12A | CD80 | DAP10 | FcεRIβ |
| CLEC12A | CD80 | DAP10 | FcεRIγ |
| CLEC12A | CD80 | DAP10 | DAP10 |
| CLEC12A | CD80 | DAP10 | DAP12 |
| CLEC12A | CD80 | DAP10 | CD32 |
| CLEC12A | CD80 | DAP10 | CD79a |
| CLEC12A | CD80 | DAP10 | CD79b |
| CLEC12A | CD80 | DAP12 | CD8 |
| CLEC12A | CD80 | DAP12 | CD3ζ |
| CLEC12A | CD80 | DAP12 | CD3δ |
| CLEC12A | CD80 | DAP12 | CD3γ |
| CLEC12A | CD80 | DAP12 | CD3ε |
| CLEC12A | CD80 | DAP12 | FcγRI-γ |
| CLEC12A | CD80 | DAP12 | FcγRIII-γ |
| CLEC12A | CD80 | DAP12 | FcεRIβ |
| CLEC12A | CD80 | DAP12 | FcεRIγ |
| CLEC12A | CD80 | DAP12 | DAP10 |
| CLEC12A | CD80 | DAP12 | DAP12 |
| CLEC12A | CD80 | DAP12 | CD32 |
| CLEC12A | CD80 | DAP12 | CD79a |
| CLEC12A | CD80 | DAP12 | CD79b |
| CLEC12A | CD80 | MyD88 | CD8 |
| CLEC12A | CD80 | MyD88 | CD3ζ |
| CLEC12A | CD80 | MyD88 | CD3δ |
| CLEC12A | CD80 | MyD88 | CD3γ |
| CLEC12A | CD80 | MyD88 | CD3ε |
| CLEC12A | CD80 | MyD88 | FcγRI-γ |
| CLEC12A | CD80 | MyD88 | FcγRIII-γ |
| CLEC12A | CD80 | MyD88 | FcεRIβ |
| CLEC12A | CD80 | MyD88 | FcεRIγ |
| CLEC12A | CD80 | MyD88 | DAP10 |
| CLEC12A | CD80 | MyD88 | DAP12 |
| CLEC12A | CD80 | MyD88 | CD32 |
| CLEC12A | CD80 | MyD88 | CD79a |
| CLEC12A | CD80 | MyD88 | CD79b |
| CLEC12A | CD80 | CD7 | CD8 |
| CLEC12A | CD80 | CD7 | CD3ζ |
| CLEC12A | CD80 | CD7 | CD3δ |
| CLEC12A | CD80 | CD7 | CD3γ |
| CLEC12A | CD80 | CD7 | CD3ε |
| CLEC12A | CD80 | CD7 | FcγRI-γ |
| CLEC12A | CD80 | CD7 | FcγRIII-γ |
| CLEC12A | CD80 | CD7 | FcεRIβ |
| CLEC12A | CD80 | CD7 | FcεRIγ |
| CLEC12A | CD80 | CD7 | DAP10 |
| CLEC12A | CD80 | CD7 | DAP12 |
| CLEC12A | CD80 | CD7 | CD32 |
| CLEC12A | CD80 | CD7 | CD79a |
| CLEC12A | CD80 | CD7 | CD79b |
| CLEC12A | CD80 | BTNL3 | CD8 |
| CLEC12A | CD80 | BTNL3 | CD3ζ |
| CLEC12A | CD80 | BTNL3 | CD3δ |
| CLEC12A | CD80 | BTNL3 | CD3γ |
| CLEC12A | CD80 | BTNL3 | CD3ε |
| CLEC12A | CD80 | BTNL3 | FcγRI-γ |
| CLEC12A | CD80 | BTNL3 | FcγRIII-γ |
| CLEC12A | CD80 | BTNL3 | FcεRIβ |
| CLEC12A | CD80 | BTNL3 | FcεRIγ |
| CLEC12A | CD80 | BTNL3 | DAP10 |
| CLEC12A | CD80 | BTNL3 | DAP12 |
| CLEC12A | CD80 | BTNL3 | CD32 |
| CLEC12A | CD80 | BTNL3 | CD79a |
| CLEC12A | CD80 | BTNL3 | CD79b |
| CLEC12A | CD80 | NKG2D | CD8 |
| CLEC12A | CD80 | NKG2D | CD3ζ |
| CLEC12A | CD80 | NKG2D | CD3δ |
| CLEC12A | CD80 | NKG2D | CD3γ |
| CLEC12A | CD80 | NKG2D | CD3ε |
| CLEC12A | CD80 | NKG2D | FcγRI-γ |
| CLEC12A | CD80 | NKG2D | FcγRIII-γ |
| CLEC12A | CD80 | NKG2D | FcεRIβ |
| CLEC12A | CD80 | NKG2D | FcεRIγ |
| CLEC12A | CD80 | NKG2D | DAP10 |
| CLEC12A | CD80 | NKG2D | DAP12 |
| CLEC12A | CD80 | NKG2D | CD32 |
| CLEC12A | CD80 | NKG2D | CD79a |
| CLEC12A | CD80 | NKG2D | CD79b |
| CLEC12A | CD86 | CD28 | CD8 |
| CLEC12A | CD86 | CD28 | CD3ζ |
| CLEC12A | CD86 | CD28 | CD3δ |
| CLEC12A | CD86 | CD28 | CD3γ |
| CLEC12A | CD86 | CD28 | CD3ε |
| CLEC12A | CD86 | CD28 | FcγRI-γ |
| CLEC12A | CD86 | CD28 | FcγRIII-γ |
| CLEC12A | CD86 | CD28 | FcεRIβ |
| CLEC12A | CD86 | CD28 | FcεRIγ |
| CLEC12A | CD86 | CD28 | DAP10 |

TABLE 3-continued

Third Generation CARs

| ScFv | Co-stimulatory Signal | Co-stimulatory Signal | Signal Domain |
|---|---|---|---|
| CLEC12A | CD86 | CD28 | DAP12 |
| CLEC12A | CD86 | CD28 | CD32 |
| CLEC12A | CD86 | CD28 | CD79a |
| CLEC12A | CD86 | CD28 | CD79b |
| CLEC12A | CD86 | CD8 | CD8 |
| CLEC12A | CD86 | CD8 | CD3ζ |
| CLEC12A | CD86 | CD8 | CD3δ |
| CLEC12A | CD86 | CD8 | CD3γ |
| CLEC12A | CD86 | CD8 | CD3ε |
| CLEC12A | CD86 | CD8 | FcγRI-γ |
| CLEC12A | CD86 | CD8 | FcγRIII-γ |
| CLEC12A | CD86 | CD8 | FcεRIβ |
| CLEC12A | CD86 | CD8 | FcεRIγ |
| CLEC12A | CD86 | CD8 | DAP10 |
| CLEC12A | CD86 | CD8 | DAP12 |
| CLEC12A | CD86 | CD8 | CD32 |
| CLEC12A | CD86 | CD8 | CD79a |
| CLEC12A | CD86 | CD8 | CD79b |
| CLEC12A | CD86 | CD4 | CD8 |
| CLEC12A | CD86 | CD4 | CD3ζ |
| CLEC12A | CD86 | CD4 | CD3δ |
| CLEC12A | CD86 | CD4 | CD3γ |
| CLEC12A | CD86 | CD4 | CD3ε |
| CLEC12A | CD86 | CD4 | FcγRI-γ |
| CLEC12A | CD86 | CD4 | FcγRIII-γ |
| CLEC12A | CD86 | CD4 | FcεRIβ |
| CLEC12A | CD86 | CD4 | FcεRIγ |
| CLEC12A | CD86 | CD4 | DAP10 |
| CLEC12A | CD86 | CD4 | DAP12 |
| CLEC12A | CD86 | CD4 | CD32 |
| CLEC12A | CD86 | CD4 | CD79a |
| CLEC12A | CD86 | CD4 | CD79b |
| CLEC12A | CD86 | b2c | CD8 |
| CLEC12A | CD86 | b2c | CD3ζ |
| CLEC12A | CD86 | b2c | CD3δ |
| CLEC12A | CD86 | b2c | CD3δ |
| CLEC12A | CD86 | b2c | CD3ε |
| CLEC12A | CD86 | b2c | FcγRI-γ |
| CLEC12A | CD86 | b2c | FcγRIII-γ |
| CLEC12A | CD86 | b2c | FcεRIβ |
| CLEC12A | CD86 | b2c | FcεRIγ |
| CLEC12A | CD86 | b2c | DAP10 |
| CLEC12A | CD86 | b2c | DAP12 |
| CLEC12A | CD86 | b2c | CD32 |
| CLEC12A | CD86 | b2c | CD79a |
| CLEC12A | CD86 | b2c | CD79b |
| CLEC12A | CD86 | CD137/41BB | CD8 |
| CLEC12A | CD86 | CD137/41BB | CD3ζ |
| CLEC12A | CD86 | CD137/41BB | CD3δ |
| CLEC12A | CD86 | CD137/41BB | CD3γ |
| CLEC12A | CD86 | CD137/41BB | CD3ε |
| CLEC12A | CD86 | CD137/41BB | FcγRI-γ |
| CLEC12A | CD86 | CD137/41BB | FcγRIII-γ |
| CLEC12A | CD86 | CD137/41BB | FcεRIβ |
| CLEC12A | CD86 | CD137/41BB | FcεRIγ |
| CLEC12A | CD86 | CD137/41BB | DAP10 |
| CLEC12A | CD86 | CD137/41BB | DAP12 |
| CLEC12A | CD86 | CD137/41BB | CD32 |
| CLEC12A | CD86 | CD137/41BB | CD79a |
| CLEC12A | CD86 | CD137/41BB | CD79b |
| CLEC12A | CD86 | ICOS | CD8 |
| CLEC12A | CD86 | ICOS | CD3ζ |
| CLEC12A | CD86 | ICOS | CD3δ |
| CLEC12A | CD86 | ICOS | CD3γ |
| CLEC12A | CD86 | ICOS | CD3ε |
| CLEC12A | CD86 | ICOS | FcγRI-γ |
| CLEC12A | CD86 | ICOS | FcγRIII-γ |
| CLEC12A | CD86 | ICOS | FcεRIβ |
| CLEC12A | CD86 | ICOS | FcεRIγ |
| CLEC12A | CD86 | ICOS | DAP10 |
| CLEC12A | CD86 | ICOS | DAP12 |
| CLEC12A | CD86 | ICOS | CD32 |
| CLEC12A | CD86 | ICOS | CD79a |
| CLEC12A | CD86 | ICOS | CD79b |
| CLEC12A | CD86 | CD27 | CD8 |
| CLEC12A | CD86 | CD27 | CD3ζ |
| CLEC12A | CD86 | CD27 | CD3δ |
| CLEC12A | CD86 | CD27 | CD3γ |
| CLEC12A | CD86 | CD27 | CD3ε |
| CLEC12A | CD86 | CD27 | FcγRI-γ |
| CLEC12A | CD86 | CD27 | FcγRIII-γ |
| CLEC12A | CD86 | CD27 | FcεRIβ |
| CLEC12A | CD86 | CD27 | FcεRIγ |
| CLEC12A | CD86 | CD27 | DAP10 |
| CLEC12A | CD86 | CD27 | DAP12 |
| CLEC12A | CD86 | CD27 | CD32 |
| CLEC12A | CD86 | CD27 | CD79a |
| CLEC12A | CD86 | CD27 | CD79b |
| CLEC12A | CD86 | CD28δ | CD8 |
| CLEC12A | CD86 | CD28δ | CD3ζ |
| CLEC12A | CD86 | CD28δ | CD3δ |
| CLEC12A | CD86 | CD28δ | CD3γ |
| CLEC12A | CD86 | CD28δ | CD3ε |
| CLEC12A | CD86 | CD28δ | FcγRI-γ |
| CLEC12A | CD86 | CD28δ | FcγRIII-γ |
| CLEC12A | CD86 | CD28δ | FcεRIβ |
| CLEC12A | CD86 | CD28δ | FcεRIγ |
| CLEC12A | CD86 | CD28δ | DAP10 |
| CLEC12A | CD86 | CD28δ | DAP12 |
| CLEC12A | CD86 | CD28δ | CD32 |
| CLEC12A | CD86 | CD28δ | CD79a |
| CLEC12A | CD86 | CD28δ | CD79b |
| CLEC12A | CD86 | CD80 | CD8 |
| CLEC12A | CD86 | CD80 | CD3ζ |
| CLEC12A | CD86 | CD80 | CD3δ |
| CLEC12A | CD86 | CD80 | CD3γ |
| CLEC12A | CD86 | CD80 | CD3ε |
| CLEC12A | CD86 | CD80 | FcγRI-γ |
| CLEC12A | CD86 | CD80 | FcγRIII-γ |
| CLEC12A | CD86 | CD80 | FcεRIβ |
| CLEC12A | CD86 | CD80 | FcεRIγ |
| CLEC12A | CD86 | CD80 | DAP10 |
| CLEC12A | CD86 | CD80 | DAP12 |
| CLEC12A | CD86 | CD80 | CD32 |
| CLEC12A | CD86 | CD80 | CD79a |
| CLEC12A | CD86 | CD80 | CD79b |
| CLEC12A | CD86 | CD86 | CD8 |
| CLEC12A | CD86 | CD86 | CD3ζ |
| CLEC12A | CD86 | CD86 | CD3δ |
| CLEC12A | CD86 | CD86 | CD3γ |
| CLEC12A | CD86 | CD86 | CD3ε |
| CLEC12A | CD86 | CD86 | FcγRI-γ |
| CLEC12A | CD86 | CD86 | FcγRIII-γ |
| CLEC12A | CD86 | CD86 | FcεRIβ |
| CLEC12A | CD86 | CD86 | FcεRIγ |
| CLEC12A | CD86 | CD86 | DAP10 |
| CLEC12A | CD86 | CD86 | DAP12 |
| CLEC12A | CD86 | CD86 | CD32 |
| CLEC12A | CD86 | CD86 | CD79a |
| CLEC12A | CD86 | CD86 | CD79b |
| CLEC12A | CD86 | OX40 | CD8 |
| CLEC12A | CD86 | OX40 | CD3ζ |
| CLEC12A | CD86 | OX40 | CD3δ |
| CLEC12A | CD86 | OX40 | CD3γ |
| CLEC12A | CD86 | OX40 | CD3ε |
| CLEC12A | CD86 | OX40 | FcγRI-γ |
| CLEC12A | CD86 | OX40 | FcγRIII-γ |
| CLEC12A | CD86 | OX40 | FcεRIβ |
| CLEC12A | CD86 | OX40 | FcεRIγ |
| CLEC12A | CD86 | OX40 | DAP10 |
| CLEC12A | CD86 | OX40 | DAP12 |
| CLEC12A | CD86 | OX40 | CD32 |
| CLEC12A | CD86 | OX40 | CD79a |
| CLEC12A | CD86 | OX40 | CD79b |
| CLEC12A | CD86 | DAP10 | CD8 |
| CLEC12A | CD86 | DAP10 | CD3ζ |
| CLEC12A | CD86 | DAP10 | CD3δ |
| CLEC12A | CD86 | DAP10 | CD3γ |
| CLEC12A | CD86 | DAP10 | CD3ε |
| CLEC12A | CD86 | DAP10 | FcγRI-γ |

TABLE 3-continued

| Third Generation CARs | | | |
|---|---|---|---|
| ScFv | Co-stimulatory Signal | Co-stimulatory Signal | Signal Domain |
| CLEC12A | CD86 | DAP10 | FcγRIII-γ |
| CLEC12A | CD86 | DAP10 | FcεRIβ |
| CLEC12A | CD86 | DAP10 | FcεRIγ |
| CLEC12A | CD86 | DAP10 | DAP10 |
| CLEC12A | CD86 | DAP10 | DAP12 |
| CLEC12A | CD86 | DAP10 | CD32 |
| CLEC12A | CD86 | DAP10 | CD79a |
| CLEC12A | CD86 | DAP10 | CD79b |
| CLEC12A | CD86 | DAP12 | CD8 |
| CLEC12A | CD86 | DAP12 | CD3ζ |
| CLEC12A | CD86 | DAP12 | CD3δ |
| CLEC12A | CD86 | DAP12 | CD3γ |
| CLEC12A | CD86 | DAP12 | CD3ε |
| CLEC12A | CD86 | DAP12 | FcγRI-γ |
| CLEC12A | CD86 | DAP12 | FcγRIII-γ |
| CLEC12A | CD86 | DAP12 | FcεRIβ |
| CLEC12A | CD86 | DAP12 | FcεRIγ |
| CLEC12A | CD86 | DAP12 | DAP10 |
| CLEC12A | CD86 | DAP12 | DAP12 |
| CLEC12A | CD86 | DAP12 | CD32 |
| CLEC12A | CD86 | DAP12 | CD79a |
| CLEC12A | CD86 | DAP12 | CD79b |
| CLEC12A | CD86 | MyD88 | CD8 |
| CLEC12A | CD86 | MyD88 | CD3ζ |
| CLEC12A | CD86 | MyD88 | CD3δ |
| CLEC12A | CD86 | MyD88 | CD3γ |
| CLEC12A | CD86 | MyD88 | CD3ε |
| CLEC12A | CD86 | MyD88 | FcγRI-γ |
| CLEC12A | CD86 | MyD88 | FcγRIII-γ |
| CLEC12A | CD86 | MyD88 | FcεRIβ |
| CLEC12A | CD86 | MyD88 | FcεRIγ |
| CLEC12A | CD86 | MyD88 | DAP10 |
| CLEC12A | CD86 | MyD88 | DAP12 |
| CLEC12A | CD86 | MyD88 | CD32 |
| CLEC12A | CD86 | MyD88 | CD79a |
| CLEC12A | CD86 | MyD88 | CD79b |
| CLEC12A | CD86 | CD7 | CD8 |
| CLEC12A | CD86 | CD7 | CD3ζ |
| CLEC12A | CD86 | CD7 | CD3δ |
| CLEC12A | CD86 | CD7 | CD3γ |
| CLEC12A | CD86 | CD7 | CD3ε |
| CLEC12A | CD86 | CD7 | FcγRI-γ |
| CLEC12A | CD86 | CD7 | FcγRIII-γ |
| CLEC12A | CD86 | CD7 | FcεRIβ |
| CLEC12A | CD86 | CD7 | FcεRIγ |
| CLEC12A | CD86 | CD7 | DAP10 |
| CLEC12A | CD86 | CD7 | DAP12 |
| CLEC12A | CD86 | CD7 | CD32 |
| CLEC12A | CD86 | CD7 | CD79a |
| CLEC12A | CD86 | CD7 | CD79b |
| CLEC12A | CD86 | BTNL3 | CD8 |
| CLEC12A | CD86 | BTNL3 | CD3ζ |
| CLEC12A | CD86 | BTNL3 | CD3δ |
| CLEC12A | CD86 | BTNL3 | CD3γ |
| CLEC12A | CD86 | BTNL3 | CD3ε |
| CLEC12A | CD86 | BTNL3 | FcγRI-γ |
| CLEC12A | CD86 | BTNL3 | FcγRIII-γ |
| CLEC12A | CD86 | BTNL3 | FcεRIβ |
| CLEC12A | CD86 | BTNL3 | FcεRIγ |
| CLEC12A | CD86 | BTNL3 | DAP10 |
| CLEC12A | CD86 | BTNL3 | DAP12 |
| CLEC12A | CD86 | BTNL3 | CD32 |
| CLEC12A | CD86 | BTNL3 | CD79a |
| CLEC12A | CD86 | BTNL3 | CD79b |
| CLEC12A | CD86 | NKG2D | CD8 |
| CLEC12A | CD86 | NKG2D | CD3ζ |
| CLEC12A | CD86 | NKG2D | CD3δ |
| CLEC12A | CD86 | NKG2D | CD3γ |
| CLEC12A | CD86 | NKG2D | CD3ε |
| CLEC12A | CD86 | NKG2D | FcγRI-γ |
| CLEC12A | CD86 | NKG2D | FcγRIII-γ |
| CLEC12A | CD86 | NKG2D | FcεRIβ |
| CLEC12A | CD86 | NKG2D | FcεRIγ |
| CLEC12A | CD86 | NKG2D | DAP10 |
| CLEC12A | CD86 | NKG2D | DAP12 |
| CLEC12A | CD86 | NKG2D | CD32 |
| CLEC12A | CD86 | NKG2D | CD79a |
| CLEC12A | CD86 | NKG2D | CD79b |
| CLEC12A | OX40 | CD28 | CD8 |
| CLEC12A | OX40 | CD28 | CD3ζ |
| CLEC12A | OX40 | CD28 | CD3δ |
| CLEC12A | OX40 | CD28 | CD3γ |
| CLEC12A | OX40 | CD28 | CD3ε |
| CLEC12A | OX40 | CD28 | FcγRI-γ |
| CLEC12A | OX40 | CD28 | FcγRIII-γ |
| CLEC12A | OX40 | CD28 | FcεRIβ |
| CLEC12A | OX40 | CD28 | FcεRIγ |
| CLEC12A | OX40 | CD28 | DAP10 |
| CLEC12A | OX40 | CD28 | DAP12 |
| CLEC12A | OX40 | CD28 | CD32 |
| CLEC12A | OX40 | CD28 | CD79a |
| CLEC12A | OX40 | CD28 | CD79b |
| CLEC12A | OX40 | CD8 | CD8 |
| CLEC12A | OX40 | CD8 | CD3ζ |
| CLEC12A | OX40 | CD8 | CD3δ |
| CLEC12A | OX40 | CD8 | CD3γ |
| CLEC12A | OX40 | CD8 | CD3ε |
| CLEC12A | OX40 | CD8 | FcγRI-γ |
| CLEC12A | OX40 | CD8 | FcγRIII-γ |
| CLEC12A | OX40 | CD8 | FcεRIβ |
| CLEC12A | OX40 | CD8 | FcεRIγ |
| CLEC12A | OX40 | CD8 | DAP10 |
| CLEC12A | OX40 | CD8 | DAP12 |
| CLEC12A | OX40 | CD8 | CD32 |
| CLEC12A | OX40 | CD8 | CD79a |
| CLEC12A | OX40 | CD8 | CD79b |
| CLEC12A | OX40 | CD4 | CD8 |
| CLEC12A | OX40 | CD4 | CD3ζ |
| CLEC12A | OX40 | CD4 | CD3δ |
| CLEC12A | OX40 | CD4 | CD3γ |
| CLEC12A | OX40 | CD4 | CD3ε |
| CLEC12A | OX40 | CD4 | FcγRI-γ |
| CLEC12A | OX40 | CD4 | FcγRIII-γ |
| CLEC12A | OX40 | CD4 | FcεRIβ |
| CLEC12A | OX40 | CD4 | FcεRIγ |
| CLEC12A | OX40 | CD4 | DAP10 |
| CLEC12A | OX40 | CD4 | DAP12 |
| CLEC12A | OX40 | CD4 | CD32 |
| CLEC12A | OX40 | CD4 | CD79a |
| CLEC12A | OX40 | CD4 | CD79b |
| CLEC12A | OX40 | b2c | CD8 |
| CLEC12A | OX40 | b2c | CD3ζ |
| CLEC12A | OX40 | b2c | CD3δ |
| CLEC12A | OX40 | b2c | CD3γ |
| CLEC12A | OX40 | b2c | CD3ε |
| CLEC12A | OX40 | b2c | FcγRI-γ |
| CLEC12A | OX40 | b2c | FcγRIII-γ |
| CLEC12A | OX40 | b2c | FcεRIβ |
| CLEC12A | OX40 | b2c | FcεRIγ |
| CLEC12A | OX40 | b2c | DAP10 |
| CLEC12A | OX40 | b2c | DAP12 |
| CLEC12A | OX40 | b2c | CD32 |
| CLEC12A | OX40 | b2c | CD79a |
| CLEC12A | OX40 | b2c | CD79b |
| CLEC12A | OX40 | CD137/41BB | CD8 |
| CLEC12A | OX40 | CD137/41BB | CD3ζ |
| CLEC12A | OX40 | CD137/41BB | CD3δ |
| CLEC12A | OX40 | CD137/41BB | CD3γ |
| CLEC12A | OX40 | CD137/41BB | CD3ε |
| CLEC12A | OX40 | CD137/41BB | FcγRI-γ |
| CLEC12A | OX40 | CD137/41BB | FcγRIII-γ |
| CLEC12A | OX40 | CD137/41BB | FcεRIβ |
| CLEC12A | OX40 | CD137/41BB | FcεRIγ |
| CLEC12A | OX40 | CD137/41BB | DAP10 |
| CLEC12A | OX40 | CD137/41BB | DAP12 |
| CLEC12A | OX40 | CD137/41BB | CD32 |
| CLEC12A | OX40 | CD137/41BB | CD79a |
| CLEC12A | OX40 | CD137/41BB | CD79b |
| CLEC12A | OX40 | ICOS | CD8 |
| CLEC12A | OX40 | ICOS | CD3ζ |

TABLE 3-continued

Third Generation CARs

| ScFv | Co-stimulatory Signal | Co-stimulatory Signal | Signal Domain |
|---|---|---|---|
| CLEC12A | OX40 | ICOS | CD3δ |
| CLEC12A | OX40 | ICOS | CD3γ |
| CLEC12A | OX40 | ICOS | CD3ε |
| CLEC12A | OX40 | ICOS | FcγRI-γ |
| CLEC12A | OX40 | ICOS | FcγRIII-γ |
| CLEC12A | OX40 | ICOS | FcεRIβ |
| CLEC12A | OX40 | ICOS | FcεRIγ |
| CLEC12A | OX40 | ICOS | DAP10 |
| CLEC12A | OX40 | ICOS | DAP12 |
| CLEC12A | OX40 | ICOS | CD32 |
| CLEC12A | OX40 | ICOS | CD79a |
| CLEC12A | OX40 | ICOS | CD79b |
| CLEC12A | OX40 | CD27 | CD8 |
| CLEC12A | OX40 | CD27 | CD3ζ |
| CLEC12A | OX40 | CD27 | CD3δ |
| CLEC12A | OX40 | CD27 | CD3γ |
| CLEC12A | OX40 | CD27 | CD3ε |
| CLEC12A | OX40 | CD27 | FcγRI-γ |
| CLEC12A | OX40 | CD27 | FcγRIII-γ |
| CLEC12A | OX40 | CD27 | FcεRIβ |
| CLEC12A | OX40 | CD27 | FcεRIγ |
| CLEC12A | OX40 | CD27 | DAP10 |
| CLEC12A | OX40 | CD27 | DAP12 |
| CLEC12A | OX40 | CD27 | CD32 |
| CLEC12A | OX40 | CD27 | CD79a |
| CLEC12A | OX40 | CD27 | CD79b |
| CLEC12A | OX40 | CD28δ | CD8 |
| CLEC12A | OX40 | CD28δ | CD3ζ |
| CLEC12A | OX40 | CD28δ | CD3δ |
| CLEC12A | OX40 | CD28δ | CD3γ |
| CLEC12A | OX40 | CD28δ | CD3ε |
| CLEC12A | OX40 | CD28δ | FcγRI-γ |
| CLEC12A | OX40 | CD28δ | FcγRIII-γ |
| CLEC12A | OX40 | CD28δ | FcεRIβ |
| CLEC12A | OX40 | CD28δ | FcεRIγ |
| CLEC12A | OX40 | CD28δ | DAP10 |
| CLEC12A | OX40 | CD28δ | DAP12 |
| CLEC12A | OX40 | CD28δ | CD32 |
| CLEC12A | OX40 | CD28δ | CD79a |
| CLEC12A | OX40 | CD28δ | CD79b |
| CLEC12A | OX40 | CD80 | CD8 |
| CLEC12A | OX40 | CD80 | CD3ζ |
| CLEC12A | OX40 | CD80 | CD3δ |
| CLEC12A | OX40 | CD80 | CD3γ |
| CLEC12A | OX40 | CD80 | CD3ε |
| CLEC12A | OX40 | CD80 | FcγRI-γ |
| CLEC12A | OX40 | CD80 | FcγRIII-γ |
| CLEC12A | OX40 | CD80 | FcεRIβ |
| CLEC12A | OX40 | CD80 | FcεRIγ |
| CLEC12A | OX40 | CD80 | DAP10 |
| CLEC12A | OX40 | CD80 | DAP12 |
| CLEC12A | OX40 | CD80 | CD32 |
| CLEC12A | OX40 | CD80 | CD79a |
| CLEC12A | OX40 | CD80 | CD79b |
| CLEC12A | OX40 | CD86 | CD8 |
| CLEC12A | OX40 | CD86 | CD3ζ |
| CLEC12A | OX40 | CD86 | CD3δ |
| CLEC12A | OX40 | CD86 | CD3γ |
| CLEC12A | OX40 | CD86 | CD3ε |
| CLEC12A | OX40 | CD86 | FcγRI-γ |
| CLEC12A | OX40 | CD86 | FcγRIII-γ |
| CLEC12A | OX40 | CD86 | FcεRIβ |
| CLEC12A | OX40 | CD86 | FcεRIγ |
| CLEC12A | OX40 | CD86 | DAP10 |
| CLEC12A | OX40 | CD86 | DAP12 |
| CLEC12A | OX40 | CD86 | CD32 |
| CLEC12A | OX40 | CD86 | CD79a |
| CLEC12A | OX40 | CD86 | CD79b |
| CLEC12A | OX40 | OX40 | CD8 |
| CLEC12A | OX40 | OX40 | CD3ζ |
| CLEC12A | OX40 | OX40 | CD3δ |
| CLEC12A | OX40 | OX40 | CD3γ |
| CLEC12A | OX40 | OX40 | CD3ε |
| CLEC12A | OX40 | OX40 | FcγRI-γ |
| CLEC12A | OX40 | OX40 | FcγRIII-γ |
| CLEC12A | OX40 | OX40 | FcεRIβ |
| CLEC12A | OX40 | OX40 | FcεRIγ |
| CLEC12A | OX40 | OX40 | DAP10 |
| CLEC12A | OX40 | OX40 | DAP12 |
| CLEC12A | OX40 | OX40 | CD32 |
| CLEC12A | OX40 | OX40 | CD79a |
| CLEC12A | OX40 | OX40 | CD79b |
| CLEC12A | OX40 | DAP10 | CD8 |
| CLEC12A | OX40 | DAP10 | CD3ζ |
| CLEC12A | OX40 | DAP10 | CD3δ |
| CLEC12A | OX40 | DAP10 | CD3γ |
| CLEC12A | OX40 | DAP10 | CD3ε |
| CLEC12A | OX40 | DAP10 | FcγRI-γ |
| CLEC12A | OX40 | DAP10 | FcγRIII-γ |
| CLEC12A | OX40 | DAP10 | FcεRIβ |
| CLEC12A | OX40 | DAP10 | FcεRIγ |
| CLEC12A | OX40 | DAP10 | DAP10 |
| CLEC12A | OX40 | DAP10 | DAP12 |
| CLEC12A | OX40 | DAP10 | CD32 |
| CLEC12A | OX40 | DAP10 | CD79a |
| CLEC12A | OX40 | DAP10 | CD79b |
| CLEC12A | OX40 | DAP12 | CD8 |
| CLEC12A | OX40 | DAP12 | CD3ζ |
| CLEC12A | OX40 | DAP12 | CD3δ |
| CLEC12A | OX40 | DAP12 | CD3γ |
| CLEC12A | OX40 | DAP12 | CD3ε |
| CLEC12A | OX40 | DAP12 | FcγRI-γ |
| CLEC12A | OX40 | DAP12 | FcγRIII-γ |
| CLEC12A | OX40 | DAP12 | FcεRIβ |
| CLEC12A | OX40 | DAP12 | FcεRIγ |
| CLEC12A | OX40 | DAP12 | DAP10 |
| CLEC12A | OX40 | DAP12 | DAP12 |
| CLEC12A | OX40 | DAP12 | CD32 |
| CLEC12A | OX40 | DAP12 | CD79a |
| CLEC12A | OX40 | DAP12 | CD79b |
| CLEC12A | OX40 | MyD88 | CD8 |
| CLEC12A | OX40 | MyD88 | CD3ζ |
| CLEC12A | OX40 | MyD88 | CD3δ |
| CLEC12A | OX40 | MyD88 | CD3γ |
| CLEC12A | OX40 | MyD88 | CD3ε |
| CLEC12A | OX40 | MyD88 | FcγRI-γ |
| CLEC12A | OX40 | MyD88 | FcγRIII-γ |
| CLEC12A | OX40 | MyD88 | FcεRIβ |
| CLEC12A | OX40 | MyD88 | FcεRIγ |
| CLEC12A | OX40 | MyD88 | DAP10 |
| CLEC12A | OX40 | MyD88 | DAP12 |
| CLEC12A | OX40 | MyD88 | CD32 |
| CLEC12A | OX40 | MyD88 | CD79a |
| CLEC12A | OX40 | MyD88 | CD79b |
| CLEC12A | OX40 | CD7 | CD8 |
| CLEC12A | OX40 | CD7 | CD3ζ |
| CLEC12A | OX40 | CD7 | CD3δ |
| CLEC12A | OX40 | CD7 | CD3γ |
| CLEC12A | OX40 | CD7 | CD3E |
| CLEC12A | OX40 | CD7 | FcγRI-γ |
| CLEC12A | OX40 | CD7 | FcγRIII-γ |
| CLEC12A | OX40 | CD7 | FcεRIβ |
| CLEC12A | OX40 | CD7 | FcεRIγ |
| CLEC12A | OX40 | CD7 | DAP10 |
| CLEC12A | OX40 | CD7 | DAP12 |
| CLEC12A | OX40 | CD7 | CD32 |
| CLEC12A | OX40 | CD7 | CD79a |
| CLEC12A | OX40 | CD7 | CD79b |
| CLEC12A | OX40 | BTNL3 | CD8 |
| CLEC12A | OX40 | BTNL3 | CD3ζ |
| CLEC12A | OX40 | BTNL3 | CD3δ |
| CLEC12A | OX40 | BTNL3 | CD3γ |
| CLEC12A | OX40 | BTNL3 | CD3ε |
| CLEC12A | OX40 | BTNL3 | FcγRI-γ |
| CLEC12A | OX40 | BTNL3 | FcγRIII-γ |
| CLEC12A | OX40 | BTNL3 | FcεRIβ |
| CLEC12A | OX40 | BTNL3 | FcεRIγ |
| CLEC12A | OX40 | BTNL3 | DAP10 |
| CLEC12A | OX40 | BTNL3 | DAP12 |
| CLEC12A | OX40 | BTNL3 | CD32 |

TABLE 3-continued

Third Generation CARs

| ScFv | Co-stimulatory Signal | Co-stimulatory Signal | Signal Domain |
|---|---|---|---|
| CLEC12A | OX40 | BTNL3 | CD79a |
| CLEC12A | OX40 | BTNL3 | CD79b |
| CLEC12A | OX40 | NKG2D | CD8 |
| CLEC12A | OX40 | NKG2D | CD3ζ |
| CLEC12A | OX40 | NKG2D | CD3δ |
| CLEC12A | OX40 | NKG2D | CD3γ |
| CLEC12A | OX40 | NKG2D | CD3ε |
| CLEC12A | OX40 | NKG2D | FcγRI-γ |
| CLEC12A | OX40 | NKG2D | FcγRIII-γ |
| CLEC12A | OX40 | NKG2D | FcεRIβ |
| CLEC12A | OX40 | NKG2D | FcεRIγ |
| CLEC12A | OX40 | NKG2D | DAP10 |
| CLEC12A | OX40 | NKG2D | DAP12 |
| CLEC12A | OX40 | NKG2D | CD32 |
| CLEC12A | OX40 | NKG2D | CD79a |
| CLEC12A | OX40 | NKG2D | CD79b |
| CLEC12A | DAP10 | CD28 | CD8 |
| CLEC12A | DAP10 | CD28 | CD3ζ |
| CLEC12A | DAP10 | CD28 | CD3δ |
| CLEC12A | DAP10 | CD28 | CD3γ |
| CLEC12A | DAP10 | CD28 | CD3ε |
| CLEC12A | DAP10 | CD28 | FcγRI-γ |
| CLEC12A | DAP10 | CD28 | FcγRIII-γ |
| CLEC12A | DAP10 | CD28 | FcεRIβ |
| CLEC12A | DAP10 | CD28 | FcεRIγ |
| CLEC12A | DAP10 | CD28 | DAP10 |
| CLEC12A | DAP10 | CD28 | DAP12 |
| CLEC12A | DAP10 | CD28 | CD32 |
| CLEC12A | DAP10 | CD28 | CD79a |
| CLEC12A | DAP10 | CD28 | CD79b |
| CLEC12A | DAP10 | CD8 | CD8 |
| CLEC12A | DAP10 | CD8 | CD3ζ |
| CLEC12A | DAP10 | CD8 | CD3δ |
| CLEC12A | DAP10 | CD8 | CD3γ |
| CLEC12A | DAP10 | CD8 | CD3ε |
| CLEC12A | DAP10 | CD8 | FcγRI-γ |
| CLEC12A | DAP10 | CD8 | FcγRIII-γ |
| CLEC12A | DAP10 | CD8 | FcεRIβ |
| CLEC12A | DAP10 | CD8 | FcεRIγ |
| CLEC12A | DAP10 | CD8 | DAP10 |
| CLEC12A | DAP10 | CD8 | DAP12 |
| CLEC12A | DAP10 | CD8 | CD32 |
| CLEC12A | DAP10 | CD8 | CD79a |
| CLEC12A | DAP10 | CD8 | CD79b |
| CLEC12A | DAP10 | CD4 | CD8 |
| CLEC12A | DAP10 | CD4 | CD3ζ |
| CLEC12A | DAP10 | CD4 | CD3δ |
| CLEC12A | DAP10 | CD4 | CD3γ |
| CLEC12A | DAP10 | CD4 | CD3ε |
| CLEC12A | DAP10 | CD4 | FcγRI-γ |
| CLEC12A | DAP10 | CD4 | FcγRIII-γ |
| CLEC12A | DAP10 | CD4 | FcεRIβ |
| CLEC12A | DAP10 | CD4 | FcεRIγ |
| CLEC12A | DAP10 | CD4 | DAP10 |
| CLEC12A | DAP10 | CD4 | DAP12 |
| CLEC12A | DAP10 | CD4 | CD32 |
| CLEC12A | DAP10 | CD4 | CD79a |
| CLEC12A | DAP10 | CD4 | CD79b |
| CLEC12A | DAP10 | b2c | CD8 |
| CLEC12A | DAP10 | b2c | CD3ζ |
| CLEC12A | DAP10 | b2c | CD3δ |
| CLEC12A | DAP10 | b2c | CD3γ |
| CLEC12A | DAP10 | b2c | CD3ε |
| CLEC12A | DAP10 | b2c | FcγRI-γ |
| CLEC12A | DAP10 | b2c | FcγRIII-γ |
| CLEC12A | DAP10 | b2c | FcεRIβ |
| CLEC12A | DAP10 | b2c | FcεRIγ |
| CLEC12A | DAP10 | b2c | DAP10 |
| CLEC12A | DAP10 | b2c | DAP12 |
| CLEC12A | DAP10 | b2c | CD32 |
| CLEC12A | DAP10 | b2c | CD79a |
| CLEC12A | DAP10 | b2c | CD79b |
| CLEC12A | DAP10 | CD137/41BB | CD8 |
| CLEC12A | DAP10 | CD137/41BB | CD3ζ |
| CLEC12A | DAP10 | CD137/41BB | CD3δ |
| CLEC12A | DAP10 | CD137/41BB | CD3γ |
| CLEC12A | DAP10 | CD137/41BB | CD3ε |
| CLEC12A | DAP10 | CD137/41BB | FcγRI-γ |
| CLEC12A | DAP10 | CD137/41BB | FcγRIII-γ |
| CLEC12A | DAP10 | CD137/41BB | FcεRIβ |
| CLEC12A | DAP10 | CD137/41BB | FcεRIγ |
| CLEC12A | DAP10 | CD137/41BB | DAP10 |
| CLEC12A | DAP10 | CD137/41BB | DAP12 |
| CLEC12A | DAP10 | CD137/41BB | CD32 |
| CLEC12A | DAP10 | CD137/41BB | CD79a |
| CLEC12A | DAP10 | CD137/41BB | CD79b |
| CLEC12A | DAP10 | ICOS | CD8 |
| CLEC12A | DAP10 | ICOS | CD3ζ |
| CLEC12A | DAP10 | ICOS | CD3δ |
| CLEC12A | DAP10 | ICOS | CD3γ |
| CLEC12A | DAP10 | ICOS | CD3ε |
| CLEC12A | DAP10 | ICOS | FcγRI-γ |
| CLEC12A | DAP10 | ICOS | FcγRIII-γ |
| CLEC12A | DAP10 | ICOS | FcεRIβ |
| CLEC12A | DAP10 | ICOS | FcεRIγ |
| CLEC12A | DAP10 | ICOS | DAP10 |
| CLEC12A | DAP10 | ICOS | DAP12 |
| CLEC12A | DAP10 | ICOS | CD32 |
| CLEC12A | DAP10 | ICOS | CD79a |
| CLEC12A | DAP10 | ICOS | CD79b |
| CLEC12A | DAP10 | CD27 | CD8 |
| CLEC12A | DAP10 | CD27 | CD3ζ |
| CLEC12A | DAP10 | CD27 | CD3δ |
| CLEC12A | DAP10 | CD27 | CD3γ |
| CLEC12A | DAP10 | CD27 | CD3ε |
| CLEC12A | DAP10 | CD27 | FcγRI-γ |
| CLEC12A | DAP10 | CD27 | FcγRIII-γ |
| CLEC12A | DAP10 | CD27 | FcεRIβ |
| CLEC12A | DAP10 | CD27 | FcεRIγ |
| CLEC12A | DAP10 | CD27 | DAP10 |
| CLEC12A | DAP10 | CD27 | DAP12 |
| CLEC12A | DAP10 | CD27 | CD32 |
| CLEC12A | DAP10 | CD27 | CD79a |
| CLEC12A | DAP10 | CD27 | CD79b |
| CLEC12A | DAP10 | CD28δ | CD8 |
| CLEC12A | DAP10 | CD28δ | CD3ζ |
| CLEC12A | DAP10 | CD28δ | CD3δ |
| CLEC12A | DAP10 | CD28δ | CD3γ |
| CLEC12A | DAP10 | CD28δ | CD3ε |
| CLEC12A | DAP10 | CD28δ | FcγRI-γ |
| CLEC12A | DAP10 | CD28δ | FcγRIII-γ |
| CLEC12A | DAP10 | CD28δ | FcεRIβ |
| CLEC12A | DAP10 | CD28δ | FcεRIγ |
| CLEC12A | DAP10 | CD28δ | DAP10 |
| CLEC12A | DAP10 | CD28δ | DAP12 |
| CLEC12A | DAP10 | CD28δ | CD32 |
| CLEC12A | DAP10 | CD28δ | CD79a |
| CLEC12A | DAP10 | CD28δ | CD79b |
| CLEC12A | DAP10 | CD80 | CD8 |
| CLEC12A | DAP10 | CD80 | CD3ζ |
| CLEC12A | DAP10 | CD80 | CD3δ |
| CLEC12A | DAP10 | CD80 | CD3γ |
| CLEC12A | DAP10 | CD80 | CD3ε |
| CLEC12A | DAP10 | CD80 | FcγRI-γ |
| CLEC12A | DAP10 | CD80 | FcγRIII-γ |
| CLEC12A | DAP10 | CD80 | FcεRIβ |
| CLEC12A | DAP10 | CD80 | FcεRIγ |
| CLEC12A | DAP10 | CD80 | DAP10 |
| CLEC12A | DAP10 | CD80 | DAP12 |
| CLEC12A | DAP10 | CD80 | CD32 |
| CLEC12A | DAP10 | CD80 | CD79a |
| CLEC12A | DAP10 | CD80 | CD79b |
| CLEC12A | DAP10 | CD86 | CD8 |
| CLEC12A | DAP10 | CD86 | CD3ζ |
| CLEC12A | DAP10 | CD86 | CD3δ |
| CLEC12A | DAP10 | CD86 | CD3γ |
| CLEC12A | DAP10 | CD86 | CD3ε |
| CLEC12A | DAP10 | CD86 | FcγRI-γ |
| CLEC12A | DAP10 | CD86 | FcγRIII-γ |
| CLEC12A | DAP10 | CD86 | FcεRIβ |

TABLE 3-continued

Third Generation CARs

| ScFv | Co-stimulatory Signal | Co-stimulatory Signal | Signal Domain |
|---|---|---|---|
| CLEC12A | DAP10 | CD86 | FcεRIγ |
| CLEC12A | DAP10 | CD86 | DAP10 |
| CLEC12A | DAP10 | CD86 | DAP12 |
| CLEC12A | DAP10 | CD86 | CD32 |
| CLEC12A | DAP10 | CD86 | CD79a |
| CLEC12A | DAP10 | CD86 | CD79b |
| CLEC12A | DAP10 | OX40 | CD8 |
| CLEC12A | DAP10 | OX40 | CD3ζ |
| CLEC12A | DAP10 | OX40 | CD3δ |
| CLEC12A | DAP10 | OX40 | CD3γ |
| CLEC12A | DAP10 | OX40 | CD3ε |
| CLEC12A | DAP10 | OX40 | FcγRI-γ |
| CLEC12A | DAP10 | OX40 | FcγRIII-γ |
| CLEC12A | DAP10 | OX40 | FcεRIβ |
| CLEC12A | DAP10 | OX40 | FcεRIγ |
| CLEC12A | DAP10 | OX40 | DAP10 |
| CLEC12A | DAP10 | OX40 | DAP12 |
| CLEC12A | DAP10 | OX40 | CD32 |
| CLEC12A | DAP10 | OX40 | CD79a |
| CLEC12A | DAP10 | OX40 | CD79b |
| CLEC12A | DAP10 | DAP10 | CD8 |
| CLEC12A | DAP10 | DAP10 | CD3ζ |
| CLEC12A | DAP10 | DAP10 | CD3δ |
| CLEC12A | DAP10 | DAP10 | CD3γ |
| CLEC12A | DAP10 | DAP10 | CD3ε |
| CLEC12A | DAP10 | DAP10 | FcγRI-γ |
| CLEC12A | DAP10 | DAP10 | FcγRIII-γ |
| CLEC12A | DAP10 | DAP10 | FcεRIβ |
| CLEC12A | DAP10 | DAP10 | FcεRIγ |
| CLEC12A | DAP10 | DAP10 | DAP10 |
| CLEC12A | DAP10 | DAP10 | DAP12 |
| CLEC12A | DAP10 | DAP10 | CD32 |
| CLEC12A | DAP10 | DAP10 | CD79a |
| CLEC12A | DAP10 | DAP10 | CD79b |
| CLEC12A | DAP10 | DAP12 | CD8 |
| CLEC12A | DAP10 | DAP12 | CD3ζ |
| CLEC12A | DAP10 | DAP12 | CD3δ |
| CLEC12A | DAP10 | DAP12 | CD3γ |
| CLEC12A | DAP10 | DAP12 | CD3ε |
| CLEC12A | DAP10 | DAP12 | FcγRI-γ |
| CLEC12A | DAP10 | DAP12 | FcγRIII-γ |
| CLEC12A | DAP10 | DAP12 | FcεRIβ |
| CLEC12A | DAP10 | DAP12 | FcεRIγ |
| CLEC12A | DAP10 | DAP12 | DAP10 |
| CLEC12A | DAP10 | DAP12 | DAP12 |
| CLEC12A | DAP10 | DAP12 | CD32 |
| CLEC12A | DAP10 | DAP12 | CD79a |
| CLEC12A | DAP10 | DAP12 | CD79b |
| CLEC12A | DAP10 | MyD88 | CD8 |
| CLEC12A | DAP10 | MyD88 | CD3ζ |
| CLEC12A | DAP10 | MyD88 | CD3δ |
| CLEC12A | DAP10 | MyD88 | CD3γ |
| CLEC12A | DAP10 | MyD88 | CD3ε |
| CLEC12A | DAP10 | MyD88 | FcγRI-γ |
| CLEC12A | DAP10 | MyD88 | FcγRIII-γ |
| CLEC12A | DAP10 | MyD88 | FcεRIβ |
| CLEC12A | DAP10 | MyD88 | FcεRIγ |
| CLEC12A | DAP10 | MyD88 | DAP10 |
| CLEC12A | DAP10 | MyD88 | DAP12 |
| CLEC12A | DAP10 | MyD88 | CD32 |
| CLEC12A | DAP10 | MyD88 | CD79a |
| CLEC12A | DAP10 | MyD88 | CD79b |
| CLEC12A | DAP10 | CD7 | CD8 |
| CLEC12A | DAP10 | CD7 | CD3ζ |
| CLEC12A | DAP10 | CD7 | CD3δ |
| CLEC12A | DAP10 | CD7 | CD3γ |
| CLEC12A | DAP10 | CD7 | CD3ε |
| CLEC12A | DAP10 | CD7 | FcγRI-γ |
| CLEC12A | DAP10 | CD7 | FcγRIII-γ |
| CLEC12A | DAP10 | CD7 | FcεRIβ |
| CLEC12A | DAP10 | CD7 | FcεRIγ |
| CLEC12A | DAP10 | CD7 | DAP10 |
| CLEC12A | DAP10 | CD7 | DAP12 |
| CLEC12A | DAP10 | CD7 | CD32 |
| CLEC12A | DAP10 | CD7 | CD79a |
| CLEC12A | DAP10 | CD7 | CD79b |
| CLEC12A | DAP10 | BTNL3 | CD8 |
| CLEC12A | DAP10 | BTNL3 | CD3ζ |
| CLEC12A | DAP10 | BTNL3 | CD3δ |
| CLEC12A | DAP10 | BTNL3 | CD3γ |
| CLEC12A | DAP10 | BTNL3 | CD3ε |
| CLEC12A | DAP10 | BTNL3 | FcγRI-γ |
| CLEC12A | DAP10 | BTNL3 | FcγRIII-γ |
| CLEC12A | DAP10 | BTNL3 | FcεRIβ |
| CLEC12A | DAP10 | BTNL3 | FcεRIγ |
| CLEC12A | DAP10 | BTNL3 | DAP10 |
| CLEC12A | DAP10 | BTNL3 | DAP12 |
| CLEC12A | DAP10 | BTNL3 | CD32 |
| CLEC12A | DAP10 | BTNL3 | CD79a |
| CLEC12A | DAP10 | BTNL3 | CD79b |
| CLEC12A | DAP10 | NKG2D | CD8 |
| CLEC12A | DAP10 | NKG2D | CD3ζ |
| CLEC12A | DAP10 | NKG2D | CD3δ |
| CLEC12A | DAP10 | NKG2D | CD3γ |
| CLEC12A | DAP10 | NKG2D | CD3ε |
| CLEC12A | DAP10 | NKG2D | FcγRI-γ |
| CLEC12A | DAP10 | NKG2D | FcγRIII-γ |
| CLEC12A | DAP10 | NKG2D | FcεRIβ |
| CLEC12A | DAP10 | NKG2D | FcεRIγ |
| CLEC12A | DAP10 | NKG2D | DAP10 |
| CLEC12A | DAP10 | NKG2D | DAP12 |
| CLEC12A | DAP10 | NKG2D | CD32 |
| CLEC12A | DAP10 | NKG2D | CD79a |
| CLEC12A | DAP10 | NKG2D | CD79b |
| CLEC12A | DAP12 | CD28 | CD8 |
| CLEC12A | DAP12 | CD28 | CD3ζ |
| CLEC12A | DAP12 | CD28 | CD3δ |
| CLEC12A | DAP12 | CD28 | CD3γ |
| CLEC12A | DAP12 | CD28 | CD3ε |
| CLEC12A | DAP12 | CD28 | FcγRI-γ |
| CLEC12A | DAP12 | CD28 | FcγRIII-γ |
| CLEC12A | DAP12 | CD28 | FcεRIβ |
| CLEC12A | DAP12 | CD28 | FcεRIγ |
| CLEC12A | DAP12 | CD28 | DAP10 |
| CLEC12A | DAP12 | CD28 | DAP12 |
| CLEC12A | DAP12 | CD28 | CD32 |
| CLEC12A | DAP12 | CD28 | CD79a |
| CLEC12A | DAP12 | CD28 | CD79b |
| CLEC12A | DAP12 | CD8 | CD8 |
| CLEC12A | DAP12 | CD8 | CD3ζ |
| CLEC12A | DAP12 | CD8 | CD3δ |
| CLEC12A | DAP12 | CD8 | CD3γ |
| CLEC12A | DAP12 | CD8 | CD3ε |
| CLEC12A | DAP12 | CD8 | FcγRI-γ |
| CLEC12A | DAP12 | CD8 | FcγRIII-γ |
| CLEC12A | DAP12 | CD8 | FcεRIβ |
| CLEC12A | DAP12 | CD8 | FcεRIγ |
| CLEC12A | DAP12 | CD8 | DAP10 |
| CLEC12A | DAP12 | CD8 | DAP12 |
| CLEC12A | DAP12 | CD8 | CD32 |
| CLEC12A | DAP12 | CD8 | CD79a |
| CLEC12A | DAP12 | CD8 | CD79b |
| CLEC12A | DAP12 | CD4 | CD8 |
| CLEC12A | DAP12 | CD4 | CD3ζ |
| CLEC12A | DAP12 | CD4 | CD3δ |
| CLEC12A | DAP12 | CD4 | CD3γ |
| CLEC12A | DAP12 | CD4 | CD3ε |
| CLEC12A | DAP12 | CD4 | FcγRI-γ |
| CLEC12A | DAP12 | CD4 | FcγRIII-γ |
| CLEC12A | DAP12 | CD4 | FcεRIβ |
| CLEC12A | DAP12 | CD4 | FcεRIγ |
| CLEC12A | DAP12 | CD4 | DAP10 |
| CLEC12A | DAP12 | CD4 | DAP12 |
| CLEC12A | DAP12 | CD4 | CD32 |
| CLEC12A | DAP12 | CD4 | CD79a |
| CLEC12A | DAP12 | CD4 | CD79b |
| CLEC12A | DAP12 | b2c | CD8 |
| CLEC12A | DAP12 | b2c | CD3ζ |
| CLEC12A | DAP12 | b2c | CD3δ |
| CLEC12A | DAP12 | b2c | CD3γ |

TABLE 3-continued

Third Generation CARs

| ScFv | Co-stimulatory Signal | Co-stimulatory Signal | Signal Domain |
|---|---|---|---|
| CLEC12A | DAP12 | b2c | CD3ε |
| CLEC12A | DAP12 | b2c | FcγRI-γ |
| CLEC12A | DAP12 | b2c | FcγRIII-γ |
| CLEC12A | DAP12 | b2c | FcεRIβ |
| CLEC12A | DAP12 | b2c | FcεRIγ |
| CLEC12A | DAP12 | b2c | DAP10 |
| CLEC12A | DAP12 | b2c | DAP12 |
| CLEC12A | DAP12 | b2c | CD32 |
| CLEC12A | DAP12 | b2c | CD79a |
| CLEC12A | DAP12 | b2c | CD79b |
| CLEC12A | DAP12 | CD137/41BB | CD8 |
| CLEC12A | DAP12 | CD137/41BB | CD3ζ |
| CLEC12A | DAP12 | CD137/41BB | CD3δ |
| CLEC12A | DAP12 | CD137/41BB | CD3γ |
| CLEC12A | DAP12 | CD137/41BB | CD3ε |
| CLEC12A | DAP12 | CD137/41BB | FcγRI-γ |
| CLEC12A | DAP12 | CD137/41BB | FcγRIII-γ |
| CLEC12A | DAP12 | CD137/41BB | FcεRIβ |
| CLEC12A | DAP12 | CD137/41BB | FcεRIγ |
| CLEC12A | DAP12 | CD137/41BB | DAP10 |
| CLEC12A | DAP12 | CD137/41BB | DAP12 |
| CLEC12A | DAP12 | CD137/41BB | CD32 |
| CLEC12A | DAP12 | CD137/41BB | CD79a |
| CLEC12A | DAP12 | CD137/41BB | CD79b |
| CLEC12A | DAP12 | ICOS | CD8 |
| CLEC12A | DAP12 | ICOS | CD3ζ |
| CLEC12A | DAP12 | ICOS | CD3δ |
| CLEC12A | DAP12 | ICOS | CD3γ |
| CLEC12A | DAP12 | ICOS | CD3ε |
| CLEC12A | DAP12 | ICOS | FcγRI-γ |
| CLEC12A | DAP12 | ICOS | FcγRIII-γ |
| CLEC12A | DAP12 | ICOS | FcεRIβ |
| CLEC12A | DAP12 | ICOS | FcεRIγ |
| CLEC12A | DAP12 | ICOS | DAP10 |
| CLEC12A | DAP12 | ICOS | DAP12 |
| CLEC12A | DAP12 | ICOS | CD32 |
| CLEC12A | DAP12 | ICOS | CD79a |
| CLEC12A | DAP12 | ICOS | CD79b |
| CLEC12A | DAP12 | CD27 | CD8 |
| CLEC12A | DAP12 | CD27 | CD3ζ |
| CLEC12A | DAP12 | CD27 | CD3δ |
| CLEC12A | DAP12 | CD27 | CD3γ |
| CLEC12A | DAP12 | CD27 | CD3ε |
| CLEC12A | DAP12 | CD27 | FcγRI-γ |
| CLEC12A | DAP12 | CD27 | FcγRIII-γ |
| CLEC12A | DAP12 | CD27 | FcεRIβ |
| CLEC12A | DAP12 | CD27 | FcεRIγ |
| CLEC12A | DAP12 | CD27 | DAP10 |
| CLEC12A | DAP12 | CD27 | DAP12 |
| CLEC12A | DAP12 | CD27 | CD32 |
| CLEC12A | DAP12 | CD27 | CD79a |
| CLEC12A | DAP12 | CD27 | CD79b |
| CLEC12A | DAP12 | CD28δ | CD8 |
| CLEC12A | DAP12 | CD28δ | CD3ζ |
| CLEC12A | DAP12 | CD28δ | CD3δ |
| CLEC12A | DAP12 | CD28δ | CD3γ |
| CLEC12A | DAP12 | CD28δ | CD3ε |
| CLEC12A | DAP12 | CD28δ | FcγRI-γ |
| CLEC12A | DAP12 | CD28δ | FcγRIII-γ |
| CLEC12A | DAP12 | CD28δ | FcεRIβ |
| CLEC12A | DAP12 | CD28δ | FcεRIγ |
| CLEC12A | DAP12 | CD28δ | DAP10 |
| CLEC12A | DAP12 | CD28δ | DAP12 |
| CLEC12A | DAP12 | CD28δ | CD32 |
| CLEC12A | DAP12 | CD28δ | CD79a |
| CLEC12A | DAP12 | CD28δ | CD79b |
| CLEC12A | DAP12 | CD80 | CD8 |
| CLEC12A | DAP12 | CD80 | CD3ζ |
| CLEC12A | DAP12 | CD80 | CD3δ |
| CLEC12A | DAP12 | CD80 | CD3γ |
| CLEC12A | DAP12 | CD80 | CD3ε |
| CLEC12A | DAP12 | CD80 | FcγRI-γ |
| CLEC12A | DAP12 | CD80 | FcγRIII-γ |
| CLEC12A | DAP12 | CD80 | FcεRIβ |
| CLEC12A | DAP12 | CD80 | FcεRIγ |
| CLEC12A | DAP12 | CD80 | DAP10 |
| CLEC12A | DAP12 | CD80 | DAP12 |
| CLEC12A | DAP12 | CD80 | CD32 |
| CLEC12A | DAP12 | CD80 | CD79a |
| CLEC12A | DAP12 | CD80 | CD79b |
| CLEC12A | DAP12 | CD86 | CD8 |
| CLEC12A | DAP12 | CD86 | CD3ζ |
| CLEC12A | DAP12 | CD86 | CD3δ |
| CLEC12A | DAP12 | CD86 | CD3γ |
| CLEC12A | DAP12 | CD86 | CD3ε |
| CLEC12A | DAP12 | CD86 | FcγRI-γ |
| CLEC12A | DAP12 | CD86 | FcγRIII-γ |
| CLEC12A | DAP12 | CD86 | FcεRIβ |
| CLEC12A | DAP12 | CD86 | FcεRIγ |
| CLEC12A | DAP12 | CD86 | DAP10 |
| CLEC12A | DAP12 | CD86 | DAP12 |
| CLEC12A | DAP12 | CD86 | CD32 |
| CLEC12A | DAP12 | CD86 | CD79a |
| CLEC12A | DAP12 | CD86 | CD79b |
| CLEC12A | DAP12 | OX40 | CD8 |
| CLEC12A | DAP12 | OX40 | CD3ζ |
| CLEC12A | DAP12 | OX40 | CD3δ |
| CLEC12A | DAP12 | OX40 | CD3γ |
| CLEC12A | DAP12 | OX40 | CD3ε |
| CLEC12A | DAP12 | OX40 | FcγRI-γ |
| CLEC12A | DAP12 | OX40 | FcγRIII-γ |
| CLEC12A | DAP12 | OX40 | FcεRIβ |
| CLEC12A | DAP12 | OX40 | FcεRIγ |
| CLEC12A | DAP12 | OX40 | DAP10 |
| CLEC12A | DAP12 | OX40 | DAP12 |
| CLEC12A | DAP12 | OX40 | CD32 |
| CLEC12A | DAP12 | OX40 | CD79a |
| CLEC12A | DAP12 | OX40 | CD79b |
| CLEC12A | DAP12 | DAP10 | CD8 |
| CLEC12A | DAP12 | DAP10 | CD3ζ |
| CLEC12A | DAP12 | DAP10 | CD3δ |
| CLEC12A | DAP12 | DAP10 | CD3γ |
| CLEC12A | DAP12 | DAP10 | CD3ε |
| CLEC12A | DAP12 | DAP10 | FcγRI-γ |
| CLEC12A | DAP12 | DAP10 | FcγRIII-γ |
| CLEC12A | DAP12 | DAP10 | FcεRIβ |
| CLEC12A | DAP12 | DAP10 | FcεRIγ |
| CLEC12A | DAP12 | DAP10 | DAP10 |
| CLEC12A | DAP12 | DAP10 | DAP12 |
| CLEC12A | DAP12 | DAP10 | CD32 |
| CLEC12A | DAP12 | DAP10 | CD79a |
| CLEC12A | DAP12 | DAP10 | CD79b |
| CLEC12A | DAP12 | DAP12 | CD8 |
| CLEC12A | DAP12 | DAP12 | CD3ζ |
| CLEC12A | DAP12 | DAP12 | CD3δ |
| CLEC12A | DAP12 | DAP12 | CD3γ |
| CLEC12A | DAP12 | DAP12 | CD3ε |
| CLEC12A | DAP12 | DAP12 | FcγRI-γ |
| CLEC12A | DAP12 | DAP12 | FcγRIII-γ |
| CLEC12A | DAP12 | DAP12 | FcεRIβ |
| CLEC12A | DAP12 | DAP12 | FcεRIγ |
| CLEC12A | DAP12 | DAP12 | DAP10 |
| CLEC12A | DAP12 | DAP12 | DAP12 |
| CLEC12A | DAP12 | DAP12 | CD32 |
| CLEC12A | DAP12 | DAP12 | CD79a |
| CLEC12A | DAP12 | DAP12 | CD79b |
| CLEC12A | DAP12 | MyD88 | CD8 |
| CLEC12A | DAP12 | MyD88 | CD3ζ |
| CLEC12A | DAP12 | MyD88 | CD3δ |
| CLEC12A | DAP12 | MyD88 | CD3γ |
| CLEC12A | DAP12 | MyD88 | CD3ε |
| CLEC12A | DAP12 | MyD88 | FcγRI-γ |
| CLEC12A | DAP12 | MyD88 | FcγRIII-γ |
| CLEC12A | DAP12 | MyD88 | FcεRIβ |
| CLEC12A | DAP12 | MyD88 | FcεRIγ |
| CLEC12A | DAP12 | MyD88 | DAP10 |
| CLEC12A | DAP12 | MyD88 | DAP12 |
| CLEC12A | DAP12 | MyD88 | CD32 |
| CLEC12A | DAP12 | MyD88 | CD79a |
| CLEC12A | DAP12 | MyD88 | CD79b |

TABLE 3-continued

Third Generation CARs

| ScFv | Co-stimulatory Signal | Co-stimulatory Signal | Signal Domain |
|---|---|---|---|
| CLEC12A | DAP12 | CD7 | CD8 |
| CLEC12A | DAP12 | CD7 | CD3ζ |
| CLEC12A | DAP12 | CD7 | CD3δ |
| CLEC12A | DAP12 | CD7 | CD3γ |
| CLEC12A | DAP12 | CD7 | CD3ε |
| CLEC12A | DAP12 | CD7 | FcγRI-γ |
| CLEC12A | DAP12 | CD7 | FcγRIII-γ |
| CLEC12A | DAP12 | CD7 | FcεRIβ |
| CLEC12A | DAP12 | CD7 | FcεRIγ |
| CLEC12A | DAP12 | CD7 | DAP10 |
| CLEC12A | DAP12 | CD7 | DAP12 |
| CLEC12A | DAP 12 | CD7 | CD32 |
| CLEC12A | DAP12 | CD7 | CD79a |
| CLEC12A | DAP12 | CD7 | CD79b |
| CLEC12A | DAP12 | BTNL3 | CD8 |
| CLEC12A | DAP12 | BTNL3 | CD3ζ |
| CLEC12A | DAP12 | BTNL3 | CD3δ |
| CLEC12A | DAP12 | BTNL3 | CD3γ |
| CLEC12A | DAP12 | BTNL3 | CD3ε |
| CLEC12A | DAP12 | BTNL3 | FcγRI-γ |
| CLEC12A | DAP12 | BTNL3 | FcγRIII-γ |
| CLEC12A | DAP12 | BTNL3 | FcεRIβ |
| CLEC12A | DAP12 | BTNL3 | FcεRIγ |
| CLEC12A | DAP12 | BTNL3 | DAP10 |
| CLEC12A | DAP12 | BTNL3 | DAP12 |
| CLEC12A | DAP12 | BTNL3 | CD32 |
| CLEC12A | DAP12 | BTNL3 | CD79a |
| CLEC12A | DAP12 | BTNL3 | CD79b |
| CLEC12A | DAP12 | NKG2D | CD8 |
| CLEC12A | DAP12 | NKG2D | CD3ζ |
| CLEC12A | DAP12 | NKG2D | CD3δ |
| CLEC12A | DAP12 | NKG2D | CD3γ |
| CLEC12A | DAP12 | NKG2D | CD3ε |
| CLEC12A | DAP12 | NKG2D | FcγRI-γ |
| CLEC12A | DAP12 | NKG2D | FcγRIII-γ |
| CLEC12A | DAP12 | NKG2D | FcεRIβ |
| CLEC12A | DAP12 | NKG2D | FcεRIγ |
| CLEC12A | DAP12 | NKG2D | DAP10 |
| CLEC12A | DAP12 | NKG2D | DAP12 |
| CLEC12A | DAP12 | NKG2D | CD32 |
| CLEC12A | DAP12 | NKG2D | CD79a |
| CLEC12A | DAP12 | NKG2D | CD79b |
| CLEC12A | MyD88 | CD28 | CD8 |
| CLEC12A | MyD88 | CD28 | CD3ζ |
| CLEC12A | MyD88 | CD28 | CD3δ |
| CLEC12A | MyD88 | CD28 | CD3γ |
| CLEC12A | MyD88 | CD28 | CD3ε |
| CLEC12A | MyD88 | CD28 | FcγRI-γ |
| CLEC12A | MyD88 | CD28 | FcγRIII-γ |
| CLEC12A | MyD88 | CD28 | FcεRIβ |
| CLEC12A | MyD88 | CD28 | FcεRIγ |
| CLEC12A | MyD88 | CD28 | DAP10 |
| CLEC12A | MyD88 | CD28 | DAP12 |
| CLEC12A | MyD88 | CD28 | CD32 |
| CLEC12A | MyD88 | CD28 | CD79a |
| CLEC12A | MyD88 | CD28 | CD79b |
| CLEC12A | MyD88 | CD8 | CD8 |
| CLEC12A | MyD88 | CD8 | CD3ζ |
| CLEC12A | MyD88 | CD8 | CD3δ |
| CLEC12A | MyD88 | CD8 | CD3γ |
| CLEC12A | MyD88 | CD8 | CD3ε |
| CLEC12A | MyD88 | CD8 | FcγRI-γ |
| CLEC12A | MyD88 | CD8 | FcγRIII-γ |
| CLEC12A | MyD88 | CD8 | FcεRIβ |
| CLEC12A | MyD88 | CD8 | FcεRIγ |
| CLEC12A | MyD88 | CD8 | DAP10 |
| CLEC12A | MyD88 | CD8 | DAP12 |
| CLEC12A | MyD88 | CD8 | CD32 |
| CLEC12A | MyD88 | CD8 | CD79a |
| CLEC12A | MyD88 | CD8 | CD79b |
| CLEC12A | MyD88 | CD4 | CD8 |
| CLEC12A | MyD88 | CD4 | CD3ζ |
| CLEC12A | MyD88 | CD4 | CD3δ |
| CLEC12A | MyD88 | CD4 | CD3γ |
| CLEC12A | MyD88 | CD4 | CD3ε |
| CLEC12A | MyD88 | CD4 | FcγRI-γ |
| CLEC12A | MyD88 | CD4 | FcγRIII-γ |
| CLEC12A | MyD88 | CD4 | FcεRIβ |
| CLEC12A | MyD88 | CD4 | FcεRIγ |
| CLEC12A | MyD88 | CD4 | DAP10 |
| CLEC12A | MyD88 | CD4 | DAP12 |
| CLEC12A | MyD88 | CD4 | CD32 |
| CLEC12A | MyD88 | CD4 | CD79a |
| CLEC12A | MyD88 | CD4 | CD79b |
| CLEC12A | MyD88 | b2c | CD8 |
| CLEC12A | MyD88 | b2c | CD3ζ |
| CLEC12A | MyD88 | b2c | CD3δ |
| CLEC12A | MyD88 | b2c | CD3γ |
| CLEC12A | MyD88 | b2c | CD3ε |
| CLEC12A | MyD88 | b2c | FcγRI-γ |
| CLEC12A | MyD88 | b2c | FcγRIII-γ |
| CLEC12A | MyD88 | b2c | FcεRIβ |
| CLEC12A | MyD88 | b2c | FcεRIγ |
| CLEC12A | MyD88 | b2c | DAP10 |
| CLEC12A | MyD88 | b2c | DAP12 |
| CLEC12A | MyD88 | b2c | CD32 |
| CLEC12A | MyD88 | b2c | CD79a |
| CLEC12A | MyD88 | b2c | CD79b |
| CLEC12A | MyD88 | CD137/41BB | CD8 |
| CLEC12A | MyD88 | CD137/41BB | CD3ζ |
| CLEC12A | MyD88 | CD137/41BB | CD3δ |
| CLEC12A | MyD88 | CD137/41BB | CD3γ |
| CLEC12A | MyD88 | CD137/41BB | CD3ε |
| CLEC12A | MyD88 | CD137/41BB | FcγRI-γ |
| CLEC12A | MyD88 | CD137/41BB | FcγRIII-γ |
| CLEC12A | MyD88 | CD137/41BB | FcεRIβ |
| CLEC12A | MyD88 | CD137/41BB | FcεRIγ |
| CLEC12A | MyD88 | CD137/41BB | DAP10 |
| CLEC12A | MyD88 | CD137/41BB | DAP12 |
| CLEC12A | MyD88 | CD137/41BB | CD32 |
| CLEC12A | MyD88 | CD137/41BB | CD79a |
| CLEC12A | MyD88 | CD137/41BB | CD79b |
| CLEC12A | MyD88 | ICOS | CD8 |
| CLEC12A | MyD88 | ICOS | CD3ζ |
| CLEC12A | MyD88 | ICOS | CD3δ |
| CLEC12A | MyD88 | ICOS | CD3γ |
| CLEC12A | MyD88 | ICOS | CD3ε |
| CLEC12A | MyD88 | ICOS | FcγRI-γ |
| CLEC12A | MyD88 | ICOS | FcγRIII-γ |
| CLEC12A | MyD88 | ICOS | FcεRIβ |
| CLEC12A | MyD88 | ICOS | FcεRIγ |
| CLEC12A | MyD88 | ICOS | DAP10 |
| CLEC12A | MyD88 | ICOS | DAP12 |
| CLEC12A | MyD88 | ICOS | CD32 |
| CLEC12A | MyD88 | ICOS | CD79a |
| CLEC12A | MyD88 | ICOS | CD79b |
| CLEC12A | MyD88 | CD27 | CD8 |
| CLEC12A | MyD88 | CD27 | CD3ζ |
| CLEC12A | MyD88 | CD27 | CD3δ |
| CLEC12A | MyD88 | CD27 | CD3γ |
| CLEC12A | MyD88 | CD27 | CD3ε |
| CLEC12A | MyD88 | CD27 | FcγRI-γ |
| CLEC12A | MyD88 | CD27 | FcγRIII-γ |
| CLEC12A | MyD88 | CD27 | FcεRIβ |
| CLEC12A | MyD88 | CD27 | FcεRIγ |
| CLEC12A | MyD88 | CD27 | DAP10 |
| CLEC12A | MyD88 | CD27 | DAP12 |
| CLEC12A | MyD88 | CD27 | CD32 |
| CLEC12A | MyD88 | CD27 | CD79a |
| CLEC12A | MyD88 | CD27 | CD79b |
| CLEC12A | MyD88 | CD28δ | CD8 |
| CLEC12A | MyD88 | CD28δ | CD3ζ |
| CLEC12A | MyD88 | CD28δ | CD3δ |
| CLEC12A | MyD88 | CD28δ | CD3γ |
| CLEC12A | MyD88 | CD28δ | CD3ε |
| CLEC12A | MyD88 | CD28δ | FcγRI-γ |
| CLEC12A | MyD88 | CD28δ | FcγRIII-γ |
| CLEC12A | MyD88 | CD28δ | FcεRIβ |
| CLEC12A | MyD88 | CD28δ | FcεRIγ |
| CLEC12A | MyD88 | CD28δ | DAP10 |

TABLE 3-continued

Third Generation CARs

| ScFv | Co-stimulatory Signal | Co-stimulatory Signal | Signal Domain |
|---|---|---|---|
| CLEC12A | MyD88 | CD28δ | DAP12 |
| CLEC12A | MyD88 | CD28δ | CD32 |
| CLEC12A | MyD88 | CD28δ | CD79a |
| CLEC12A | MyD88 | CD28δ | CD79b |
| CLEC12A | MyD88 | CD80 | CD8 |
| CLEC12A | MyD88 | CD80 | CD3ζ |
| CLEC12A | MyD88 | CD80 | CD3δ |
| CLEC12A | MyD88 | CD80 | CD3γ |
| CLEC12A | MyD88 | CD80 | CD3ε |
| CLEC12A | MyD88 | CD80 | FcγRI-γ |
| CLEC12A | MyD88 | CD80 | FcγRIII-γ |
| CLEC12A | MyD88 | CD80 | FcεRIβ |
| CLEC12A | MyD88 | CD80 | FcεRIγ |
| CLEC12A | MyD88 | CD80 | DAP10 |
| CLEC12A | MyD88 | CD80 | DAP12 |
| CLEC12A | MyD88 | CD80 | CD32 |
| CLEC12A | MyD88 | CD80 | CD79a |
| CLEC12A | MyD88 | CD80 | CD79b |
| CLEC12A | MyD88 | CD86 | CD8 |
| CLEC12A | MyD88 | CD86 | CD3ζ |
| CLEC12A | MyD88 | CD86 | CD3δ |
| CLEC12A | MyD88 | CD86 | CD3γ |
| CLEC12A | MyD88 | CD86 | CD3ε |
| CLEC12A | MyD88 | CD86 | FcγRI-γ |
| CLEC12A | MyD88 | CD86 | FcγRIII-γ |
| CLEC12A | MyD88 | CD86 | FcεRIβ |
| CLEC12A | MyD88 | CD86 | FcεRIγ |
| CLEC12A | MyD88 | CD86 | DAP10 |
| CLEC12A | MyD88 | CD86 | DAP12 |
| CLEC12A | MyD88 | CD86 | CD32 |
| CLEC12A | MyD88 | CD86 | CD79a |
| CLEC12A | MyD88 | CD86 | CD79b |
| CLEC12A | MyD88 | OX40 | CD8 |
| CLEC12A | MyD88 | OX40 | CD3ζ |
| CLEC12A | MyD88 | OX40 | CD3δ |
| CLEC12A | MyD88 | OX40 | CD3γ |
| CLEC12A | MyD88 | OX40 | CD3ε |
| CLEC12A | MyD88 | OX40 | FcγRI-γ |
| CLEC12A | MyD88 | OX40 | FcγRIII-γ |
| CLEC12A | MyD88 | OX40 | FcεRIβ |
| CLEC12A | MyD88 | OX40 | FcεRIγ |
| CLEC12A | MyD88 | OX40 | DAP10 |
| CLEC12A | MyD88 | OX40 | DAP12 |
| CLEC12A | MyD88 | OX40 | CD32 |
| CLEC12A | MyD88 | OX40 | CD79a |
| CLEC12A | MyD88 | OX40 | CD79b |
| CLEC12A | MyD88 | DAP10 | CD8 |
| CLEC12A | MyD88 | DAP10 | CD3ζ |
| CLEC12A | MyD88 | DAP10 | CD3δ |
| CLEC12A | MyD88 | DAP10 | CD3γ |
| CLEC12A | MyD88 | DAP10 | CD3ε |
| CLEC12A | MyD88 | DAP10 | FcγRI-γ |
| CLEC12A | MyD88 | DAP10 | FcγRIII-γ |
| CLEC12A | MyD88 | DAP10 | FcεRIβ |
| CLEC12A | MyD88 | DAP10 | FcεRIγ |
| CLEC12A | MyD88 | DAP10 | DAP10 |
| CLEC12A | MyD88 | DAP10 | DAP12 |
| CLEC12A | MyD88 | DAP10 | CD32 |
| CLEC12A | MyD88 | DAP10 | CD79a |
| CLEC12A | MyD88 | DAP10 | CD79b |
| CLEC12A | MyD88 | DAP12 | CD8 |
| CLEC12A | MyD88 | DAP12 | CD3ζ |
| CLEC12A | MyD88 | DAP12 | CD3δ |
| CLEC12A | MyD88 | DAP12 | CD3γ |
| CLEC12A | MyD88 | DAP12 | CD3ε |
| CLEC12A | MyD88 | DAP12 | FcγRI-γ |
| CLEC12A | MyD88 | DAP12 | FcγRIII-γ |
| CLEC12A | MyD88 | DAP12 | FcεRIβ |
| CLEC12A | MyD88 | DAP12 | FcεRIγ |
| CLEC12A | MyD88 | DAP12 | DAP10 |
| CLEC12A | MyD88 | DAP12 | DAP12 |
| CLEC12A | MyD88 | DAP12 | CD32 |
| CLEC12A | MyD88 | DAP12 | CD79a |
| CLEC12A | MyD88 | DAP12 | CD79b |
| CLEC12A | MyD88 | MyD88 | CD8 |
| CLEC12A | MyD88 | MyD88 | CD3ζ |
| CLEC12A | MyD88 | MyD88 | CD3δ |
| CLEC12A | MyD88 | MyD88 | CD3γ |
| CLEC12A | MyD88 | MyD88 | CD3ε |
| CLEC12A | MyD88 | MyD88 | FcγRI-γ |
| CLEC12A | MyD88 | MyD88 | FcγRIII-γ |
| CLEC12A | MyD88 | MyD88 | FcεRIβ |
| CLEC12A | MyD88 | MyD88 | FcεRIγ |
| CLEC12A | MyD88 | MyD88 | DAP10 |
| CLEC12A | MyD88 | MyD88 | DAP12 |
| CLEC12A | MyD88 | MyD88 | CD32 |
| CLEC12A | MyD88 | MyD88 | CD79a |
| CLEC12A | MyD88 | MyD88 | CD79b |
| CLEC12A | MyD88 | CD7 | CD8 |
| CLEC12A | MyD88 | CD7 | CD3ζ |
| CLEC12A | MyD88 | CD7 | CD3δ |
| CLEC12A | MyD88 | CD7 | CD3γ |
| CLEC12A | MyD88 | CD7 | CD3ε |
| CLEC12A | MyD88 | CD7 | FcγRI-γ |
| CLEC12A | MyD88 | CD7 | FcγRIII-γ |
| CLEC12A | MyD88 | CD7 | FcεRIβ |
| CLEC12A | MyD88 | CD7 | FcεRIγ |
| CLEC12A | MyD88 | CD7 | DAP10 |
| CLEC12A | MyD88 | CD7 | DAP12 |
| CLEC12A | MyD88 | CD7 | CD32 |
| CLEC12A | MyD88 | CD7 | CD79a |
| CLEC12A | MyD88 | CD7 | CD79b |
| CLEC12A | MyD88 | BTNL3 | CD8 |
| CLEC12A | MyD88 | BTNL3 | CD3ζ |
| CLEC12A | MyD88 | BTNL3 | CD3δ |
| CLEC12A | MyD88 | BTNL3 | CD3γ |
| CLEC12A | MyD88 | BTNL3 | CD3ε |
| CLEC12A | MyD88 | BTNL3 | FcγRI-γ |
| CLEC12A | MyD88 | BTNL3 | FcγRIII-γ |
| CLEC12A | MyD88 | BTNL3 | FcεRIβ |
| CLEC12A | MyD88 | BTNL3 | FcεRIγ |
| CLEC12A | MyD88 | BTNL3 | DAP10 |
| CLEC12A | MyD88 | BTNL3 | DAP12 |
| CLEC12A | MyD88 | BTNL3 | CD32 |
| CLEC12A | MyD88 | BTNL3 | CD79a |
| CLEC12A | MyD88 | BTNL3 | CD79b |
| CLEC12A | MyD88 | NKG2D | CD8 |
| CLEC12A | MyD88 | NKG2D | CD3ζ |
| CLEC12A | MyD88 | NKG2D | CD3δ |
| CLEC12A | MyD88 | NKG2D | CD3γ |
| CLEC12A | MyD88 | NKG2D | CD3ε |
| CLEC12A | MyD88 | NKG2D | FcγRI-γ |
| CLEC12A | MyD88 | NKG2D | FcγRIII-γ |
| CLEC12A | MyD88 | NKG2D | FcεRIβ |
| CLEC12A | MyD88 | NKG2D | FcεRIγ |
| CLEC12A | MyD88 | NKG2D | DAP10 |
| CLEC12A | MyD88 | NKG2D | DAP12 |
| CLEC12A | MyD88 | NKG2D | CD32 |
| CLEC12A | MyD88 | NKG2D | CD79a |
| CLEC12A | MyD88 | NKG2D | CD79b |
| CLEC12A | CD7 | CD28 | CD8 |
| CLEC12A | CD7 | CD28 | CD3ζ |
| CLEC12A | CD7 | CD28 | CD3δ |
| CLEC12A | CD7 | CD28 | CD3γ |
| CLEC12A | CD7 | CD28 | CD3ε |
| CLEC12A | CD7 | CD28 | FcγRI-γ |
| CLEC12A | CD7 | CD28 | FcγRIII-γ |
| CLEC12A | CD7 | CD28 | FcεRIβ |
| CLEC12A | CD7 | CD28 | FcεRIγ |
| CLEC12A | CD7 | CD28 | DAP10 |
| CLEC12A | CD7 | CD28 | DAP12 |
| CLEC12A | CD7 | CD28 | CD32 |
| CLEC12A | CD7 | CD28 | CD79a |
| CLEC12A | CD7 | CD28 | CD79b |
| CLEC12A | CD7 | CD8 | CD8 |
| CLEC12A | CD7 | CD8 | CD3ζ |
| CLEC12A | CD7 | CD8 | CD3δ |
| CLEC12A | CD7 | CD8 | CD3γ |
| CLEC12A | CD7 | CD8 | CD3ε |
| CLEC12A | CD7 | CD8 | FcγRI-γ |

TABLE 3-continued

Third Generation CARs

| ScFv | Co-stimulatory Signal | Co-stimulatory Signal | Signal Domain |
|---|---|---|---|
| CLEC12A | CD7 | CD8 | FcγRIII-γ |
| CLEC12A | CD7 | CD8 | FcεRIβ |
| CLEC12A | CD7 | CD8 | FCεRIγ |
| CLEC12A | CD7 | CD8 | DAP10 |
| CLEC12A | CD7 | CD8 | DAP12 |
| CLEC12A | CD7 | CD8 | CD32 |
| CLEC12A | CD7 | CD8 | CD79a |
| CLEC12A | CD7 | CD8 | CD79b |
| CLEC12A | CD7 | CD4 | CD8 |
| CLEC12A | CD7 | CD4 | CD3ζ |
| CLEC12A | CD7 | CD4 | CD3δ |
| CLEC12A | CD7 | CD4 | CD3γ |
| CLEC12A | CD7 | CD4 | CD3ε |
| CLEC12A | CD7 | CD4 | FcγRI-γ |
| CLEC12A | CD7 | CD4 | FcγRIII-γ |
| CLEC12A | CD7 | CD4 | FcεRIβ |
| CLEC12A | CD7 | CD4 | FcεRIγ |
| CLEC12A | CD7 | CD4 | DAP10 |
| CLEC12A | CD7 | CD4 | DAP12 |
| CLEC12A | CD7 | CD4 | CD32 |
| CLEC12A | CD7 | CD4 | CD79a |
| CLEC12A | CD7 | CD4 | CD79b |
| CLEC12A | CD7 | b2c | CD8 |
| CLEC12A | CD7 | b2c | CD3ζ |
| CLEC12A | CD7 | b2c | CD3δ |
| CLEC12A | CD7 | b2c | CD3γ |
| CLEC12A | CD7 | b2c | CD3ε |
| CLEC12A | CD7 | b2c | FcγRI-γ |
| CLEC12A | CD7 | b2c | FcγRIII-γ |
| CLEC12A | CD7 | b2c | FcεRIβ |
| CLEC12A | CD7 | b2c | FcεRIγ |
| CLEC12A | CD7 | b2c | DAP10 |
| CLEC12A | CD7 | b2c | DAP12 |
| CLEC12A | CD7 | b2c | CD32 |
| CLEC12A | CD7 | b2c | CD79a |
| CLEC12A | CD7 | b2c | CD79b |
| CLEC12A | CD7 | CD137/41BB | CD8 |
| CLEC12A | CD7 | CD137/41BB | CD3ζ |
| CLEC12A | CD7 | CD137/41BB | CD3δ |
| CLEC12A | CD7 | CD137/41BB | CD3γ |
| CLEC12A | CD7 | CD137/41BB | CD3ε |
| CLEC12A | CD7 | CD137/41BB | FcγRI-γ |
| CLEC12A | CD7 | CD137/41BB | FcγRIII-γ |
| CLEC12A | CD7 | CD137/41BB | FcεRIβ |
| CLEC12A | CD7 | CD137/41BB | FcεRIγ |
| CLEC12A | CD7 | CD137/41BB | DAP10 |
| CLEC12A | CD7 | CD137/41BB | DAP12 |
| CLEC12A | CD7 | CD137/41BB | CD32 |
| CLEC12A | CD7 | CD137/41BB | CD79a |
| CLEC12A | CD7 | CD137/41BB | CD79b |
| CLEC12A | CD7 | ICOS | CD8 |
| CLEC12A | CD7 | ICOS | CD3ζ |
| CLEC12A | CD7 | ICOS | CD3δ |
| CLEC12A | CD7 | ICOS | CD3γ |
| CLEC12A | CD7 | ICOS | CD3ε |
| CLEC12A | CD7 | ICOS | FcγRI-γ |
| CLEC12A | CD7 | ICOS | FcγRIII-γ |
| CLEC12A | CD7 | ICOS | FcεRIβ |
| CLEC12A | CD7 | ICOS | FcεRIγ |
| CLEC12A | CD7 | ICOS | DAP10 |
| CLEC12A | CD7 | ICOS | DAP12 |
| CLEC12A | CD7 | ICOS | CD32 |
| CLEC12A | CD7 | ICOS | CD79a |
| CLEC12A | CD7 | ICOS | CD79b |
| CLEC12A | CD7 | CD27 | CD8 |
| CLEC12A | CD7 | CD27 | CD3ζ |
| CLEC12A | CD7 | CD27 | CD3δ |
| CLEC12A | CD7 | CD27 | CD3γ |
| CLEC12A | CD7 | CD27 | CD3ε |
| CLEC12A | CD7 | CD27 | FcγRI-γ |
| CLEC12A | CD7 | CD27 | FcγRIII-γ |
| CLEC12A | CD7 | CD27 | FcεRIβ |
| CLEC12A | CD7 | CD27 | FcεRIγ |
| CLEC12A | CD7 | CD27 | DAP10 |
| CLEC12A | CD7 | CD27 | DAP12 |
| CLEC12A | CD7 | CD27 | CD32 |
| CLEC12A | CD7 | CD27 | CD79a |
| CLEC12A | CD7 | CD27 | CD79b |
| CLEC12A | CD7 | CD28δ | CD8 |
| CLEC12A | CD7 | CD28δ | CD3ζ |
| CLEC12A | CD7 | CD28δ | CD3δ |
| CLEC12A | CD7 | CD28δ | CD3γ |
| CLEC12A | CD7 | CD28δ | CD3ε |
| CLEC12A | CD7 | CD28δ | FcγRI-γ |
| CLEC12A | CD7 | CD28δ | FcγRIII-γ |
| CLEC12A | CD7 | CD28δ | FcεRIβ |
| CLEC12A | CD7 | CD28δ | FcεRIγ |
| CLEC12A | CD7 | CD28δ | DAP10 |
| CLEC12A | CD7 | CD28δ | DAP12 |
| CLEC12A | CD7 | CD28δ | CD32 |
| CLEC12A | CD7 | CD28δ | CD79a |
| CLEC12A | CD7 | CD28δ | CD79b |
| CLEC12A | CD7 | CD80 | CD8 |
| CLEC12A | CD7 | CD80 | CD3ζ |
| CLEC12A | CD7 | CD80 | CD3δ |
| CLEC12A | CD7 | CD80 | CD3γ |
| CLEC12A | CD7 | CD80 | CD3ε |
| CLEC12A | CD7 | CD80 | FcγRI-γ |
| CLEC12A | CD7 | CD80 | FcγRIII-γ |
| CLEC12A | CD7 | CD80 | FcεRIβ |
| CLEC12A | CD7 | CD80 | FcεRIγ |
| CLEC12A | CD7 | CD80 | DAP10 |
| CLEC12A | CD7 | CD80 | DAP12 |
| CLEC12A | CD7 | CD80 | CD32 |
| CLEC12A | CD7 | CD80 | CD79a |
| CLEC12A | CD7 | CD80 | CD79b |
| CLEC12A | CD7 | CD86 | CD8 |
| CLEC12A | CD7 | CD86 | CD3ζ |
| CLEC12A | CD7 | CD86 | CD3δ |
| CLEC12A | CD7 | CD86 | CD3γ |
| CLEC12A | CD7 | CD86 | CD3ε |
| CLEC12A | CD7 | CD86 | FcγRI-γ |
| CLEC12A | CD7 | CD86 | FcγRIII-γ |
| CLEC12A | CD7 | CD86 | FcεRIβ |
| CLEC12A | CD7 | CD86 | FcεRIγ |
| CLEC12A | CD7 | CD86 | DAP10 |
| CLEC12A | CD7 | CD86 | DAP12 |
| CLEC12A | CD7 | CD86 | CD32 |
| CLEC12A | CD7 | CD86 | CD79a |
| CLEC12A | CD7 | CD86 | CD79b |
| CLEC12A | CD7 | OX40 | CD8 |
| CLEC12A | CD7 | OX40 | CD3ζ |
| CLEC12A | CD7 | OX40 | CD3δ |
| CLEC12A | CD7 | OX40 | CD3γ |
| CLEC12A | CD7 | OX40 | CD3ε |
| CLEC12A | CD7 | OX40 | FcγRI-γ |
| CLEC12A | CD7 | OX40 | FcγRIII-γ |
| CLEC12A | CD7 | OX40 | FcεRIβ |
| CLEC12A | CD7 | OX40 | FcεRIγ |
| CLEC12A | CD7 | OX40 | DAP10 |
| CLEC12A | CD7 | OX40 | DAP12 |
| CLEC12A | CD7 | OX40 | CD32 |
| CLEC12A | CD7 | OX40 | CD79a |
| CLEC12A | CD7 | OX40 | CD79b |
| CLEC12A | CD7 | DAP10 | CD8 |
| CLEC12A | CD7 | DAP10 | CD3ζ |
| CLEC12A | CD7 | DAP10 | CD3δ |
| CLEC12A | CD7 | DAP10 | CD3γ |
| CLEC12A | CD7 | DAP10 | CD3ε |
| CLEC12A | CD7 | DAP10 | FcγRI-γ |
| CLEC12A | CD7 | DAP10 | FcγRIII-γ |
| CLEC12A | CD7 | DAP10 | FcεRIβ |
| CLEC12A | CD7 | DAP10 | FcεRIγ |
| CLEC12A | CD7 | DAP10 | DAP10 |
| CLEC12A | CD7 | DAP10 | DAP12 |
| CLEC12A | CD7 | DAP10 | CD32 |
| CLEC12A | CD7 | DAP10 | CD79a |
| CLEC12A | CD7 | DAP10 | CD79b |
| CLEC12A | CD7 | DAP12 | CD8 |
| CLEC12A | CD7 | DAP12 | CD3ζ |

TABLE 3-continued

Third Generation CARs

| ScFv | Co-stimulatory Signal | Co-stimulatory Signal | Signal Domain |
|---|---|---|---|
| CLEC12A | CD7 | DAP12 | CD3δ |
| CLEC12A | CD7 | DAP12 | CD3γ |
| CLEC12A | CD7 | DAP12 | CD3ε |
| CLEC12A | CD7 | DAP12 | FcγRI-γ |
| CLEC12A | CD7 | DAP12 | FcγRIII-γ |
| CLEC12A | CD7 | DAP12 | FcεRIβ |
| CLEC12A | CD7 | DAP12 | FcεRIγ |
| CLEC12A | CD7 | DAP12 | DAP10 |
| CLEC12A | CD7 | DAP12 | DAP12 |
| CLEC12A | CD7 | DAP12 | CD32 |
| CLEC12A | CD7 | DAP12 | CD79a |
| CLEC12A | CD7 | DAP12 | CD79b |
| CLEC12A | CD7 | MyD88 | CD8 |
| CLEC12A | CD7 | MyD88 | CD3ζ |
| CLEC12A | CD7 | MyD88 | CD3δ |
| CLEC12A | CD7 | MyD88 | CD3γ |
| CLEC12A | CD7 | MyD88 | CD3ε |
| CLEC12A | CD7 | MyD88 | FcγRI-γ |
| CLEC12A | CD7 | MyD88 | FcγRIII-γ |
| CLEC12A | CD7 | MyD88 | FcεRIβ |
| CLEC12A | CD7 | MyD88 | FcεRIγ |
| CLEC12A | CD7 | MyD88 | DAP10 |
| CLEC12A | CD7 | MyD88 | DAP12 |
| CLEC12A | CD7 | MyD88 | CD32 |
| CLEC12A | CD7 | MyD88 | CD79a |
| CLEC12A | CD7 | MyD88 | CD79b |
| CLEC12A | CD7 | CD7 | CD8 |
| CLEC12A | CD7 | CD7 | CD3ζ |
| CLEC12A | CD7 | CD7 | CD3δ |
| CLEC12A | CD7 | CD7 | CD3γ |
| CLEC12A | CD7 | CD7 | CD3ε |
| CLEC12A | CD7 | CD7 | FcγRI-γ |
| CLEC12A | CD7 | CD7 | FcγRIII-γ |
| CLEC12A | CD7 | CD7 | FcεRIβ |
| CLEC12A | CD7 | CD7 | FcεRIγ |
| CLEC12A | CD7 | CD7 | DAP10 |
| CLEC12A | CD7 | CD7 | DAP12 |
| CLEC12A | CD7 | CD7 | CD32 |
| CLEC12A | CD7 | CD7 | CD79a |
| CLEC12A | CD7 | CD7 | CD79b |
| CLEC12A | CD7 | BTNL3 | CD8 |
| CLEC12A | CD7 | BTNL3 | CD3ζ |
| CLEC12A | CD7 | BTNL3 | CD3δ |
| CLEC12A | CD7 | BTNL3 | CD3γ |
| CLEC12A | CD7 | BTNL3 | CD3ε |
| CLEC12A | CD7 | BTNL3 | FcγRI-γ |
| CLEC12A | CD7 | BTNL3 | FcγRIII-γ |
| CLEC12A | CD7 | BTNL3 | FcεRIβ |
| CLEC12A | CD7 | BTNL3 | FcεRIγ |
| CLEC12A | CD7 | BTNL3 | DAP10 |
| CLEC12A | CD7 | BTNL3 | DAP12 |
| CLEC12A | CD7 | BTNL3 | CD32 |
| CLEC12A | CD7 | BTNL3 | CD79a |
| CLEC12A | CD7 | BTNL3 | CD79b |
| CLEC12A | CD7 | NKG2D | CD8 |
| CLEC12A | CD7 | NKG2D | CD3ζ |
| CLEC12A | CD7 | NKG2D | CD3δ |
| CLEC12A | CD7 | NKG2D | CD3γ |
| CLEC12A | CD7 | NKG2D | CD3ε |
| CLEC12A | CD7 | NKG2D | FcγRI-γ |
| CLEC12A | CD7 | NKG2D | FcγRIII-γ |
| CLEC12A | CD7 | NKG2D | FcεRIβ |
| CLEC12A | CD7 | NKG2D | FcεRIγ |
| CLEC12A | CD7 | NKG2D | DAP10 |
| CLEC12A | CD7 | NKG2D | DAP12 |
| CLEC12A | CD7 | NKG2D | CD32 |
| CLEC12A | CD7 | NKG2D | CD79a |
| CLEC12A | CD7 | NKG2D | CD79b |
| CLEC12A | BTNL3 | CD28 | CD8 |
| CLEC12A | BTNL3 | CD28 | CD3ζ |
| CLEC12A | BTNL3 | CD28 | CD3δ |
| CLEC12A | BTNL3 | CD28 | CD3γ |
| CLEC12A | BTNL3 | CD28 | CD3ε |
| CLEC12A | BTNL3 | CD28 | FcγRI-γ |
| CLEC12A | BTNL3 | CD28 | FcγRIII-γ |
| CLEC12A | BTNL3 | CD28 | FcεRIβ |
| CLEC12A | BTNL3 | CD28 | FcεRIγ |
| CLEC12A | BTNL3 | CD28 | DAP10 |
| CLEC12A | BTNL3 | CD28 | DAP12 |
| CLEC12A | BTNL3 | CD28 | CD32 |
| CLEC12A | BTNL3 | CD28 | CD79a |
| CLEC12A | BTNL3 | CD28 | CD79b |
| CLEC12A | BTNL3 | CD8 | CD8 |
| CLEC12A | BTNL3 | CD8 | CD3ζ |
| CLEC12A | BTNL3 | CD8 | CD3δ |
| CLEC12A | BTNL3 | CD8 | CD3γ |
| CLEC12A | BTNL3 | CD8 | CD3ε |
| CLEC12A | BTNL3 | CD8 | FcγRI-γ |
| CLEC12A | BTNL3 | CD8 | FcγRIII-γ |
| CLEC12A | BTNL3 | CD8 | FcεRIβ |
| CLEC12A | BTNL3 | CD8 | FcεRIγ |
| CLEC12A | BTNL3 | CD8 | DAP10 |
| CLEC12A | BTNL3 | CD8 | DAP12 |
| CLEC12A | BTNL3 | CD8 | CD32 |
| CLEC12A | BTNL3 | CD8 | CD79a |
| CLEC12A | BTNL3 | CD8 | CD79b |
| CLEC12A | BTNL3 | CD4 | CD8 |
| CLEC12A | BTNL3 | CD4 | CD3ζ |
| CLEC12A | BTNL3 | CD4 | CD3δ |
| CLEC12A | BTNL3 | CD4 | CD3γ |
| CLEC12A | BTNL3 | CD4 | CD3ε |
| CLEC12A | BTNL3 | CD4 | FcγRI-γ |
| CLEC12A | BTNL3 | CD4 | FcγRIII-γ |
| CLEC12A | BTNL3 | CD4 | FcεRIβ |
| CLEC12A | BTNL3 | CD4 | FcεRIγ |
| CLEC12A | BTNL3 | CD4 | DAP10 |
| CLEC12A | BTNL3 | CD4 | DAP12 |
| CLEC12A | BTNL3 | CD4 | CD32 |
| CLEC12A | BTNL3 | CD4 | CD79a |
| CLEC12A | BTNL3 | CD4 | CD79b |
| CLEC12A | BTNL3 | b2c | CD8 |
| CLEC12A | BTNL3 | b2c | CD3ζ |
| CLEC12A | BTNL3 | b2c | CD3δ |
| CLEC12A | BTNL3 | b2c | CD3γ |
| CLEC12A | BTNL3 | b2c | CD3ε |
| CLEC12A | BTNL3 | b2c | FcγRI-γ |
| CLEC12A | BTNL3 | b2c | FcγRIII-γ |
| CLEC12A | BTNL3 | b2c | FcεRIβ |
| CLEC12A | BTNL3 | b2c | FcεRIγ |
| CLEC12A | BTNL3 | b2c | DAP10 |
| CLEC12A | BTNL3 | b2c | DAP12 |
| CLEC12A | BTNL3 | b2c | CD32 |
| CLEC12A | BTNL3 | b2c | CD79a |
| CLEC12A | BTNL3 | b2c | CD79b |
| CLEC12A | BTNL3 | CD137/41BB | CD8 |
| CLEC12A | BTNL3 | CD137/41BB | CD3ζ |
| CLEC12A | BTNL3 | CD137/41BB | CD3δ |
| CLEC12A | BTNL3 | CD137/41BB | CDγ |
| CLEC12A | BTNL3 | CD137/41BB | CD3ε |
| CLEC12A | BTNL3 | CD137/41BB | FcγRI-γ |
| CLEC12A | BTNL3 | CD137/41BB | FcγRIII-γ |
| CLEC12A | BTNL3 | CD137/41BB | FcεRIβ |
| CLEC12A | BTNL3 | CD137/41BB | FcεRIγ |
| CLEC12A | BTNL3 | CD137/41BB | DAP10 |
| CLEC12A | BTNL3 | CD137/41BB | DAP12 |
| CLEC12A | BTNL3 | CD137/41BB | CD32 |
| CLEC12A | BTNL3 | CD137/41BB | CD79a |
| CLEC12A | BTNL3 | CD137/41BB | CD79b |
| CLEC12A | BTNL3 | ICOS | CD8 |
| CLEC12A | BTNL3 | ICOS | CD3ζ |
| CLEC12A | BTNL3 | ICOS | CD3δ |
| CLEC12A | BTNL3 | ICOS | CD3γ |
| CLEC12A | BTNL3 | ICOS | CD3ε |
| CLEC12A | BTNL3 | ICOS | FcγRI-γ |
| CLEC12A | BTNL3 | ICOS | FcγRIII-γ |
| CLEC12A | BTNL3 | ICOS | FcεRIβ |
| CLEC12A | BTNL3 | ICOS | FcεRIγ |
| CLEC12A | BTNL3 | ICOS | DAP10 |
| CLEC12A | BTNL3 | ICOS | DAP12 |
| CLEC12A | BTNL3 | ICOS | CD32 |

TABLE 3-continued

Third Generation CARs

| ScFv | Co-stimulatory Signal | Co-stimulatory Signal | Signal Domain |
|---|---|---|---|
| CLEC12A | BTNL3 | ICOS | CD79a |
| CLEC12A | BTNL3 | ICOS | CD79b |
| CLEC12A | BTNL3 | CD27 | CD8 |
| CLEC12A | BTNL3 | CD27 | CD3ζ |
| CLEC12A | BTNL3 | CD27 | CD3δ |
| CLEC12A | BTNL3 | CD27 | CD3γ |
| CLEC12A | BTNL3 | CD27 | CD3ε |
| CLEC12A | BTNL3 | CD27 | FcγRI-γ |
| CLEC12A | BTNL3 | CD27 | FcγRIII-γ |
| CLEC12A | BTNL3 | CD27 | FcεRIβ |
| CLEC12A | BTNL3 | CD27 | FcεRIγ |
| CLEC12A | BTNL3 | CD27 | DAP10 |
| CLEC12A | BTNL3 | CD27 | DAP12 |
| CLEC12A | BTNL3 | CD27 | CD32 |
| CLEC12A | BTNL3 | CD27 | CD79a |
| CLEC12A | BTNL3 | CD27 | CD79b |
| CLEC12A | BTNL3 | CD28δ | CD8 |
| CLEC12A | BTNL3 | CD28δ | CD3ζ |
| CLEC12A | BTNL3 | CD28δ | CD3δ |
| CLEC12A | BTNL3 | CD28δ | CD3γ |
| CLEC12A | BTNL3 | CD28δ | CD3ε |
| CLEC12A | BTNL3 | CD28δ | FcγRI-γ |
| CLEC12A | BTNL3 | CD28δ | FcγRIII-γ |
| CLEC12A | BTNL3 | CD28δ | FcεRIβ |
| CLEC12A | BTNL3 | CD28δ | FcεRIγ |
| CLEC12A | BTNL3 | CD28δ | DAP10 |
| CLEC12A | BTNL3 | CD28δ | DAP12 |
| CLEC12A | BTNL3 | CD28δ | CD32 |
| CLEC12A | BTNL3 | CD28δ | CD79a |
| CLEC12A | BTNL3 | CD28δ | CD79b |
| CLEC12A | BTNL3 | CD80 | CD8 |
| CLEC12A | BTNL3 | CD80 | CD3ζ |
| CLEC12A | BTNL3 | CD80 | CD3δ |
| CLEC12A | BTNL3 | CD80 | CD3γ |
| CLEC12A | BTNL3 | CD80 | CD3ε |
| CLEC12A | BTNL3 | CD80 | FcγRI-γ |
| CLEC12A | BTNL3 | CD80 | FcγRIII-γ |
| CLEC12A | BTNL3 | CD80 | FcεRIβ |
| CLEC12A | BTNL3 | CD80 | FcεRIγ |
| CLEC12A | BTNL3 | CD80 | DAP10 |
| CLEC12A | BTNL3 | CD80 | DAP12 |
| CLEC12A | BTNL3 | CD80 | CD32 |
| CLEC12A | BTNL3 | CD80 | CD79a |
| CLEC12A | BTNL3 | CD80 | CD79b |
| CLEC12A | BTNL3 | CD86 | CD8 |
| CLEC12A | BTNL3 | CD86 | CD3ζ |
| CLEC12A | BTNL3 | CD86 | CD3δ |
| CLEC12A | BTNL3 | CD86 | CD3γ |
| CLEC12A | BTNL3 | CD86 | CD3ε |
| CLEC12A | BTNL3 | CD86 | FcγRI-γ |
| CLEC12A | BTNL3 | CD86 | FcγRIII-γ |
| CLEC12A | BTNL3 | CD86 | FcεRIβ |
| CLEC12A | BTNL3 | CD86 | FcεRIγ |
| CLEC12A | BTNL3 | CD86 | DAP10 |
| CLEC12A | BTNL3 | CD86 | DAP12 |
| CLEC12A | BTNL3 | CD86 | CD32 |
| CLEC12A | BTNL3 | CD86 | CD79a |
| CLEC12A | BTNL3 | CD86 | CD79b |
| CLEC12A | BTNL3 | OX40 | CD8 |
| CLEC12A | BTNL3 | OX40 | CD3ζ |
| CLEC12A | BTNL3 | OX40 | CD3δ |
| CLEC12A | BTNL3 | OX40 | CD3γ |
| CLEC12A | BTNL3 | OX40 | CD3ε |
| CLEC12A | BTNL3 | OX40 | FcγRI-γ |
| CLEC12A | BTNL3 | OX40 | FcγRIII-γ |
| CLEC12A | BTNL3 | OX40 | FcεRIβ |
| CLEC12A | BTNL3 | OX40 | FcεRIγ |
| CLEC12A | BTNL3 | OX40 | DAP10 |
| CLEC12A | BTNL3 | OX40 | DAP12 |
| CLEC12A | BTNL3 | OX40 | CD32 |
| CLEC12A | BTNL3 | OX40 | CD79a |
| CLEC12A | BTNL3 | OX40 | CD79b |
| CLEC12A | BTNL3 | DAP10 | CD8 |
| CLEC12A | BTNL3 | DAP10 | CD3ζ |
| CLEC12A | BTNL3 | DAP10 | CD3δ |
| CLEC12A | BTNL3 | DAP10 | CD3γ |
| CLEC12A | BTNL3 | DAP10 | CD3ε |
| CLEC12A | BTNL3 | DAP10 | FcγRI-γ |
| CLEC12A | BTNL3 | DAP10 | FcγRIII-γ |
| CLEC12A | BTNL3 | DAP10 | FcεRIβ |
| CLEC12A | BTNL3 | DAP10 | FcεRIγ |
| CLEC12A | BTNL3 | DAP10 | DAP10 |
| CLEC12A | BTNL3 | DAP10 | DAP12 |
| CLEC12A | BTNL3 | DAP10 | CD32 |
| CLEC12A | BTNL3 | DAP10 | CD79a |
| CLEC12A | BTNL3 | DAP10 | CD79b |
| CLEC12A | BTNL3 | DAP12 | CD8 |
| CLEC12A | BTNL3 | DAP12 | CD3ζ |
| CLEC12A | BTNL3 | DAP12 | CD3δ |
| CLEC12A | BTNL3 | DAP12 | CD3γ |
| CLEC12A | BTNL3 | DAP12 | CD3ε |
| CLEC12A | BTNL3 | DAP12 | FcγRI-γ |
| CLEC12A | BTNL3 | DAP12 | FcγRIII-γ |
| CLEC12A | BTNL3 | DAP12 | FcεRIβ |
| CLEC12A | BTNL3 | DAP12 | FcεRIγ |
| CLEC12A | BTNL3 | DAP12 | DAP10 |
| CLEC12A | BTNL3 | DAP12 | DAP12 |
| CLEC12A | BTNL3 | DAP12 | CD32 |
| CLEC12A | BTNL3 | DAP12 | CD79a |
| CLEC12A | BTNL3 | DAP12 | CD79b |
| CLEC12A | BTNL3 | MyD88 | CD8 |
| CLEC12A | BTNL3 | MyD88 | CD3ζ |
| CLEC12A | BTNL3 | MyD88 | CD3δ |
| CLEC12A | BTNL3 | MyD88 | CD3γ |
| CLEC12A | BTNL3 | MyD88 | CD3ε |
| CLEC12A | BTNL3 | MyD88 | FcγRI-γ |
| CLEC12A | BTNL3 | MyD88 | FcγRIII-γ |
| CLEC12A | BTNL3 | MyD88 | FcεRIβ |
| CLEC12A | BTNL3 | MyD88 | FcεRIγ |
| CLEC12A | BTNL3 | MyD88 | DAP10 |
| CLEC12A | BTNL3 | MyD88 | DAP12 |
| CLEC12A | BTNL3 | MyD88 | CD32 |
| CLEC12A | BTNL3 | MyD88 | CD79a |
| CLEC12A | BTNL3 | MyD88 | CD79b |
| CLEC12A | BTNL3 | CD7 | CD8 |
| CLEC12A | BTNL3 | CD7 | CD3ζ |
| CLEC12A | BTNL3 | CD7 | CD3δ |
| CLEC12A | BTNL3 | CD7 | CD3γ |
| CLEC12A | BTNL3 | CD7 | CD3ε |
| CLEC12A | BTNL3 | CD7 | FcγRI-γ |
| CLEC12A | BTNL3 | CD7 | FcγRIII-γ |
| CLEC12A | BTNL3 | CD7 | FcεRIβ |
| CLEC12A | BTNL3 | CD7 | FcεRIγ |
| CLEC12A | BTNL3 | CD7 | DAP10 |
| CLEC12A | BTNL3 | CD7 | DAP12 |
| CLEC12A | BTNL3 | CD7 | CD32 |
| CLEC12A | BTNL3 | CD7 | CD79a |
| CLEC12A | BTNL3 | CD7 | CD79b |
| CLEC12A | BTNL3 | BTNL3 | CD8 |
| CLEC12A | BTNL3 | BTNL3 | CD3ζ |
| CLEC12A | BTNL3 | BTNL3 | CD3δ |
| CLEC12A | BTNL3 | BTNL3 | CD3γ |
| CLEC12A | BTNL3 | BTNL3 | CD3ε |
| CLEC12A | BTNL3 | BTNL3 | FcγRI-γ |
| CLEC12A | BTNL3 | BTNL3 | FcγRIII-γ |
| CLEC12A | BTNL3 | BTNL3 | FcεRIβ |
| CLEC12A | BTNL3 | BTNL3 | FcεRIγ |
| CLEC12A | BTNL3 | BTNL3 | DAP10 |
| CLEC12A | BTNL3 | BTNL3 | DAP12 |
| CLEC12A | BTNL3 | BTNL3 | CD32 |
| CLEC12A | BTNL3 | BTNL3 | CD79a |
| CLEC12A | BTNL3 | BTNL3 | CD79b |
| CLEC12A | BTNL3 | NKG2D | CD8 |
| CLEC12A | BTNL3 | NKG2D | CD3ζ |
| CLEC12A | BTNL3 | NKG2D | CD3γ |
| CLEC12A | BTNL3 | NKG2D | CD3γ |
| CLEC12A | BTNL3 | NKG2D | CD3ε |
| CLEC12A | BTNL3 | NKG2D | FcγRI-γ |
| CLEC12A | BTNL3 | NKG2D | FcγRIII-γ |
| CLEC12A | BTNL3 | NKG2D | FcεRIβ |

TABLE 3-continued

Third Generation CARs

| ScFv | Co-stimulatory Signal | Co-stimulatory Signal | Signal Domain |
|---|---|---|---|
| CLEC12A | BTNL3 | NKG2D | FcεRIγ |
| CLEC12A | BTNL3 | NKG2D | DAP10 |
| CLEC12A | BTNL3 | NKG2D | DAP12 |
| CLEC12A | BTNL3 | NKG2D | CD32 |
| CLEC12A | BTNL3 | NKG2D | CD79a |
| CLEC12A | BTNL3 | NKG2D | CD79b |
| CLEC12A | NKG2D | CD28 | CD8 |
| CLEC12A | NKG2D | CD28 | CD3ζ |
| CLEC12A | NKG2D | CD28 | CD3δ |
| CLEC12A | NKG2D | CD28 | CD3γ |
| CLEC12A | NKG2D | CD28 | CD3ε |
| CLEC12A | NKG2D | CD28 | FcγRI-γ |
| CLEC12A | NKG2D | CD28 | FcγRIII-γ |
| CLEC12A | NKG2D | CD28 | FcεRIβ |
| CLEC12A | NKG2D | CD28 | FcεRIγ |
| CLEC12A | NKG2D | CD28 | DAP10 |
| CLEC12A | NKG2D | CD28 | DAP12 |
| CLEC12A | NKG2D | CD28 | CD32 |
| CLEC12A | NKG2D | CD28 | CD79a |
| CLEC12A | NKG2D | CD28 | CD79b |
| CLEC12A | NKG2D | CD8 | CD8 |
| CLEC12A | NKG2D | CD8 | CD3ζ |
| CLEC12A | NKG2D | CD8 | CD3δ |
| CLEC12A | NKG2D | CD8 | CD3γ |
| CLEC12A | NKG2D | CD8 | CD3ε |
| CLEC12A | NKG2D | CD8 | FcγRI-γ |
| CLEC12A | NKG2D | CD8 | FcγRIII-γ |
| CLEC12A | NKG2D | CD8 | FcεRIβ |
| CLEC12A | NKG2D | CD8 | FcεRIγ |
| CLEC12A | NKG2D | CD8 | DAP10 |
| CLEC12A | NKG2D | CD8 | DAP12 |
| CLEC12A | NKG2D | CD8 | CD32 |
| CLEC12A | NKG2D | CD8 | CD79a |
| CLEC12A | NKG2D | CD8 | CD79b |
| CLEC12A | NKG2D | CD4 | CD8 |
| CLEC12A | NKG2D | CD4 | CD3ζ |
| CLEC12A | NKG2D | CD4 | CD3δ |
| CLEC12A | NKG2D | CD4 | CD3γ |
| CLEC12A | NKG2D | CD4 | CD3ε |
| CLEC12A | NKG2D | CD4 | FcγRI-γ |
| CLEC12A | NKG2D | CD4 | FcγRIII-γ |
| CLEC12A | NKG2D | CD4 | FcεRIβ |
| CLEC12A | NKG2D | CD4 | FcεRIγ |
| CLEC12A | NKG2D | CD4 | DAP10 |
| CLEC12A | NKG2D | CD4 | DAP12 |
| CLEC12A | NKG2D | CD4 | CD32 |
| CLEC12A | NKG2D | CD4 | CD79a |
| CLEC12A | NKG2D | CD4 | CD79b |
| CLEC12A | NKG2D | b2c | CD8 |
| CLEC12A | NKG2D | b2c | CD3ζ |
| CLEC12A | NKG2D | b2c | CD3δ |
| CLEC12A | NKG2D | b2c | CD3γ |
| CLEC12A | NKG2D | b2c | CD3ε |
| CLEC12A | NKG2D | b2c | FcγRI-γ |
| CLEC12A | NKG2D | b2c | FcγRIII-γ |
| CLEC12A | NKG2D | b2c | FcεRIβ |
| CLEC12A | NKG2D | b2c | FcεRIγ |
| CLEC12A | NKG2D | b2c | DAP10 |
| CLEC12A | NKG2D | b2c | DAP12 |
| CLEC12A | NKG2D | b2c | CD32 |
| CLEC12A | NKG2D | b2c | CD79a |
| CLEC12A | NKG2D | b2c | CD79b |
| CLEC12A | NKG2D | CD137/41BB | CD8 |
| CLEC12A | NKG2D | CD137/41BB | CD3ζ |
| CLEC12A | NKG2D | CD137/41BB | CD3δ |
| CLEC12A | NKG2D | CD137/41BB | CD3γ |
| CLEC12A | NKG2D | CD137/41BB | CD3ε |
| CLEC12A | NKG2D | CD137/41BB | FcγRI-γ |
| CLEC12A | NKG2D | CD137/41BB | FcγRIII-γ |
| CLEC12A | NKG2D | CD137/41BB | FcεRIβ |
| CLEC12A | NKG2D | CD137/41BB | FcεRIγ |
| CLEC12A | NKG2D | CD137/41BB | DAP10 |
| CLEC12A | NKG2D | CD137/41BB | DAP12 |
| CLEC12A | NKG2D | CD137/41BB | CD32 |
| CLEC12A | NKG2D | CD137/41BB | CD79a |
| CLEC12A | NKG2D | CD137/41BB | CD79b |
| CLEC12A | NKG2D | ICOS | CD8 |
| CLEC12A | NKG2D | ICOS | CD3ζ |
| CLEC12A | NKG2D | ICOS | CD3δ |
| CLEC12A | NKG2D | ICOS | CD3γ |
| CLEC12A | NKG2D | ICOS | CD3ε |
| CLEC12A | NKG2D | ICOS | FcγRI-γ |
| CLEC12A | NKG2D | ICOS | FcγRIII-γ |
| CLEC12A | NKG2D | ICOS | FcεRIβ |
| CLEC12A | NKG2D | ICOS | FcεRIγ |
| CLEC12A | NKG2D | ICOS | DAP10 |
| CLEC12A | NKG2D | ICOS | DAP12 |
| CLEC12A | NKG2D | ICOS | CD32 |
| CLEC12A | NKG2D | ICOS | CD79a |
| CLEC12A | NKG2D | ICOS | CD79b |
| CLEC12A | NKG2D | CD27 | CD8 |
| CLEC12A | NKG2D | CD27 | CD3ζ |
| CLEC12A | NKG2D | CD27 | CD3δ |
| CLEC12A | NKG2D | CD27 | CD3γ |
| CLEC12A | NKG2D | CD27 | CD3ε |
| CLEC12A | NKG2D | CD27 | FcγRI-γ |
| CLEC12A | NKG2D | CD27 | FcγRIII-γ |
| CLEC12A | NKG2D | CD27 | FcεRIβ |
| CLEC12A | NKG2D | CD27 | FcεRIγ |
| CLEC12A | NKG2D | CD27 | DAP10 |
| CLEC12A | NKG2D | CD27 | DAP12 |
| CLEC12A | NKG2D | CD27 | CD32 |
| CLEC12A | NKG2D | CD27 | CD79a |
| CLEC12A | NKG2D | CD27 | CD79b |
| CLEC12A | NKG2D | CD28δ | CD8 |
| CLEC12A | NKG2D | CD28δ | CD3ζ |
| CLEC12A | NKG2D | CD28δ | CD3δ |
| CLEC12A | NKG2D | CD28δ | CD3γ |
| CLEC12A | NKG2D | CD28δ | CD3ε |
| CLEC12A | NKG2D | CD28δ | FcγRI-γ |
| CLEC12A | NKG2D | CD28δ | FcγRIII-γ |
| CLEC12A | NKG2D | CD28δ | FcεRIβ |
| CLEC12A | NKG2D | CD28δ | FcεRIγ |
| CLEC12A | NKG2D | CD28δ | DAP10 |
| CLEC12A | NKG2D | CD28δ | DAP12 |
| CLEC12A | NKG2D | CD28δ | CD32 |
| CLEC12A | NKG2D | CD28δ | CD79a |
| CLEC12A | NKG2D | CD28δ | CD79b |
| CLEC12A | NKG2D | CD80 | CD8 |
| CLEC12A | NKG2D | CD80 | CD3ζ |
| CLEC12A | NKG2D | CD80 | CD3δ |
| CLEC12A | NKG2D | CD80 | CD3γ |
| CLEC12A | NKG2D | CD80 | CD3ε |
| CLEC12A | NKG2D | CD80 | FcγRI-γ |
| CLEC12A | NKG2D | CD80 | FcγRIII-γ |
| CLEC12A | NKG2D | CD80 | FcεRIβ |
| CLEC12A | NKG2D | CD80 | FcεRIγ |
| CLEC12A | NKG2D | CD80 | DAP10 |
| CLEC12A | NKG2D | CD80 | DAP12 |
| CLEC12A | NKG2D | CD80 | CD32 |
| CLEC12A | NKG2D | CD80 | CD79a |
| CLEC12A | NKG2D | CD80 | CD79b |
| CLEC12A | NKG2D | CD86 | CD8 |
| CLEC12A | NKG2D | CD86 | CD3ζ |
| CLEC12A | NKG2D | CD86 | CD3δ |
| CLEC12A | NKG2D | CD86 | CD3γ |
| CLEC12A | NKG2D | CD86 | CD3ε |
| CLEC12A | NKG2D | CD86 | FcγRI-γ |
| CLEC12A | NKG2D | CD86 | FcγRIII-γ |
| CLEC12A | NKG2D | CD86 | FcεRIβ |
| CLEC12A | NKG2D | CD86 | FcεRIγ |
| CLEC12A | NKG2D | CD86 | DAP10 |
| CLEC12A | NKG2D | CD86 | DAP12 |
| CLEC12A | NKG2D | CD86 | CD32 |
| CLEC12A | NKG2D | CD86 | CD79a |
| CLEC12A | NKG2D | CD86 | CD79b |
| CLEC12A | NKG2D | OX40 | CD8 |
| CLEC12A | NKG2D | OX40 | CD3ζ |
| CLEC12A | NKG2D | OX40 | CD3δ |
| CLEC12A | NKG2D | OX40 | CD3γ |

TABLE 3-continued

Third Generation CARs

| ScFv | Co-stimulatory Signal | Co-stimulatory Signal | Signal Domain |
| --- | --- | --- | --- |
| CLEC12A | NKG2D | OX40 | CD3ε |
| CLEC12A | NKG2D | OX40 | FcγRI-γ |
| CLEC12A | NKG2D | OX40 | FcγRIII-γ |
| CLEC12A | NKG2D | OX40 | FcεRIβ |
| CLEC12A | NKG2D | OX40 | FcεRIγ |
| CLEC12A | NKG2D | OX40 | DAP10 |
| CLEC12A | NKG2D | OX40 | DAP12 |
| CLEC12A | NKG2D | OX40 | CD32 |
| CLEC12A | NKG2D | OX40 | CD79a |
| CLEC12A | NKG2D | OX40 | CD79b |
| CLEC12A | NKG2D | DAP10 | CD8 |
| CLEC12A | NKG2D | DAP10 | CD3ζ |
| CLEC12A | NKG2D | DAP10 | CD3δ |
| CLEC12A | NKG2D | DAP10 | CD3γ |
| CLEC12A | NKG2D | DAP10 | CD3ε |
| CLEC12A | NKG2D | DAP10 | FcγRI-γ |
| CLEC12A | NKG2D | DAP10 | FcγRIII-γ |
| CLEC12A | NKG2D | DAP10 | FcεRIβ |
| CLEC12A | NKG2D | DAP10 | FcεRIγ |
| CLEC12A | NKG2D | DAP10 | DAP10 |
| CLEC12A | NKG2D | DAP10 | DAP12 |
| CLEC12A | NKG2D | DAP10 | CD32 |
| CLEC12A | NKG2D | DAP10 | CD79a |
| CLEC12A | NKG2D | DAP10 | CD79b |
| CLEC12A | NKG2D | DAP12 | CD8 |
| CLEC12A | NKG2D | DAP12 | CD3ζ |
| CLEC12A | NKG2D | DAP12 | CD3δ |
| CLEC12A | NKG2D | DAP12 | CD3γ |
| CLEC12A | NKG2D | DAP12 | CD3ε |
| CLEC12A | NKG2D | DAP12 | FcγRI-γ |
| CLEC12A | NKG2D | DAP12 | FcγRIII-γ |
| CLEC12A | NKG2D | DAP12 | FcεRIβ |
| CLEC12A | NKG2D | DAP12 | FcεRIγ |
| CLEC12A | NKG2D | DAP12 | DAP10 |
| CLEC12A | NKG2D | DAP12 | DAP12 |
| CLEC12A | NKG2D | DAP12 | CD32 |
| CLEC12A | NKG2D | DAP12 | CD79a |
| CLEC12A | NKG2D | DAP12 | CD79b |
| CLEC12A | NKG2D | MyD88 | CD8 |
| CLEC12A | NKG2D | MyD88 | CD3ζ |
| CLEC12A | NKG2D | MyD88 | CD3δ |
| CLEC12A | NKG2D | MyD88 | CD3γ |
| CLEC12A | NKG2D | MyD88 | CD3ε |
| CLEC12A | NKG2D | MyD88 | FcγRI-γ |
| CLEC12A | NKG2D | MyD88 | FcγRIII-γ |
| CLEC12A | NKG2D | MyD88 | FcεRIβ |
| CLEC12A | NKG2D | MyD88 | FcεRIγ |
| CLEC12A | NKG2D | MyD88 | DAP10 |
| CLEC12A | NKG2D | MyD88 | DAP12 |
| CLEC12A | NKG2D | MyD88 | CD32 |
| CLEC12A | NKG2D | MyD88 | CD79a |
| CLEC12A | NKG2D | MyD88 | CD79b |
| CLEC12A | NKG2D | CD7 | CD8 |
| CLEC12A | NKG2D | CD7 | CD3ζ |
| CLEC12A | NKG2D | CD7 | CD3δ |
| CLEC12A | NKG2D | CD7 | CD3γ |
| CLEC12A | NKG2D | CD7 | CD3ε |
| CLEC12A | NKG2D | CD7 | FcγRI-γ |
| CLEC12A | NKG2D | CD7 | FcγRIII-γ |
| CLEC12A | NKG2D | CD7 | FcεRIβ |
| CLEC12A | NKG2D | CD7 | FcεRIγ |
| CLEC12A | NKG2D | CD7 | DAP10 |
| CLEC12A | NKG2D | CD7 | DAP12 |
| CLEC12A | NKG2D | CD7 | CD32 |
| CLEC12A | NKG2D | CD7 | CD79a |
| CLEC12A | NKG2D | CD7 | CD79b |
| CLEC12A | NKG2D | BTNL3 | CD8 |
| CLEC12A | NKG2D | BTNL3 | CD3ζ |
| CLEC12A | NKG2D | BTNL3 | CD3δ |
| CLEC12A | NKG2D | BTNL3 | CD3γ |
| CLEC12A | NKG2D | BTNL3 | CD3ε |
| CLEC12A | NKG2D | BTNL3 | FcγRI-γ |
| CLEC12A | NKG2D | BTNL3 | FcγRIII-γ |
| CLEC12A | NKG2D | BTNL3 | FcεRIβ |
| CLEC12A | NKG2D | BTNL3 | FcεRIγ |
| CLEC12A | NKG2D | BTNL3 | DAP10 |
| CLEC12A | NKG2D | BTNL3 | DAP12 |
| CLEC12A | NKG2D | BTNL3 | CD32 |
| CLEC12A | NKG2D | BTNL3 | CD79a |
| CLEC12A | NKG2D | BTNL3 | CD79b |
| CLEC12A | NKG2D | NKG2D | CD8 |
| CLEC12A | NKG2D | NKG2D | CD3ζ |
| CLEC12A | NKG2D | NKG2D | CD3δ |
| CLEC12A | NKG2D | NKG2D | CD3γ |
| CLEC12A | NKG2D | NKG2D | CD3ε |
| CLEC12A | NKG2D | NKG2D | FcγRI-γ |
| CLEC12A | NKG2D | NKG2D | FcγRIII-γ |
| CLEC12A | NKG2D | NKG2D | FcεRIβ |
| CLEC12A | NKG2D | NKG2D | FcεRIγ |
| CLEC12A | NKG2D | NKG2D | DAP10 |
| CLEC12A | NKG2D | NKG2D | DAP12 |
| CLEC12A | NKG2D | NKG2D | CD32 |
| CLEC12A | NKG2D | NKG2D | CD79a |
| CLEC12A | NKG2D | NKG2D | CD79b |

TABLE 4

CARs lacking Co-Simulatory Signal (for dual CAR approach)

| ScFv | Co-stimulatory Signal | Signal Domain |
| --- | --- | --- |
| CLEC12A | none | CD8 |
| CLEC12A | none | CD3ζ |
| CLEC12A | none | CD3δ |
| CLEC12A | none | CD3γ |
| CLEC12A | none | CD3ε |
| CLEC12A | none | FcγRI-γ |
| CLEC12A | none | FcγRIII-γ |
| CLEC12A | none | FcεRIβ |
| CLEC12A | none | FcεRIγ |
| CLEC12A | none | DAP10 |
| CLEC12A | none | DAP12 |
| CLEC12A | none | CD32 |
| CLEC12A | none | CD79a |
| CLEC12A | none | CD8 |
| CLEC12A | none | CD3ζ |
| CLEC12A | none | CD3δ |
| CLEC12A | none | CD3γ |
| CLEC12A | none | CD3ε |
| CLEC12A | none | FcγRI-γ |

TABLE 5

CARs lacking Signal Domain (for dual CAR approach)

| ScFv | Co-stimulatory Signal | Signal Domain |
| --- | --- | --- |
| CLEC12A | CD28 | none |
| CLEC12A | CD8 | none |
| CLEC12A | CD4 | none |
| CLEC12A | b2c | none |
| CLEC12A | CD137/41BB | none |
| CLEC12A | ICOS | none |
| CLEC12A | CD27 | none |
| CLEC12A | CD28δ | none |
| CLEC12A | CD80 | none |
| CLEC12A | CD86 | none |
| CLEC12A | OX40 | none |
| CLEC12A | DAP10 | none |
| CLEC12A | MyD88 | none |
| CLEC12A | CD7 | none |
| CLEC12A | DAP12 | none |
| CLEC12A | MyD88 | none |

TABLE 5-continued

CARs lacking Signal Domain (for dual CAR approach)

| ScFv | Co-stimulatory Signal | Signal Domain |
|---|---|---|
| CLEC12A | CD7 | none |
| CLEC12A | BTNL3 | none |
| CLEC12A | NKG2D | none |

TABLE 6

Third Generation CARs lacking Signal Domain (for dual CAR approach)

| ScFv | Co-stimulatory Signal | Co-stimulatory Signal | Signal Domain |
|---|---|---|---|
| CLEC12A | CD28 | CD28 | none |
| CLEC12A | CD28 | CD8 | none |
| CLEC12A | CD28 | CD4 | none |
| CLEC12A | CD28 | b2c | none |
| CLEC12A | CD28 | CD137/41BB | none |
| CLEC12A | CD28 | ICOS | none |
| CLEC12A | CD28 | CD27 | none |
| CLEC12A | CD28 | CD28δ | none |
| CLEC12A | CD28 | CD80 | none |
| CLEC12A | CD28 | CD86 | none |
| CLEC12A | CD28 | OX40 | none |
| CLEC12A | CD28 | DAP10 | none |
| CLEC12A | CD28 | MyD88 | none |
| CLEC12A | CD28 | CD7 | none |
| CLEC12A | CD28 | DAP12 | none |
| CLEC12A | CD28 | MyD88 | none |
| CLEC12A | CD28 | CD7 | none |
| CLEC12A | CD8 | CD28 | none |
| CLEC12A | CD8 | CD8 | none |
| CLEC12A | CD8 | CD4 | none |
| CLEC12A | CD8 | b2c | none |
| CLEC12A | CD8 | CD137/41BB | none |
| CLEC12A | CD8 | ICOS | none |
| CLEC12A | CD8 | CD27 | none |
| CLEC12A | CD8 | CD28δ | none |
| CLEC12A | CD8 | CD80 | none |
| CLEC12A | CD8 | CD86 | none |
| CLEC12A | CD8 | OX40 | none |
| CLEC12A | CD8 | DAP10 | none |
| CLEC12A | CD8 | MyD88 | none |
| CLEC12A | CD8 | CD7 | none |
| CLEC12A | CD8 | DAP12 | none |
| CLEC12A | CD8 | MyD88 | none |
| CLEC12A | CD8 | CD7 | none |
| CLEC12A | CD4 | CD28 | none |
| CLEC12A | CD4 | CD8 | none |
| CLEC12A | CD4 | CD4 | none |
| CLEC12A | CD4 | b2c | none |
| CLEC12A | CD4 | CD137/41BB | none |
| CLEC12A | CD4 | ICOS | none |
| CLEC12A | CD4 | CD27 | none |
| CLEC12A | CD4 | CD28δ | none |
| CLEC12A | CD4 | CD80 | none |
| CLEC12A | CD4 | CD86 | none |
| CLEC12A | CD4 | OX40 | none |
| CLEC12A | CD4 | DAP10 | none |
| CLEC12A | CD4 | MyD88 | none |
| CLEC12A | CD4 | CD7 | none |
| CLEC12A | CD4 | DAP12 | none |
| CLEC12A | CD4 | MyD88 | none |
| CLEC12A | CD4 | CD7 | none |
| CLEC12A | b2c | CD28 | none |
| CLEC12A | b2c | CD8 | none |
| CLEC12A | b2c | CD4 | none |
| CLEC12A | b2c | b2c | none |
| CLEC12A | b2c | CD137/41BB | none |
| CLEC12A | b2c | ICOS | none |
| CLEC12A | b2c | CD27 | none |
| CLEC12A | b2c | CD28δ | none |
| CLEC12A | b2c | CD80 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CLEC12A | b2c | CD86 | none |
| CLEC12A | b2c | OX40 | none |
| CLEC12A | b2c | DAP10 | none |
| CLEC12A | b2c | MyD88 | none |
| CLEC12A | b2c | CD7 | none |
| CLEC12A | b2c | DAP12 | none |
| CLEC12A | b2c | MyD88 | none |
| CLEC12A | b2c | CD7 | none |
| CLEC12A | CD137/41BB | CD28 | none |
| CLEC12A | CD137/41BB | CD8 | none |
| CLEC12A | CD137/41BB | CD4 | none |
| CLEC12A | CD137/41BB | b2c | none |
| CLEC12A | CD137/41BB | CD137/41BB | none |
| CLEC12A | CD137/41BB | ICOS | none |
| CLEC12A | CD137/41BB | CD27 | none |
| CLEC12A | CD137/41BB | CD28δ | none |
| CLEC12A | CD137/41BB | CD80 | none |
| CLEC12A | CD137/41BB | CD86 | none |
| CLEC12A | CD137/41BB | OX40 | none |
| CLEC12A | CD137/41BB | DAP10 | none |
| CLEC12A | CD137/41BB | MyD88 | none |
| CLEC12A | CD137/41BB | CD7 | none |
| CLEC12A | CD137/41BB | DAP12 | none |
| CLEC12A | CD137/41BB | MyD88 | none |
| CLEC12A | CD137/41BB | CD7 | none |
| CLEC12A | ICOS | CD28 | none |
| CLEC12A | ICOS | CD8 | none |
| CLEC12A | ICOS | CD4 | none |
| CLEC12A | ICOS | b2c | none |
| CLEC12A | ICOS | CD137/41BB | none |
| CLEC12A | ICOS | ICOS | none |
| CLEC12A | ICOS | CD27 | none |
| CLEC12A | ICOS | CD28δ | none |
| CLEC12A | ICOS | CD80 | none |
| CLEC12A | ICOS | CD86 | none |
| CLEC12A | ICOS | OX40 | none |
| CLEC12A | ICOS | DAP10 | none |
| CLEC12A | ICOS | MyD88 | none |
| CLEC12A | ICOS | CD7 | none |
| CLEC12A | ICOS | DAP12 | none |
| CLEC12A | ICOS | MyD88 | none |
| CLEC12A | ICOS | CD7 | none |
| CLEC12A | ICOS | CD28 | none |
| CLEC12A | ICOS | CD8 | none |
| CLEC12A | ICOS | CD4 | none |
| CLEC12A | ICOS | b2c | none |
| CLEC12A | ICOS | CD137/41BB | none |
| CLEC12A | ICOS | ICOS | none |
| CLEC12A | ICOS | CD27 | none |
| CLEC12A | ICOS | CD28δ | none |
| CLEC12A | ICOS | CD80 | none |
| CLEC12A | ICOS | CD86 | none |
| CLEC12A | ICOS | OX40 | none |
| CLEC12A | ICOS | DAP10 | none |
| CLEC12A | ICOS | MyD88 | none |
| CLEC12A | ICOS | CD7 | none |
| CLEC12A | ICOS | DAP12 | none |
| CLEC12A | ICOS | MyD88 | none |
| CLEC12A | ICOS | CD7 | none |
| CLEC12A | CD27 | CD28 | none |
| CLEC12A | CD27 | CD8 | none |
| CLEC12A | CD27 | CD4 | none |
| CLEC12A | CD27 | b2c | none |
| CLEC12A | CD27 | CD137/41BB | none |
| CLEC12A | CD27 | ICOS | none |
| CLEC12A | CD27 | CD27 | none |
| CLEC12A | CD27 | CD28δ | none |
| CLEC12A | CD27 | CD80 | none |
| CLEC12A | CD27 | CD86 | none |
| CLEC12A | CD27 | OX40 | none |
| CLEC12A | CD27 | DAP10 | none |
| CLEC12A | CD27 | MyD88 | none |
| CLEC12A | CD27 | CD7 | none |
| CLEC12A | CD27 | DAP12 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CLEC12A | CD27 | MyD88 | none |
| CLEC12A | CD27 | CD7 | none |
| CLEC12A | CD28δ | CD28 | none |
| CLEC12A | CD28δ | CD8 | none |
| CLEC12A | CD28δ | CD4 | none |
| CLEC12A | CD28δ | b2c | none |
| CLEC12A | CD28δ | CD137/41BB | none |
| CLEC12A | CD28δ | ICOS | none |
| CLEC12A | CD28δ | CD27 | none |
| CLEC12A | CD28δ | CD28δ | none |
| CLEC12A | CD28δ | CD80 | none |
| CLEC12A | CD28δ | CD86 | none |
| CLEC12A | CD28δ | OX40 | none |
| CLEC12A | CD28δ | DAP10 | none |
| CLEC12A | CD28δ | MyD88 | none |
| CLEC12A | CD28δ | CD7 | none |
| CLEC12A | CD28δ | DAP12 | none |
| CLEC12A | CD28δ | MyD88 | none |
| CLEC12A | CD28δ | CD7 | none |
| CLEC12A | CD80 | CD28 | none |
| CLEC12A | CD80 | CD8 | none |
| CLEC12A | CD80 | CD4 | none |
| CLEC12A | CD80 | b2c | none |
| CLEC12A | CD80 | CD137/41BB | none |
| CLEC12A | CD80 | ICOS | none |
| CLEC12A | CD80 | CD27 | none |
| CLEC12A | CD80 | CD28δ | none |
| CLEC12A | CD80 | CD80 | none |
| CLEC12A | CD80 | CD86 | none |
| CLEC12A | CD80 | OX40 | none |
| CLEC12A | CD80 | DAP10 | none |
| CLEC12A | CD80 | MyD88 | none |
| CLEC12A | CD80 | CD7 | none |
| CLEC12A | CD80 | DAP12 | none |
| CLEC12A | CD80 | MyD88 | none |
| CLEC12A | CD80 | CD7 | none |
| CLEC12A | CD86 | CD28 | none |
| CLEC12A | CD86 | CD8 | none |
| CLEC12A | CD86 | CD4 | none |
| CLEC12A | CD86 | b2c | none |
| CLEC12A | CD86 | CD137/41BB | none |
| CLEC12A | CD86 | ICOS | none |
| CLEC12A | CD86 | CD27 | none |
| CLEC12A | CD86 | CD28δ | none |
| CLEC12A | CD86 | CD80 | none |
| CLEC12A | CD86 | CD86 | none |
| CLEC12A | CD86 | OX40 | none |
| CLEC12A | CD86 | DAP10 | none |
| CLEC12A | CD86 | MyD88 | none |
| CLEC12A | CD86 | CD7 | none |
| CLEC12A | CD86 | DAP12 | none |
| CLEC12A | CD86 | MyD88 | none |
| CLEC12A | CD86 | CD7 | none |
| CLEC12A | OX40 | CD28 | none |
| CLEC12A | OX40 | CD8 | none |
| CLEC12A | OX40 | CD4 | none |
| CLEC12A | OX40 | b2c | none |
| CLEC12A | OX40 | CD137/41BB | none |
| CLEC12A | OX40 | ICOS | none |
| CLEC12A | OX40 | CD27 | none |
| CLEC12A | OX40 | CD28δ | none |
| CLEC12A | OX40 | CD80 | none |
| CLEC12A | OX40 | CD86 | none |
| CLEC12A | OX40 | OX40 | none |
| CLEC12A | OX40 | DAP10 | none |
| CLEC12A | OX40 | MyD88 | none |
| CLEC12A | OX40 | CD7 | none |
| CLEC12A | OX40 | DAP12 | none |
| CLEC12A | OX40 | MyD88 | none |
| CLEC12A | OX40 | CD7 | none |
| CLEC12A | DAP10 | CD28 | none |
| CLEC12A | DAP10 | CD8 | none |
| CLEC12A | DAP10 | CD4 | none |
| CLEC12A | DAP10 | b2c | none |
| CLEC12A | DAP10 | CD137/41BB | none |
| CLEC12A | DAP10 | ICOS | none |
| CLEC12A | DAP10 | CD27 | none |
| CLEC12A | DAP10 | CD28δ | none |
| CLEC12A | DAP10 | CD80 | none |
| CLEC12A | DAP10 | CD86 | none |
| CLEC12A | DAP10 | OX40 | none |
| CLEC12A | DAP10 | DAP10 | none |
| CLEC12A | DAP10 | MyD88 | none |
| CLEC12A | DAP10 | CD7 | none |
| CLEC12A | DAP10 | DAP12 | none |
| CLEC12A | DAP10 | MyD88 | none |
| CLEC12A | DAP10 | CD7 | none |
| CLEC12A | DAP12 | CD28 | none |
| CLEC12A | DAP12 | CD8 | none |
| CLEC12A | DAP12 | CD4 | none |
| CLEC12A | DAP12 | b2c | none |
| CLEC12A | DAP12 | CD137/41BB | none |
| CLEC12A | DAP12 | ICOS | none |
| CLEC12A | DAP12 | CD27 | none |
| CLEC12A | DAP12 | CD28δ | none |
| CLEC12A | DAP12 | CD80 | none |
| CLEC12A | DAP12 | CD86 | none |
| CLEC12A | DAP12 | OX40 | none |
| CLEC12A | DAP12 | DAP10 | none |
| CLEC12A | DAP12 | MyD88 | none |
| CLEC12A | DAP12 | CD7 | none |
| CLEC12A | DAP12 | DAP12 | none |
| CLEC12A | DAP12 | MyD88 | none |
| CLEC12A | DAP12 | CD7 | none |
| CLEC12A | MyD88 | CD28 | none |
| CLEC12A | MyD88 | CD8 | none |
| CLEC12A | MyD88 | CD4 | none |
| CLEC12A | MyD88 | b2c | none |
| CLEC12A | MyD88 | CD137/41BB | none |
| CLEC12A | MyD88 | ICOS | none |
| CLEC12A | MyD88 | CD27 | none |
| CLEC12A | MyD88 | CD28δ | none |
| CLEC12A | MyD88 | CD80 | none |
| CLEC12A | MyD88 | CD86 | none |
| CLEC12A | MyD88 | OX40 | none |
| CLEC12A | MyD88 | DAP10 | none |
| CLEC12A | MyD88 | MyD88 | none |
| CLEC12A | MyD88 | CD7 | none |
| CLEC12A | MyD88 | DAP12 | none |
| CLEC12A | MyD88 | MyD88 | none |
| CLEC12A | MyD88 | CD7 | none |
| CLEC12A | CD7 | CD28 | none |
| CLEC12A | CD7 | CD8 | none |
| CLEC12A | CD7 | CD4 | none |
| CLEC12A | CD7 | b2c | none |
| CLEC12A | CD7 | CD137/41BB | none |
| CLEC12A | CD7 | ICOS | none |
| CLEC12A | CD7 | CD27 | none |
| CLEC12A | CD7 | CD28δ | none |
| CLEC12A | CD7 | CD80 | none |
| CLEC12A | CD7 | CD86 | none |
| CLEC12A | CD7 | OX40 | none |
| CLEC12A | CD7 | DAP10 | none |
| CLEC12A | CD7 | MyD88 | none |
| CLEC12A | CD7 | CD7 | none |
| CLEC12A | CD7 | DAP12 | none |
| CLEC12A | CD7 | MyD88 | none |
| CLEC12A | CD7 | CD7 | none |
| CLEC12A | BTNL3 | CD28 | none |
| CLEC12A | BTNL3 | CD8 | none |
| CLEC12A | BTNL3 | CD4 | none |
| CLEC12A | BTNL3 | b2c | none |
| CLEC12A | BTNL3 | CD137/41BB | none |
| CLEC12A | BTNL3 | ICOS | none |
| CLEC12A | BTNL3 | CD27 | none |
| CLEC12A | BTNL3 | CD28δ | none |
| CLEC12A | BTNL3 | CD80 | none |
| CLEC12A | BTNL3 | CD86 | none |

TABLE 6-continued

Third Generation CARs lacking Signal
Domain (for dual CAR approach)

| ScFv | Co-stimulatory Signal | Co-stimulatory Signal | Signal Domain |
|---|---|---|---|
| CLEC12A | BTNL3 | OX40 | none |
| CLEC12A | BTNL3 | DAP10 | none |
| CLEC12A | BTNL3 | MyD88 | none |
| CLEC12A | BTNL3 | CD7 | none |
| CLEC12A | BTNL3 | DAP12 | none |
| CLEC12A | BTNL3 | MyD88 | none |
| CLEC12A | BTNL3 | CD7 | none |
| CLEC12A | NKG2D | CD28 | none |
| CLEC12A | NKG2D | CD8 | none |
| CLEC12A | NKG2D | CD4 | none |
| CLEC12A | NKG2D | b2c | none |
| CLEC12A | NKG2D | CD137/41BB | none |
| CLEC12A | NKG2D | ICOS | none |
| CLEC12A | NKG2D | CD27 | none |
| CLEC12A | NKG2D | CD28δ | none |
| CLEC12A | NKG2D | CD80 | none |
| CLEC12A | NKG2D | CD86 | none |
| CLEC12A | NKG2D | OX40 | none |
| CLEC12A | NKG2D | DAP10 | none |
| CLEC12A | NKG2D | MyD88 | none |
| CLEC12A | NKG2D | CD7 | none |
| CLEC12A | NKG2D | DAP12 | none |
| CLEC12A | NKG2D | MyD88 | none |
| CLEC12A | NKG2D | CD7 | none |

In some embodiments, the anti-CLEC12A binding agent is single chain variable fragment (scFv) antibody. The affinity/specificity of an anti-CLEC12A scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CLEC12A binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target CLEC12A and at least one additional tumor antigen. Also disclosed are CARs designed to work only in conjunction with another CAR that binds a different antigen, such as a tumor antigen. For example, in these embodiments, the endodomain of the disclosed CAR can contain only an signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, FIt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding proteinc\yclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed CLEC12A-specific CARs that allow expression of the CLEC12A-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as CD8$^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4$^+$ or CD8$^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4$^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8$^+$ T lymphocytes. In some embodiments, the T cells comprise γδ T cells, which possess a distinct T-cell receptor (TCR) having one γ chain and one δ chain instead of α and β chains.

Natural-killer (NK) cells are CD56$^+$ CD3$^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic CD8$^+$ T lymphocytes, NK cells launch cytotoxicity against tumor cells without the requirement for prior sensitization, and can also eradicate MHC-1-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Epstein-Barr virus (EBV)-induced lymphoproliferative diseases (EBV-LPDs) are a significant cause of morbidity and mortality for recipients of allogeneic hematopoietic cell transplantation (HCT), particularly in those who have received certain T-cell reactive Abs to prevent or treat GVHD. Prophylaxis and treatment by the adoptive transfer of EBV-specific T cells and the subsequent long-term restoration of immunity against EBV-associated lymphoproliferation have provided positive outcomes in the management of this uniformly fatal complication of bone marrow transfer. Therefore, in some embodiments, the disclosed immune effector cells are allogeneic or autologous EBV-specific cytotoxic T lymphocytes (CTLs). For example, this can involve isolating PBMCs from of an autologous or allogenic donor and enriching them for T cells by depletion of monocytes and NK cells. For example, the donor can be an EBV-seropositive donor. These T cells can then be stimulated with autologous EBV-seropostive or transformed lymphocytes. EBV antigens include latent membrane protein (LMP) and EBV nuclear antigen (EBNA) proteins, such as LMP-1, LMP-2A, and LMP-2B and EBNA-1, EBNA-2, EBNA-3A, EBNA-3B, EBNA-3C and EBNA-LP. These methods are described, for example, in Barker et al., Blood 2010 116(23):5045-49; Doubrovina, et al., Blood 2012 119(11):2644-56; Koehne, et al. Blood 2002 99(5):1730-40; and Smith et al. Cancer Res 2012 72(5):1116-25, which are incorporated by reference for these teachings.

Therapeutic Methods

Immune effector cells expressing the disclosed CARs can elicit an anti-tumor immune response against CLEC12A-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to CLEC12A.

Adoptive transfer of immune effector cells expressing chimeric antigen receptors is a promising anti-cancer therapeutic. Following the collection of a patient's immune effector cells, the cells may be genetically engineered to express the disclosed CLEC12A-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration.

Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any CLEC12A-expressing cell in a subject undergoing unregulated growth, invasion, or metastasis. Cancers that express CLEC12A include prostate cancer, ovarian cancer, adenocarcinoma of the lung, breast cancer, endometrial cancer, gastric cancer, colon cancer, and pancreatic cancer. CLEC12A has also been found on Jurkat cells. In some aspects, the cancer is a gallbladder cancer, exocrine adenocarcinoma, or apocrine adenocarcinomas. In some cases, the cancer comprises myelodysplastic syndrome, acute myeloid leukemia, or bi-phenotypic leukemia.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional- CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-β T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: CLEC12A Hybridoma Screening

Hybridomas selected from primary screening were sub cloned. ELISA Plates were coated with CLEC12A antigen (Thermo Fisher, cat #11896H07H50, lot #LCL07JL0401) diluted with DPBS (LONZA, cat #17-512F, lot #0000615334) to 1 ug/ml at RT for 1 hour, and then blocked with 1% BSA/DPBS 100 µl/well, room temperature for 1 hour. Supernatant from monoclonal hybridomas were then added to the coated plates (50 ul/well). Antibody was detected using goat anti Mouse Ig-HRP (1010-05), 1:4000 in TBST, 50 ul/well, room temperature for 45 mins, followed by ABTs/H2O2 for 10 mins. Clones 1F3, 1F8, 1G3, 2A10, 3F12, 4E3, 4E10, 5B2, 5F10, 6C7, 9A2, 11C7, 11H1, and 12D6 showed positive binding to CLEC12A.

Figure 1D:
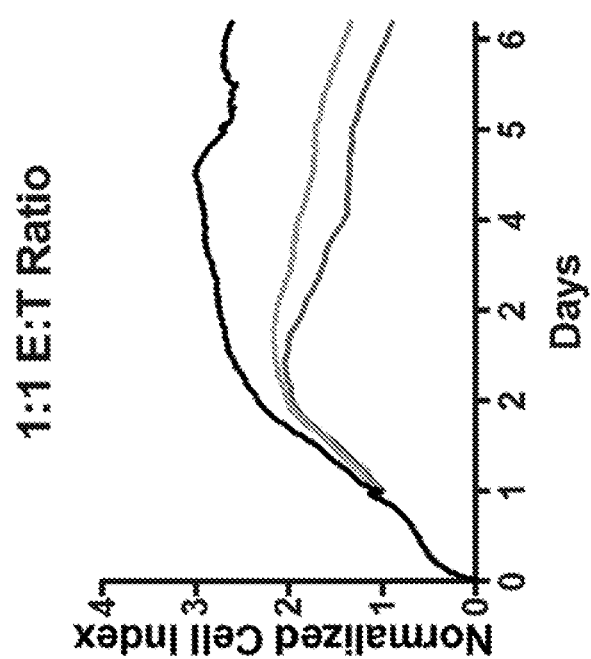

FIGS. 1A to 1D shows CHO cells overexpressing CLEC12A (CHO-CLEC12A) were used as target cells. Gammaretroviruses expressing anti-CLEC12A CARs were transduced into primary T cells isolated from healthy PBMCs. Transduction efficiency of each CAR was determined by flow cytometric analysis of mCherry expression (FIGS. 1A and 1B). CAR positive cells were added to target cells at effector to target ratios of either 1:1 (FIG. 1C) or 1:5 (FIG. 1D). UT=Untransduced, MFI=median fluorescent intensity.

Figures 2A, 2B:
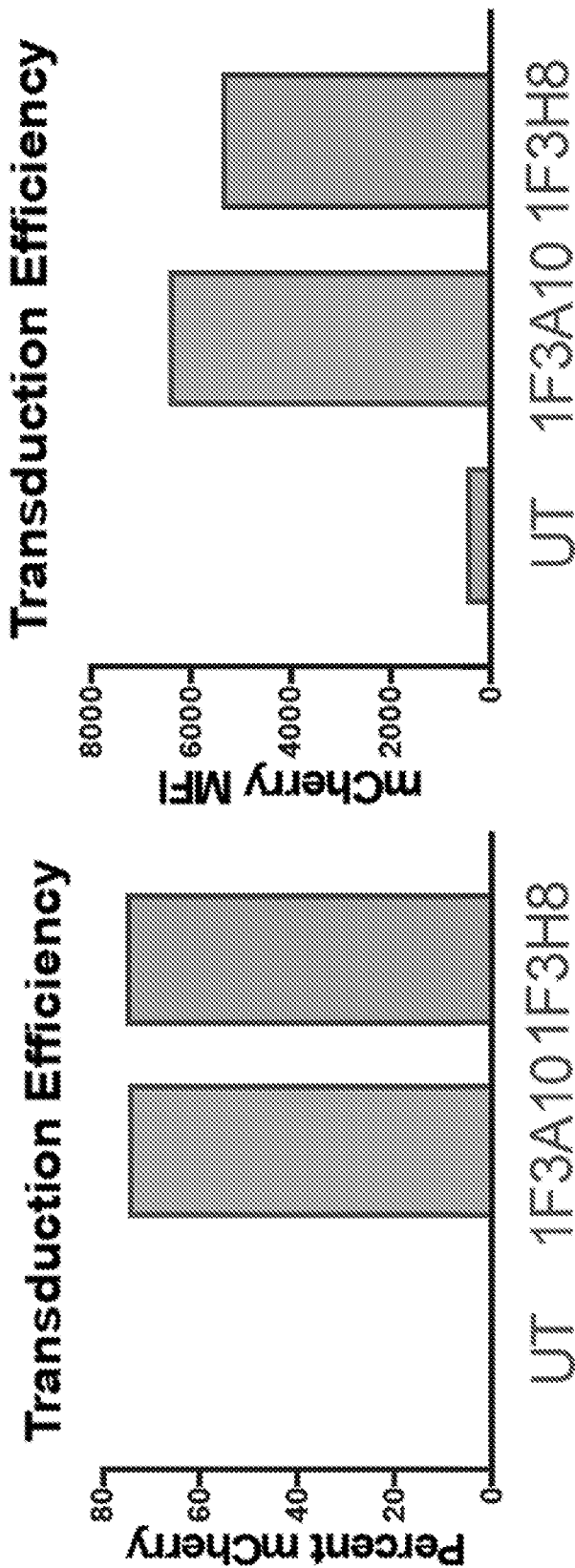
Figures 2G, 2H:
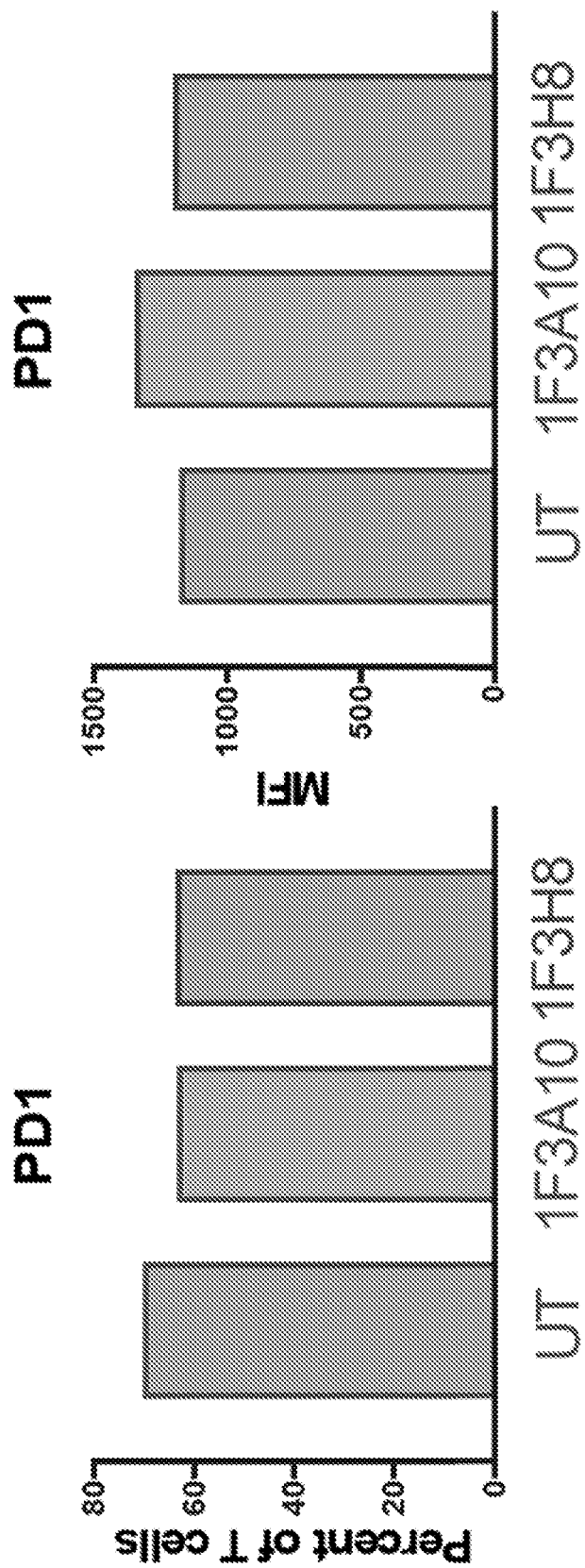
Figure 2I:
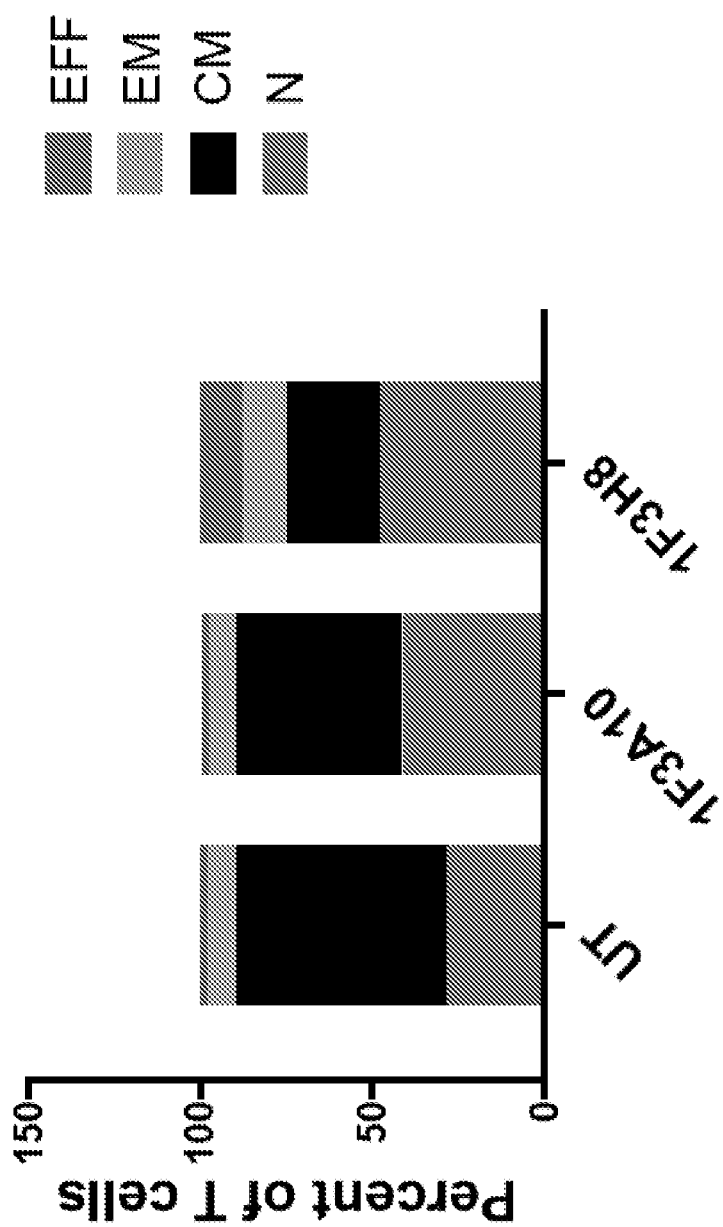

FIGS. 2A to 2I show immunephenotype of anti-CLEC12A CARs. Healthy T cells isolated from PBMCs were transduced with anti-CLEC12A CARs. Following 1-week of culturing without antigen stimulation, cells were stained for CD3, CD4, CD8, PD1, CCR7, and CD45RA, and data were collected on a flow cytometer. Transduction efficiency was determined based on mCherry expression (FIGS. 2A and 2B). Live, CAR positive T cells were analyzed for CD4, CD8, and PD1 expression (FIGS. 2C-2H). T cells subsets were also analyzed based on CCR7 and CD45RA expression (FIG. 2I). EFF=effector, EM=effector memory, CM=central memory, N=Naïve.

Figure 3C:
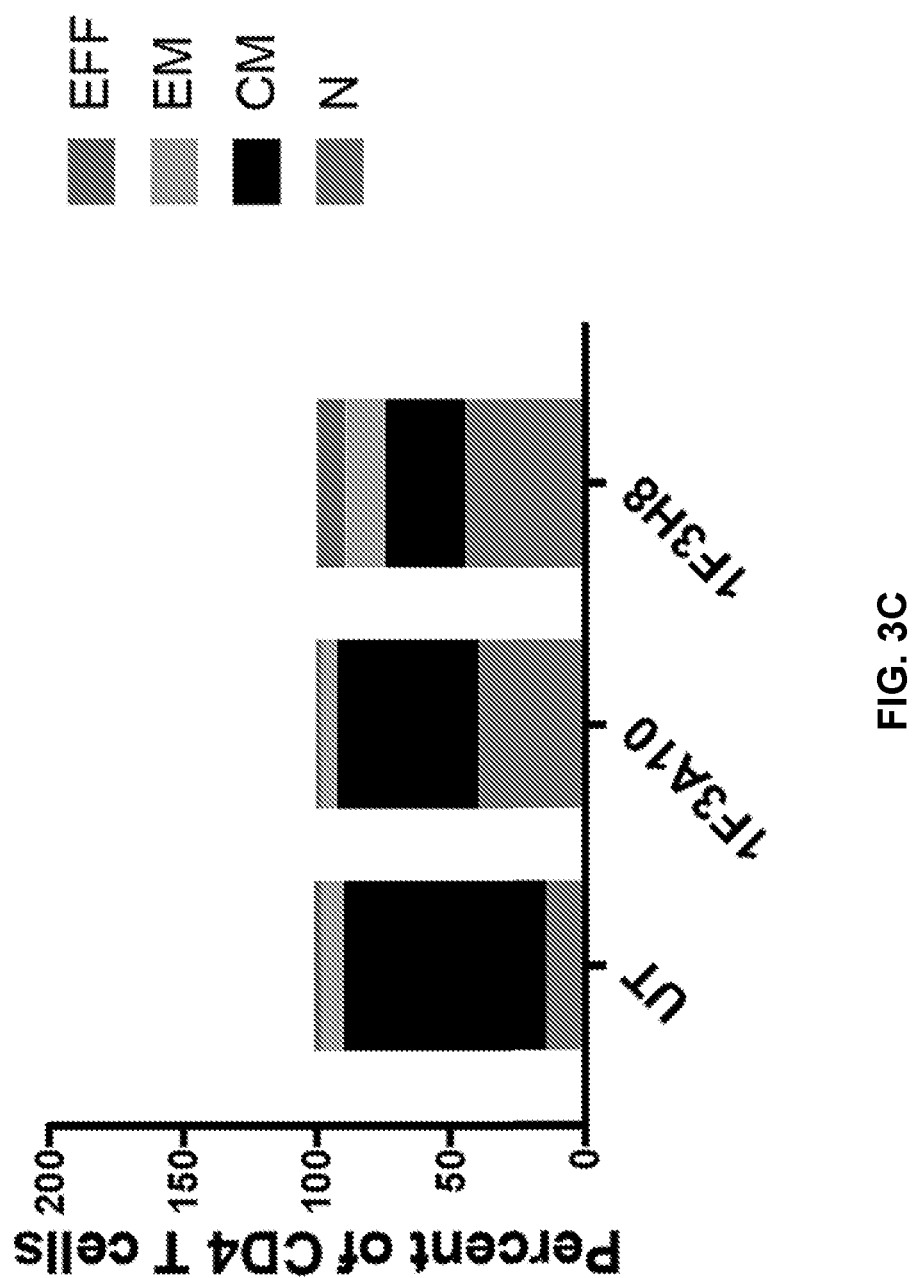
Figures 3D, 3E:
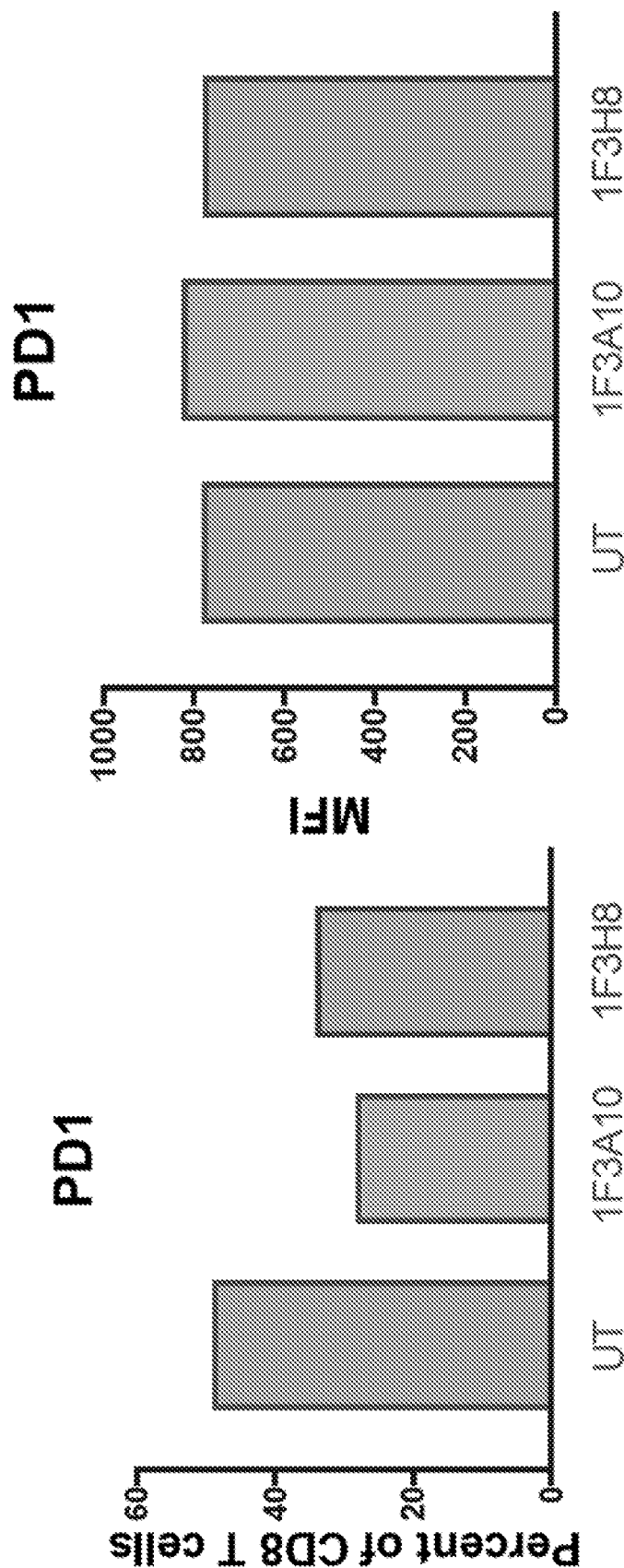
Figure 3F:
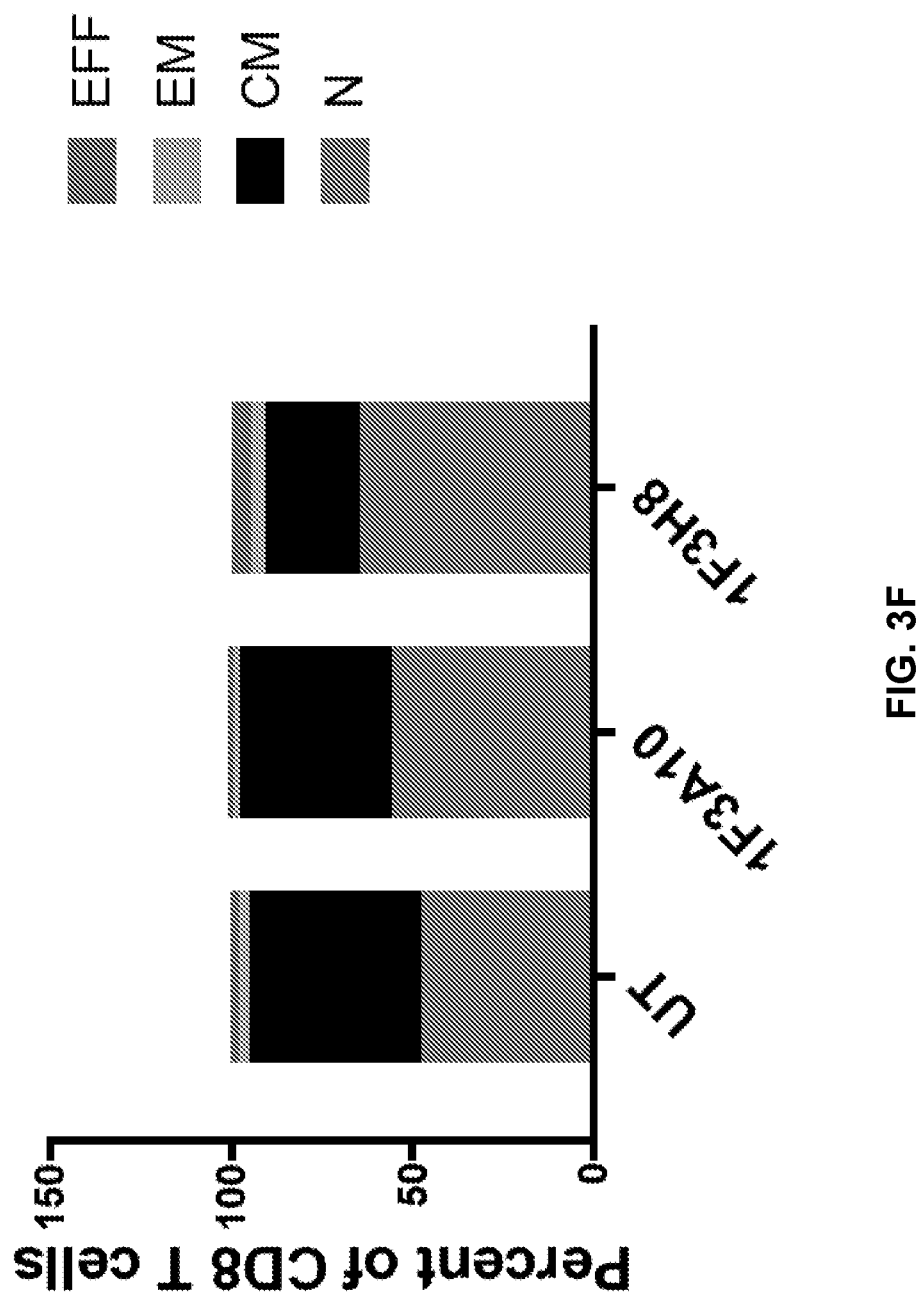

FIGS. 3A to 3F show CD4 and CD8 immunephenotype of anti-CLEC12A CARs. CD4 and CD8 T cells were analyzed for expression of PD1 (FIGS. 3A & 3B, 3D & 3E) and for T cells subsets (FIGS. 3C & 3F). EFF=effector, EM=effector memory, CM=central memory, N=Naïve.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a CLEC12A antigen binding domain, a transmembrane domain, an intracellular signaling domain, and a co-stimulatory signaling region,
wherein the CLEC12A antigen binding domain is a single-chain variable fragment (scFv) of an antibody that specifically binds CLEC12A,
wherein the CDR1 sequence of the $V_H$ domain comprises the amino acid sequence SEQ ID NO:1; the CDR2 sequence of the $V_H$ domain comprises the amino acid sequence SEQ ID NO:4 or SEQ ID NO:5; the CDR3 sequence of the $V_H$ domain comprises the amino acid sequence SEQ ID NO:8; the CDR1 sequence of the $V_L$ comprises the amino acid sequence SEQ ID NO:10; the CDR2 sequence of the $V_L$ domain comprises the amino acid sequence SEQ ID NO:13; and the CDR3 sequence of the $V_L$ domain comprises the amino acid sequence SEQ ID NO:15; or
wherein the CDR1 sequence of the $V_H$ domain comprises the amino acid sequence SEQ ID NO:2; the CDR2 sequence of the $V_H$ domain comprises the amino acid sequence SEQ ID NO:4; the CDR3 sequence of the $V_H$ domain comprises the amino acid sequence SEQ ID NO:8; the CDR1 sequence of the $V_L$ comprises the amino acid sequence SEQ ID NO:11; the CDR2 sequence of the $V_L$ domain comprises the amino acid sequence SEQ ID NO:13; and the CDR3 sequence of the $V_L$ domain comprises the amino acid sequence SEQ ID NO:15; or
wherein the CDR1 sequence of the $V_H$ domain comprises the amino acid sequence SEQ ID NO:3; the CDR2 sequence of the $V_H$ domain comprises the amino acid sequence SEQ ID NO:4 or SEQ ID NO:5; the CDR3 sequence of the $V_H$ domain comprises the amino acid sequence SEQ ID NO:9; the CDR1 sequence of the $V_L$ comprises the amino acid sequence SEQ ID NO:11; the CDR2 sequence of the $V_L$ domain comprises the amino acid sequence SEQ ID NO:13; and the CDR3 sequence of the $V_L$ domain comprises the amino acid sequence SEQ ID NO:15.

2. The polypeptide of claim 1, wherein the $V_H$ domain comprises the amino acid sequence SEQ ID NO:16, and wherein the $V_L$ domain comprises the amino acid sequence SEQ ID NO:22; or wherein the $V_H$ domain comprises the amino acid sequence SEQ ID NO:18, and wherein the $V_L$ domain comprises the amino acid sequence SEQ ID NO:22; or wherein the $V_H$ domain comprises the amino acid sequence SEQ ID NO:20, and wherein the $V_L$ domain comprises the amino acid sequence SEQ ID NO:22.

3. The polypeptide of claim 1, wherein the costimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

4. The polypeptide of claim 1, wherein the CAR polypeptide is defined by the formula:

SP-CLEC12A-HG-TM-CSR-ISD; or

SP-CLEC12A-HG-TM-ISD-CSR wherein "SP" represents a signal peptide,
wherein "CLEC12A" represents a CLEC12A-binding region,
wherein "HG" represents and optional hinge domain,
wherein "TM" represents a transmembrane domain,
wherein "CSR" represents a co-stimulatory signaling region,
wherein "ISD" represents an intracellular signaling domain, and wherein "—" represents a bivalent linker.

5. The polypeptide of claim 1, wherein the intracellular signaling domain comprises a CD3 zeta (CD3ζ) signaling domain.

6. An isolated nucleic acid sequence encoding the recombinant polypeptide of claim 1.

7. A vector comprising the isolated nucleic acid sequence of claim 6.

8. A cell comprising the vector of claim 7.

9. The cell of claim 8, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

10. The cell of claim 9, wherein the cell exhibits an anti-tumor immunity when the antigen binding domain of the CAR binds to CLEC12A.

11. A cell comprising the chimeric antigen receptor (CAR) polypeptide of claim 1.

12. The cell of claim 11, wherein the cell is an autologous or allogeneic Epstein-Barr virus (EBV)-specific cytotoxic lymphocyte.

* * * * *